(12) United States Patent
Shimizu et al.

(10) Patent No.: US 8,969,040 B2
(45) Date of Patent: Mar. 3, 2015

(54) PHARMACEUTICAL AGENT COMPRISING ANTI-BMP9 ANTIBODY AS ACTIVE INGREDIENT FOR TREATMENT OF ANEMIA SUCH AS RENAL ANEMIA AND CANCER ANEMIA

(71) Applicant: Kyowa Hakko Kirin Co., Ltd, Tokyo (JP)

(72) Inventors: Kiyoshi Shimizu, Tokyo (JP); Yuji Yamazaki, Tokyo (JP); Tsuguo Kubota, Tokyo (JP); Kaname Kimura, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 0 days.

(21) Appl. No.: 13/933,295

(22) Filed: Jul. 2, 2013

(65) Prior Publication Data

US 2014/0056902 A1 Feb. 27, 2014

Related U.S. Application Data

(60) Provisional application No. 61/666,981, filed on Jul. 2, 2012.

(51) Int. Cl.
| | | |
|---|---|---|
| *A61K 39/395* | (2006.01) | |
| *C07K 16/00* | (2006.01) | |
| *C07K 16/18* | (2006.01) | |
| *C07K 16/22* | (2006.01) | |
| *C12N 15/13* | (2006.01) | |
| *C12N 15/53* | (2006.01) | |
| *C12N 5/10* | (2006.01) | |
| *C12N 15/09* | (2006.01) | |

(52) U.S. Cl.
CPC .............. *A61K 39/3955* (2013.01); *C07K 16/18* (2013.01); *C12N 15/09* (2013.01)
USPC .......... 435/69.1; 435/326; 435/328; 435/335; 435/252.3; 435/320.1; 536/23.53; 530/387.3; 530/388.1; 530/388.23; 424/133.1; 424/135.1; 424/139.1; 424/141.1; 424/145.1

(58) Field of Classification Search
None
See application file for complete search history.

(56) References Cited

U.S. PATENT DOCUMENTS

| 2009/0017019 A1* | 1/2009 | Shields et al. ............. 424/133.1 |
| 2012/0183543 A1 | 7/2012 | Buckler et al. |

FOREIGN PATENT DOCUMENTS

| WO | 2009/084738 A1 | 7/2009 |
| WO | 2010/126169 A1 | 11/2010 |
| WO | 2010/128158 A1 | 11/2010 |

OTHER PUBLICATIONS

Herrera et al. (2009, BMC Cell Biology 10:1-11).*
R&D (www.rndsystems.com/Products/mab3209; accessed Jun. 19, 2014).*
International Searching Authority, International Search Report (PCT/ISA/210) dated Aug. 6, 2013 issued in International Application No. PCT/JP2013/067994.
Brown M. et al., "Crystal Structure of BMP-9 and Functional Interactions with Pro-region and Receptors," The Journal of Biological Chemistry, Jul. 1, 2005, vol. 280 No. 26, pp. 25111-25118.
Miller A. et al., "Bone Morphogenetic Protein-9: An Autocrine/Paracrine Cytokine in the Liver," The Journal of Biological Chemistry, Jun. 16, 2000, vol. 275 No. 24, pp. 17937-17945.
Leblanc E. et al., "BMP-9-Induced Muscle Heterotopic Ossification Requires Changes to the Skeletal Muscle Microenvironment," Journal of Bone and Mineral Research, Jun. 2011, vol. 26 No. 6, pp. 1166-1177.
Lopez-Coviella I. et al., "Upregulation of Acetylocholine Synthesis by Bone Morphogenetic Protein 9 in a Murine Septal Cell Line," Journal of Physiology Paris, 2002, vol. 96, pp. 53-59.
Tadao A., Blood Frontier, 2008, vol. 18 No. 2, pp. 17-18.
Mitsuiki K. et al., "Problems Related to ESA-Resistant Anemia in Hemodialysis Patients," Clinical Dialysis, 2010, vol. 26 No. 2, pp. 59-66.
"GDF2/BMP9 Rabbit Anti-Human Polyclonal (N-Terminus) Antibody," LSBio Catalog, Mar. 16, 2012, Catalog ID. LS-C97992, pp. 1-3.
"Human/Mouse BMP-9 Antibody, R and D Systems Catalog," LSBio Catalog, 2011, Catalog ID. AF3209, pp. 1-2.
"Guideline for Renal Anemia in Chronic Kidney Disease," Journal of Japanese Society for Dialysis Therapy, 2008, vol. 41 No. 10, pp. 662-716.
Kidney and Dialysis, 2011, vol. 71 No. 2, pp. 247-251.
Kidney and Dialysis, 2011, vol. 71 No. 2, pp. 276-278.
Ploemacher RE. et al., "Bone Morphogenetic Protein 9 is a Potent Synergistic Factor for Murine Hemopoietic Progenitor Cell Generation and Colony Formation in Serum-free Cultures," Leukemia, 1999, vol. 13, pp. 428-437.
Chen C. et al., "An Integrated Functional Genomics Screening Program Reveals a Role for BMP-9 in Glucose Homeostasis," Nature Biotechnology, Mar. 2003, vol. 21, pp. 294-301.

(Continued)

*Primary Examiner* — Elizabeth C Kemmerer
(74) *Attorney, Agent, or Firm* — Sughrue Mion, PLLC

(57) ABSTRACT

The present invention provides an anti-BMP9 (Bone morphogenetic protein-9) monoclonal antibody or an antibody fragment thereof binding to human BMP9, a hybridoma producing the antibody or the antibody fragment, a DNA encoding the antibody or the antibody fragment, a vector comprising the DNA, a transformant obtained by introduction of the vector, a method for preparing the antibody or the antibody fragment using the hybridoma or the transformant, and a therapeutic agent comprising the antibody or the antibody fragment as an active ingredient. Further, the present invention provides a pharmaceutical composition comprising the antibody or the antibody fragment as an active ingredient for the treatment of anemia such as renal anemia, cancer anemia or the like, and a method for treating anemia such as renal anemia, cancer anemia or the like using the same.

14 Claims, 13 Drawing Sheets

(56) References Cited

OTHER PUBLICATIONS

Standard Hematology (Igaku-Shoin Ltd), 2000, pp. 11-15.
David L. et al., "Bone Morphogenetic Protein-9 is a Circulating Vascular Quiescence Factor," Circulation Research, Apr. 25, 2008, vol. 102, pp. 1-17.
Cunha S. et al., "Genetic and Pharmacological Targeting of Activin Receptor-like Kinase 1 Impairs Tumor Growth and Angiogenesis," The Journal of Experimental Medicine, Jan. 11, 2010, vol. 207 No. 1, pp. 85-100.
Chen H. et al., "BMP10 is Essential for Maintaining Cardiac Growth During Murine Cardiogenesis," The Company of Biologists: Development and Disease, Jan. 7, 2004, vol. 131, pp. 2219-2231.
Kang Q. et al., "Characterization of the Distinct Orthotopic Bone-Forming Activity of 14 BMPs Using Recombinant Adenovirus-Mediated Gene Delivery," Gene Therapy, Jul. 22, 2004, vol. 11, pp. 1312-1320.
Sharff K. et al., "Hey1 Basic Helix-Loop-Helix Protein Plays an Important Role in Mediating BMP9-Induced Osteogenic Differentiation of Mesenchymal Progenitor Cells," The Journal of Biological Chemistry, Jan. 2, 2009, vol. 284 No. 1, pp. 649-659.

* cited by examiner

```
             123456789012345678901234567890 12345 67890123456789 012345678901234
10D5 Antibody EVKLEESRGGLVQPGGSMKLSCVASGFTFS NYWMN WVRQSPEKGLEWVA HIRLKSDNYATHYAE
         HV0  EVQLVESGGGLVQPGGSLRLSCAASGFTFS       WVRQAPGKGLEWVG
         HV3  EVQLVESGGGLVQPGGSLRLSCAASGFTFS  CDR1 WVRQAPGKGLEWVA      CDR2
        HV4a  EVQLVESRGGLVQPGGSMRLSCAASGFTFS       WVRQAPGKGLEWVG
        HV4b  EVQLVESGGGLVQPGGSLRLSCAASGFTFS       WVRQAPGKGLEWVA
        HV7a  EVQLVESRGGLVQPGGSMRLSCAASGFTFS       WVRQAPGKGLEWVA
        HV7b  EVQLVESRGGLVQPGGSMRLSCAASGFTFS       WVRQAPGKGLEWVA
         HV9  EVQLVESRGGLVQPGGSMRLSCAASGFTFS       WVRQAPGKGLEWVA 5678 901234567890123456789012345678 90 12345678 90123456789
10D5 Antibody SVRG RFTISRDDSKSSVFLQMNNLRAEDTGIYYCTG GSNYVFAF WGQGTLVTVSA
         HV0       RFTISRDDSKNSLYLQMNSLKTEDTAVYYCAR          WGQGTLVTVSS
         HV3       RFTISRDDSKNSLYLQMNSLKTEDTAVYYCTG          WGQGTLVTVSS
        HV4a  CDR2 RFTISRDDSKSSLYLQMNSLKTEDTAVYYCAG  CDR3    WGQGTLVTVSS
        HV4b       RFTISRDDSKNSLYLQMNSLKTEDTAIYYCTG          WGQGTLVTVSS
        HV7a       RFTISRDDSKSSLYLQMNSLKTEDTGVYYCTG          WGQGTLVTVSS
        HV7b       RFTISRDDSKNSVYLQMNSLKTEDTGVYYCTG          WGQGTLVTVSS
         HV9       RFTISRDDSKSSVYLQMNSLKTEDTGIYYCTG          WGQGTLVTVSS
```

Fig. 12

```
              123456789012345678901230 456789012345678 901234567890123 4567890
10D5 Antibody DIVLTQSPASLAVSLGQRATISC  RASESVDNYGISFMN  WFQQKPGQPPKLLIY AASNQGS
         LV0  DIVMTQSPDSLAVSLGERATINC                   WYQQKPGQPPKLLIY
         LV2  DIVMTQSPDSLAVSLGERATINC                   WFQQKPGQPPKLLIY
         LV3  DIVMTQSPDSLAVSLGERATINC        CDR1       WFQQKPGQPPKLLIY  CDR2
         LV4  DIVLTQSPDSLAVSLGERATINC                   WYQQKPGQPPKLLIY
         LV6  DIVLTQSPDSLAVSLGERATINC                   WFQQKPGQPPKLLIY 123456789012345678901234567890120 345678901 2345678901
10D5 Antibody GVPARFSGSGSGTDFSLNIHPMEEDDTAMYFC   QQSKEVPWT  FGGGTKLEIK
         LV0  GVPDRFSGSGSGTDFTLTISSLQAEDVAVYYC              FGQGTKLEIK
         LV2  GVPDRFSGSGSGTDFTLTISSLQAEDVAVYFC              FGQGTKLEIK
         LV3  GVPDRFSGSGSGTDFTLTISPLQAEDVAVYFC    CDR3      FGQGTKLEIK
         LV4  GVPDRFSGSGSGTDFTLTISPMQAEDVAMYYC              FGQGTKLEIK
         LV6  GVPDRFSGSGSGTDFTLTISPMQAEDVAMYFC              FGQGTKLEIK
```

Fig. 13

PHARMACEUTICAL AGENT COMPRISING ANTI-BMP9 ANTIBODY AS ACTIVE INGREDIENT FOR TREATMENT OF ANEMIA SUCH AS RENAL ANEMIA AND CANCER ANEMIA

BACKGROUND OF THE INVENTION

1. Field of the Invention

The present invention relates to an anti-BMP9 (Bone morphogenetic protein-9) monoclonal antibody or an antibody fragment thereof binding to human BMP9, a hybridoma producing the antibody or the antibody fragment, a DNA encoding the antibody or the antibody fragment, a vector containing the DNA, a transformant obtained by introduction of the vector, a method for preparing the antibody or the antibody fragment using the hybridoma or the transformant, and a therapeutic agent including the antibody or the antibody fragment as an active ingredient.

Further, the present invention relates to a pharmaceutical composition comprising the antibody or the antibody fragment as an active ingredient for the treatment of anemia such as renal anemia, cancer anemia or the like, and a method for treating anemia such as renal anemia, cancer anemia or the like using the composition.

2. Brief Description of the Background Art

BMP9 is an abbreviation for bone morphogenetic protein 9, and also called GDF2. BMP9 belongs to a BMP (Bone morphogenetic protein) family molecule composed of approximately 20 members, and human BMP9 is a secretory protein composed of 429 amino acids (Non-Patent Document 1).

It is know that BMP9 is mainly expressed in the spinal cord or septum in the fetal stage and in the liver in the adult stage (Non-Patent Documents 2, 3, and 4) and that human BMP9 is a blood circulation factor present in the blood at a concentration of 2-12 ng/mL (Non-Patent Document 5).

Until now, there have been no reports on in vivo functions of BMP9 based on BMP9-deficient mice or administration of anti-BMP9 antibody to animals, but a few reports have been made based on the findings of in vitro studies. Such report includes, for example, a promoting action on generation of hypertrophic chondrocytes or chondrogenic differentiation from mesenchymal cells (Non-Patent Documents 6, 7, and 8), or a promoting action on production or colony formation of blood progenitor cells (Non-Patent Document 9). From these reports, however, it was very difficult to predict that anti-BMP9 antibody has the erythropoietic action in vivo.

Further, a monoclonal antibody having a BMP9-neutralizing activity has been commercialized as an anti-BMP9 monoclonal antibody by R&D systems (Clone No. 360107), but no other antibodies have been known.

Anemia refers to "a condition of having a reduction in the number of erythrocytes, the hemoglobin concentration, and the hematocrit value per unit volume of blood, compared to normal condition (Non-Patent Document 10). There are many factors involved in the control of erythropoiesis, but erythropoietin is the most important and specific factor (hereinafter, referred to as EPO).

EPO promotes proliferation and differentiation of late-stage colony-forming unit-erythroid (CFU-E), and consequently, increases erythrocyte production in vivo (Non-Patent Document 10). EPO is a glycoprotein hormone that is composed of 165 amino acids and has a molecular weight of 30 kDa, and is mainly produced in the kidney (Non-Patent Document 10).

Anemia accompanied by kidney disease (renal anemia) is the most frequent complication of chronic kidney disease (CKD), characterized in that reduced EPO production and reduced number of erythrocytes result from failure of the EPO-producing tissue, kidney (Non-Patent Document 11). It is known that renal anemia affects development and progression of cardiovascular disease, and progression of renal dysfunction, as well as QOL (Non-Patent Documents 11 and 12).

A recombinant human erythropoietin that is a therapeutic agent for renal anemia and a second-generation EPO agent which has been recently developed to have a long blood half-life are generally called ESA (erythropoiesis-stimulating agent) (Non-Patent Document 13).

ESA has a strong erythropoietic action. In some cases, however, ESA administration does not show a satisfactory anemia-improving effect in 15-20% of dialysis patients with renal failure (which called ESA-resistant anemia or ESA-hyporesponsive anemia) (Non-Patent Document 13).

The results of large-scale intervention trials (CREATE and CHOIR studies) show that excessive administration of ESA to patients with ESA resistance causes a poor life prognosis (Non-Patent Documents 11, 12, and 13). Under this background, a significant issue for renal anemia treatment is to overcome ESA resistance, and there is a strong demand to develop a new erythropoiesis-stimulating agent having a different mechanism from EPO.

Meanwhile, anemia accompanied by malignant tumor (cancer anemia) is a symptom observed in many cancers, and caused by two factors: one is associated with disease progression including blood loss and the other relates to chemotherapy or radiotherapy (Non-Patent Document 14).

ESA is known to be effective in cancer anemia, but concerns about a possibility of promoting tumor progression or thrombotic infarction by ESA treatment are pointed out (Non-Patent Document 14). With respect to cancer anemia, therefore, there is also a demand to develop a new erythropoiesis-stimulating agent having a different mechanism from EPO.

As described above, it is required to develop an erythropoiesis-stimulating agent having a different mechanism from EPO for the treatment of renal anemia and cancer anemia. Also, the efficacy and strength of the drug must be considered. Specifically, Japanese criteria for starting administration of ESA is that in case of dialysis patients, the hemoglobin concentration is less than 10 g/dL and the drug should have the efficacy of controlling the hemoglobin concentration between 10-11 g/dL; and that in case of patients with predialysis chronic kidney disease, the hemoglobin concentration is less than 11 g/dL for starting administration of ESA and the drug should have the efficacy of controlling the hemoglobin concentration between 11-13 g/dL (Non-Patent Document 15).

In other words, new erythropoiesis-stimulating agents are required to have two characteristics: efficacy of increasing the hemoglobin concentration by at least 1-2 g/dL and EPO-independency.

CITATION LIST

Non-Patent Document

[Non-Patent Document 1] J. Biol. Chem., 280, 26, 25111 (2005)

[Non-Patent Document 2] Nat. Biotechnology, 21, 294 (2003)

[Non-Patent Document 3] J. Biol. Chem., 275, 24, 17937 (2000)

[Non-Patent Document 4] J. Physiology-Paris, 96, 53 (2002)
[Non-Patent Document 5] Circ. Res., 102, 8, 914 (2008)
[Non-Patent Document 6] Gene Ther., 11, 17, 1312 (2004)
[Non-Patent Document 7] J. Biol. Chem., 284, 1, 649 (2009)
[Non-Patent Document 8] J. Boneminer. Res., 26, 6, 1166 (2011)
[Non-Patent Document 9] Leukemia, 13, 3, 428 (1999)
[Non-Patent Document 10] Standard hematology (IGAKU-SHOIN Ltd.) (2000)
[Non-Patent Document 11] Blood Frontier, 18, 2, 17 (2008)
[Non-Patent Document 12] Kidney and Dialysis, 71, 2, 247 (2011)
[Non-Patent Document 13] Clinical Dialysis, 26, 2, 59 (2010)
[Non-Patent Document 14] Kidney and Dialysis, 71, 2, 276 (2011)
[Non-Patent Document 15] Journal of Japanese Society for Dialysis Therapy, 41, 10, 661 (2008)

SUMMARY OF THE INVENTION

An object of the present invention is to provide a therapeutic agent including an anti-BMP9 antibody as an active ingredient for the improvement of anemia such as renal anemia, cancer anemia or the like.

The present inventors have tried to acquire the anti-BMP9 antibody using BMP9-deficient mice for the purpose of clarifying in vivo function of anti-BMP9 antibody, and finally, they succeeded in acquiring the anti-BMP9 antibody having a remarkably improved binding ability to BMP9, compared to the conventional antibodies.

Further, they have made many efforts to demonstrate in vivo function of anti-BMP9 antibody using the obtained antibody. Surprisingly, they found that the anti-BMP9 antibody has an erythropoietic activity, and moreover, its erythropoietic activity is higher than those of the conventional antibodies, and the antibody inhibits the binding of human BMP9 and human BMPRII.

Further, the results of analyzing the action mechanism showed that the erythropoietic activity of the obtained antibody is not mediated by an increase in the blood EPO concentration, that is, is attributed to a mechanism different from that of EPO. The activity of anti-BMP9 antibody was also examined by using a renal anemia model, ⅚ nephrectomy rat, and the result showed that it has a renal anemia-improving effect.

Based on these findings, the present inventors have considered providing a therapeutic agent including the anti-BMP9 antibody as an active ingredient for the treatment of anemia such as renal anemia, cancer anemia or the like, thereby completing the present invention.

The antibody of the present invention is the anti-BMP9 antibody that has a remarkably improved binding ability to BMP9, compared to the conventional antibodies, has more excellent erythropoietic activity than the conventional antibodies, and inhibits the binding of human BMP9 and human BMPRII. Further, the erythropoietic activity of the antibody of the present invention is not mediated by an increase in the blood EPO concentration. Furthermore, the antibody of the present invention has a renal anemia-improving effect. The antibody of the present invention having these characteristics is offered as an active ingredient, thereby providing a therapeutic agent for anemia such as renal anemia, cancer anemia or the like.

BRIEF DESCRIPTION OF THE DRAWINGS

FIG. 12 shows the heavy chain variable region of 10D5-2-3 antibody-humanized antibody generated. The amino acid sequences of H chain variable region, VH of 10D5-2-3 antibody (SEQ ID NO:49), HV0 (SEQ ID NO:116), HV3 (SEQ ID NO:120), HV4a (SEQ ID NO:122), HV4b (SEQ ID NO:124), HV7a (SEQ ID NO:126), HV7b (SEQ ID NO:128), and HV9 (SEQ ID NO:130) are shown.

FIG. 13 shows the light chain variable region of 10D5-2-3 antibody-humanized antibody generated. The amino acid sequences of L chain variable region, VL of 10D5-2-3 antibody (SEQ ID NO:52), LV0 (SEQ ID NO:118), LV2 (SEQ ID NO:132), LV3 (SEQ ID NO:134), LV4 (SEQ ID NO:136), and LV6 (SEQ ID NO:138) are shown.

DETAILED DESCRIPTION OF THE INVENTION

Figure 1:
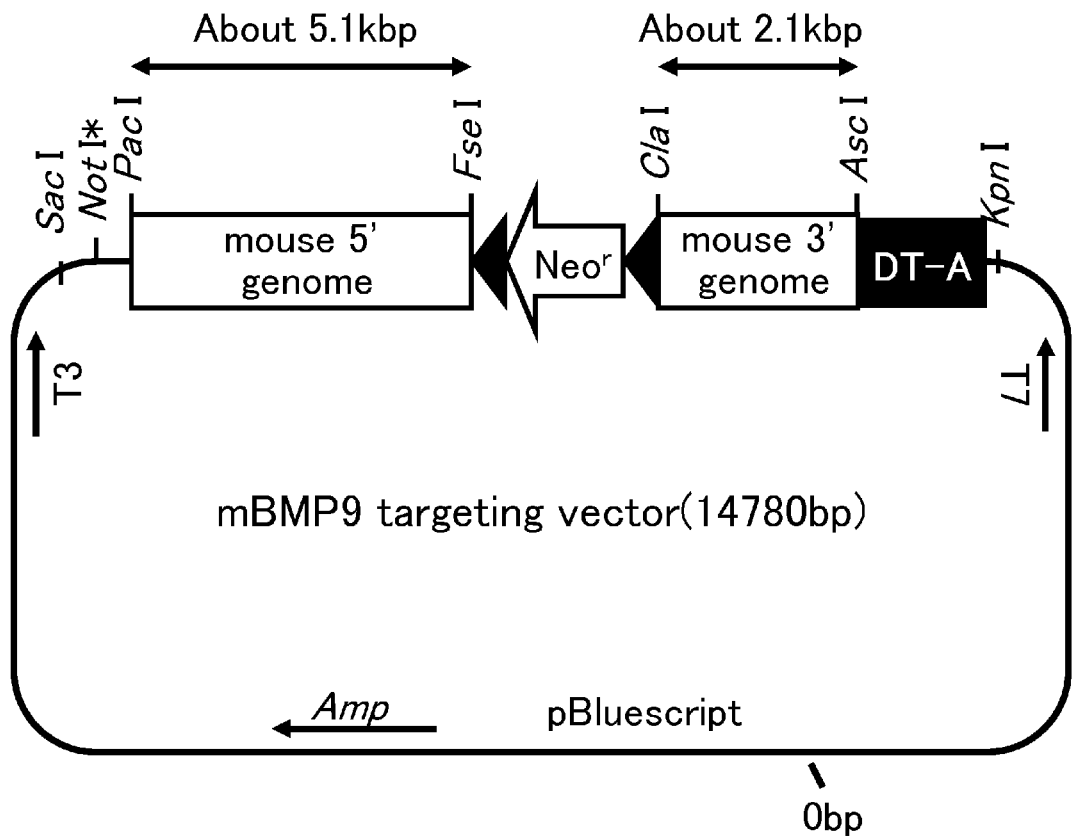
FIG. 1 shows the structure of a vector for mouse BMP9 gene knockout, in which mouse 5' genome is the 5' homology region of the vector for BMP9 gene knockout, Neo″ is a neomycin resistant gene, mouse 3' genome is the 3' homology region of the vector for BMP9 gene knockout, DT-A is a diphtheria toxin A chain gene, T3 is a T3 promoter, T7 is a T7 promoter, and pBluescript is a cloning vector.

The present invention relates to the following (1) to (15).
(1) A monoclonal antibody or an antibody fragment thereof, which is one antibody selected from the following (a) to (e); or which binds to human BMP9 while competing with the antibody and binds to human BMP9 with a dissociation constant equal to or less than $1 \times 10^{-10}$ mol/L:

(a) an antibody which comprises a heavy chain of an antibody which comprises complementarity determining regions (hereinafter, referred to as CDR) 1 to 3 comprising the amino acid sequences represented by SEQ ID NOs:54 to 56, respectively, and comprises a light chain of an antibody which comprises CDRs 1 to 3 comprising the amino acid sequences represented by SEQ ID NOs:57 to 59, respectively, (b) an antibody which comprises a heavy chain of an antibody which comprises CDRs 1 to 3 comprising the amino acid sequences represented by SEQ ID NOs:60 to 62, respectively, and comprises a light chain of an antibody which comprises CDRs 1 to 3 comprising the amino acid sequences represented by SEQ ID NOs:63 to 65, respectively, (c) an antibody which comprises a heavy chain variable region of an antibody comprising the amino acid sequence represented by SEQ ID NO:48, and comprises a light chain variable region of an antibody comprising the amino acid sequences represented by SEQ ID NO:51, (d) an antibody which comprises a heavy chain variable region of an antibody comprising the amino acid sequence represented by SEQ ID NO:49, and comprises a light chain variable region of an antibody comprising the amino acid sequences represented by SEQ ID NO:52, and (e) an antibody which comprises a heavy chain variable region of an antibody comprising the amino acid sequence represented by SEQ ID NO:128, and comprises a light chain variable region of an antibody comprising the amino acid sequences represented by SEQ ID NO:132.

(2) The monoclonal antibody or the antibody fragment thereof described in (1), wherein the monoclonal antibody binds to an epitope to which the one antibody selected from the (a) to (e) binds.

(3) The monoclonal antibody or the antibody fragment thereof described in (1), wherein the monoclonal antibody or the antibody fragment thereof is a recombinant antibody.

(4) The monoclonal antibody or the antibody fragment thereof described in (3), wherein the recombinant antibody is selected from a human chimeric antibody, a humanized antibody and a human antibody.

(5) A monoclonal antibody or an antibody fragment thereof selected from the following (a) to (c):

(a) a monoclonal antibody or an antibody fragment thereof which comprises a heavy chain of an antibody which comprises CDRs 1 to 3 comprising the amino acid sequences represented by SEQ ID NOs:54 to 56, respectively, and comprises a light chain of an antibody which comprises CDRs 1 to 3 comprising the amino acid sequences represented by SEQ ID NOs:57 to 59, respectively, (b) a monoclonal antibody or an antibody fragment thereof which comprises a heavy chain of an antibody which comprises CDRs 1 to 3 comprising the amino acid sequences represented by SEQ ID NOs:60 to 62, respectively, and comprises a light chain of an antibody which comprises CDRs 1 to 3 comprising the amino acid sequences represented by SEQ ID NOs:63 to 65, respectively, and (c) an antibody or an antibody fragment thereof which comprises a heavy chain variable region of an antibody comprising the amino acid sequence represented by SEQ ID NO:128, and comprises a light chain variable region of an antibody comprising the amino acid sequences represented by SEQ ID NO:132.

(6) The monoclonal antibody or the antibody fragment thereof described in (1) or (5), wherein the monoclonal antibody or the antibody fragment thereof binds to at least Lys at position 87, Asp at position 89, Met at position 90, and Pro at position 93 in the amino acid sequence of human BMP9 mature region represented by SEQ ID NO:67.

(7) The antibody fragment described in (1) or (5), wherein the antibody fragment is selected from Fab, Fab', F(ab')$_2$, a single chain antibody (scFv), a dimerized V region (diabody), a disulfide stabilized V region (dsFv) and a peptide comprising CDR.

(8) A DNA encoding the monoclonal antibody or the antibody fragment thereof described in (1) or (5).

(9) A recombinant vector comprising the DNA described in (8).

(10) A transformant obtained by introducing the recombinant vector described in (9) into a host cell.

(11) A method for preparing the monoclonal antibody or the antibody fragment thereof described in (1) or (5), comprising culturing the transformant described in (10) in a medium to form and accumulate the monoclonal antibody or the antibody fragment thereof described in (1) or (5) in the culture broth, and collecting the antibody or the antibody fragment thereof from the culture broth.

(12) A method for immunologically detecting or measuring human BMP9 using the monoclonal antibody or the antibody fragment thereof described in (1) or (5).

(13) A pharmaceutical composition, comprising the monoclonal antibody or the antibody fragment thereof described in (1) or (5) and a pharmaceutically acceptable carrier.

(14) A method for treating human BMP9-involved anemia, comprising administering the monoclonal antibody or the antibody fragment thereof described in (1) or (5).

(15) A method for treating BMP9-involved anemia, comprising administering a monoclonal antibody or an antibody fragment thereof which binds to human BMP9 and inhibits binding of human BMP9 and human BMPRII.

The present invention relates to a monoclonal antibody which binds to human BMP9.

In the present invention, the antibody that competes with an antibody for binding to human BMP9 refers to an antibody having an epitope (also called antigenic determinant) on human BMP9 that is identical or partially identical to the epitope of the antibody of the present invention and a binding activity to the epitope.

The antibody that binds to an epitope identical to the epitope to which the monoclonal antibody of the present invention binds refers to an antibody that recognizes and binds to a sequence identical to the amino acid sequence of human BMP9 recognized by the monoclonal antibody of the present invention.

Human BMP9 is synthesized as a single-chain precursor protein (Pre-Pro protein), which has an amino acid sequence represented by SEQ ID NO:66. This single-chain Pre-Pro protein forms a dimer (Pro dimer), resulting from cleavage of a signal peptide comprising 1 to 22 of the amino acid sequence represented by SEQ ID NO:66 in the Golgi apparatus and formation of a disulfide bond between cysteine residues at position 392.

By furin-like protease, cleavage occurs between amino acid residues, 319 and 320 in the amino acid sequence represented by SEQ ID NO:66, and thus the protein is divided into the N-terminal propeptide fragment having no disulfide bond (peptide containing 23 to 319 amino acids of the amino acid sequence represented by SEQ ID NO:66) and the C-terminal fragment (mature region) having an amino acid sequence represented by SEQ ID NO:67.

The mature region forms a dimer (hereinafter, referred to as mature dimer) via a disulfide bond between the cysteine residues at position 73 of SEQ ID NO:67, after cleavage of the propeptide region. The two molecules of the cleaved N-terminal propeptide region bind with one molecule of the mature dimer via a non-covalent bond to form a complex, which is secreted from the cells [J. Biol. Chem., 280 (26), 25111 (2005)]. Both the mature dimer and the complex of the mature dimer and the N-terminal propeptide region have the BMP9 function.

Therefore, human BMP9 of the present invention includes a polypeptide that contains the amino acid sequence of 320 to 429 (SEQ ID NO:67) corresponding to the mature region in the amino acid sequence represented by SEQ ID NO:66 or GenBank Accession NO. NP_057288 and has the human BMP9 function, a polypeptide that contains an amino acid sequence having a deletion, substitution, or addition of one or more amino acids in the amino acid sequence of 320 to 429 (SEQ ID NO:67) corresponding to the mature region and has the human BMP9 function, and a polypeptide that has an amino acid sequence having 60% or more of homology, preferably 80% or more of homology, and more preferably 90% or more of homology to the amino acid sequence represented by SEQ ID NO:67, and most preferably a polypeptide that has an amino acid sequence having 95% or more of homology thereto and has the human BMP9 function, the above described mature dimer, and the complex of the mature dimer and the N-terminal propeptide region.

The BMP9 function described above refers to involvement of BMP9 in the intracellular signal transduction. In the intracellular signal transduction, BMP9 binds to two receptors of type I and type II belonging to the TGFβ superfamily so as to activate these receptors, followed by Smad1/5/8 phosphorylation. The activated Smad1/5/8 activated by phosphorylation forms a complex with Smad4, which translocates to the nucleus and functions as a transcription factor.

Type I receptor may be exemplified by ALK1 and ALK2. Further, type II receptor may be exemplified by BMP type II receptor (BMPRII), activin type IIa receptor (ActRIIa), and activin type IIb receptor (ActRIIb).

The polypeptide that has the amino acid sequence with a deletion, substitution, or addition of one or more amino acids in the amino acid sequence represented by SEQ ID NO:67 may be obtained by a site-specific mutation [Molecular Cloning, A Laboratory Manual, Second Edition, Cold Spring Harbor Laboratory Press (1989), Current Protocols in molecular Biology, John Wiley&Sons (1987-1997), Nucleic Acids Research, 10, 6487 (1982), Proc. Natl. Acad. Sci. USA, 79, 6409 (1982), Gene, 34, 315 (1985), Proc. Natl. Acad. Sci. USA, 82, 488 (1985)] or the like. For example, a site-specific mutation may be introduced in the gene encoding the polypeptide having the amino acid sequence represented by SEQ ID NO:67.

The number of amino acids that are deleted, substituted, or added is not particularly limited, but preferably one to several tens of amino acids, for example, 1 to 20 amino acids, more preferably one to several amino acids, for example, 1 to 5 amino acids.

The gene encoding human BMP9 may have the base sequence represented by SEQ ID NO:68 or GenBank Accession NO. NM_016204. The gene encoding human BMP9 of the present invention includes a gene that is composed of the base sequence having a deletion, substitution, or addition of one or more bases in the base sequence represented by SEQ ID NO:69 corresponding to the mature region and contains DNA encoding the polypeptide having the human BMP9 function, a gene that is composed of the base sequence having 60% or more of homology, preferably 80% or more of homology, and more preferably 95% or more of homology to the base sequence represented by SEQ ID NO:69 and contains DNA encoding the polypeptide having the human BMP9 function, and a gene that is composed of DNA hybridizable with DNA having the base sequence represented by SEQ ID NO:69 under stringent conditions and contains DNA encoding the polypeptide having the human BMP9 function, or the like.

The DNA hybridizable under stringent conditions means a hybridizable DNA that is obtained by colony hybridization, plaque hybridization, Southern blot hybridization, or DNA microarray using DNA having the base sequence represented by SEQ ID NO:69 as a probe.

In detail, the DNA may be DNA which can be identified by performing hybridization [Molecular Cloning, A Laboratory Manual, Second Edition, Cold Spring Harbor Laboratory Press (1989), Current Protocols in molecular Biology, John Wiley&Sons (1987-1997), DNA Cloning 1: Coretechniques, A Practical Approach, Second Edition, Oxford University, (1995)] at 65° C. in the presence of 0.7 to 1.0 mol/L sodium chloride using a filter or a slide glass with the hybridized colony- or plaque-derived DNA, PCR products or oligo DNA having the sequence immobilized thereon, and then washing the filter or slide glass at 65° C. with a 0.1 to 2-fold concentration SSC solution (1-fold concentration SSC solution consists of 150 mmol/L sodium chloride and 15 mmol/L sodium citrate).

The hybridizable DNA may include DNA having at least 60% or more homology, preferably DNA having 80% or more homology, and more preferably DNA having 95% or more homology to the base sequence represented by SEQ ID NO:69.

In the base sequence of the gene encoding a protein of a eukaryote, genetic polymorphism is often observed. The gene encoding BMP9 of the present invention also includes a gene in which small modification is generated in the base sequence used in the present invention by such polymorphism.

The numerical value of the homology in the present invention may be a numerical value calculated by using a homology search program known by those skilled in the art, unless otherwise indicated. Regarding the base sequence, the numerical value may be calculated by using a default parameter in BLAST [J. Mol. Biol., 215, 403 (1990)] or the like, and regarding the amino acid sequence, the numerical value may be calculated by using a default parameter in BLAST2 [Nucleic Acids Res., 25, 3389 (1997), Genome Res., 7, 649 (1997), http://www.ncbi.nlm.nih.gov/Education/BLASTinfo/information3.html] or the like.

As the default parameter, G (cost to open gap) is 5 for the base sequence and 11 for the amino acid sequence; -E (cost to extend gap) is 2 for the base sequence and 1 for the amino acid sequence; -q (penalty for nucleotide mismatch) is −3; -r (reward for nucleotide match) is 1; -e (expect value) is 10; -W (wordsize) is 11 residues for the base sequence and 3 residues for the amino acid sequence; -y (Dropoff (X) for blast extensions in bits) is 20 for blastn and 7 for a program other than blastn; -X (X dropoff value for gapped alignment in bits) is 15; and Z (final X dropoff value for gapped alignment in bits) is 50 for blastn and 25 for a program other than blastn (http://www.ncbi.nlm.nih.gov/blast/html/blastcgihelp.html).

The polypeptide composed of a partial sequence of the amino acid sequence represented by SEQ ID NO:66 or GenBank Accession NO. NP_057288 can be prepared according to a method known by those skilled in the art. For example, it can be prepared by deleting a part of DNA encoding the amino acid sequence represented by SEQ ID NO:66 and culturing a transformant into which an expression vector including the DNA is introduced.

Also, based on the polypeptide or DNA thus prepared by the above method, a polypeptide including an amino acid sequence in which one or more amino acids are deleted, substituted or added in a partial sequence of the amino acid sequence represented by SEQ ID NO:66 or GenBank Accession NO. NP_057288 can be prepared in the same manner as described above.

The polypeptide composed of a partial sequence of the amino acid sequence represented by SEQ ID NO:66 or GenBank Accession NO. NP_057288, or the polypeptide having an amino acid sequence in which one or more amino acids are deleted, substituted or added in a partial sequence of the amino acid sequence represented by SEQ ID NO:66 or GenBank Accession NO. NP_057288 can be also produced by a chemical synthesis method such as fluorenylmethoxycarbonyl (Fmoc) method, t-butyloxycarbonyl (tBoc) method or the like.

The monoclonal antibody of the present invention (hereinafter, referred to as antibody of the present invention) is an antibody or an antibody fragment thereof that recognizes and binds to the amino acid sequence of human BMP9 or the three-dimensional structure thereof, or that has the property of binding to the amino acid sequence of human BMP9 or the three-dimensional structure thereof, inhibiting the binding of BMP9 and BMPRII, and not inhibiting the binding of BMP9 and ALK1. The monoclonal antibody of the present invention may include a monoclonal antibody or an antibody fragment thereof that binds to human BMP9 and has a dissociation constant of $1 \times 10^{40}$ mol/L or less for human BMP9.

The antibody of the present invention may be, specifically, an antibody that binds to at least val at position 84, Leu at position 95, Tyr at position 97, and His at position 98, or an antibody that binds to at least Lys at position 87, Asp at position 89, Met at position 90, and Pro at position 93, and more preferably, an antibody that binds to at least Lys at position 87, Asp at position 89, Met at position 90, and Pro at position 93 in the amino acid sequence of human BMP9 mature region represented by SEQ ID NO:67.

In the present invention, example of the amino acid sequence of human BMP9 may include those containing two of the amino acid sequence of the human BMP9 mature region represented by SEQ ID NO:67 and having a disulfide bond between cysteine residues at position 73.

In the present invention, the three-dimensional structure of human BMP9 may be any structure as long as it has a structure equivalent to the naturally existing structure of human BMP9 containing the amino acid sequence represented by SEQ ID NO:66, GenBank Accession NO. NP_057288 or SEQ ID NO:67. The naturally existing structure of human BMP9 refers to the natural three-dimensional structure of human BMP9.

In the present invention, BMPRII may be a polypeptide that comprises the amino acid sequence of positions 27 to 150 corresponding to the extracellular region in the amino acid sequence represented by SEQ ID NO:70 or GenBank Accession NO. NP_001195.

In the present invention, ALK1 may be a polypeptide that comprises the amino acid sequence of positions 22 to 118 corresponding to the extracellular region in the amino acid sequence represented by SEQ ID NO:71 or GenBank Accession NO. AAH42637.

The dissociation constant (Kd value) of the antibody of the present invention can be calculated by a single-cycle kinetic method (BIAevaluation Software ver.3, manufactured by GE Healthcare) from the sensorgram obtained by using a Biacore system (manufactured by GE Healthcare).

Specifically, examples of the antibody may include the following monoclonal antibodies and antibody fragments thereof of (i) to (ii).
(i) a monoclonal antibody and an antibody fragment thereof which comprises a heavy chain (hereinbelow, referred to as H chain) of an antibody in which CDRs 1 to 3 comprising the amino acid sequences represented by SEQ ID NOs:54 to 56, respectively, and comprises a light chain (hereinbelow, referred to as L chain) of an antibody in which CDRs 1 to 3 comprising the amino acid sequences represented by SEQ ID NOs:57 to 59, respectively.
(ii) a monoclonal antibody and an antibody fragment thereof which comprises an H chain of an antibody in which CDRs 1 to 3 comprising the amino acid sequences represented by SEQ ID NOs:60 to 62, respectively, and comprises an L chain of an antibody in which CDRs 1 to 3 comprising the amino acid sequences represented by SEQ ID NOs:63 to 65, respectively.

More specifically, examples of the monoclonal antibody of the present invention may include the following monoclonal antibodies and antibody fragments thereof of (a), (b) and (c).
(a) a monoclonal antibody and an antibody fragment thereof which comprises a heavy chain variable region (hereinafter, referred to as VH) of an antibody comprising the amino acid sequence represented by SEQ ID NO:48, and comprises a light chain variable region (hereinafter, referred to as VL) of an antibody comprising the amino acid sequence represented by SEQ ID NO:51.
(b) a monoclonal antibody and an antibody fragment thereof which comprises VH of an antibody comprising the amino acid sequence represented by SEQ ID NO:49, and comprises VL of an antibody comprising the amino acid sequence represented by SEQ ID NO:52.
(c) an antibody and an antibody fragment thereof which comprises VH of an antibody comprising the amino acid sequence represented by SEQ ID NO:128, and comprises VL of an antibody comprising the amino acid sequence represented by SEQ ID NO:132.

Further, the monoclonal antibody of the present invention may include monoclonal antibodies and antibody fragments thereof that bind to an epitope identical to the epitope present in human BMP9 to which the above monoclonal antibodies bind.

Binding of the antibody or the antibody fragment thereof of the present invention to the amino acid sequence of human BMP9 or the three-dimensional structure thereof can be detected by a conventionally known immunological detection method for human BMP9 or human BMP9-expressing tissues, such as enzyme linked immunosorbent assay (ELISA) using a solid-phase antigen, or a method of examining a specific antigen and binding ability of an antibody to the specific antigen.

Examples thereof may include surface plasmon resonance using a Biacore System (manufactured by GE Healthcare) or the like, and isothermal titration calorimetry using ITC (manufactured by DKSH) or the like.

The dissociation constant (Kd value) of the antibody to the antigen can be determined by performing scatchard plot analysis or analysis in accordance with the attached document of each device using any method of ELISA, surface plasmon resonance, and isothermal titration calorimetry.

Further, the known immunoassays [Monoclonal Antibodies-Principles and practice, Third edition, Academic Press (1996), Antibodies—A Laboratory Manual, Cold Spring Harbor Laboratory (1988), Manual for monoclonal antibody experiments, Kodansha Scientific (1987)] may be used in combination for detection.

The human BMP9-expressing tissue may be any tissue as long as it expresses BMP9, and for example, blood, liver or the like.

The monoclonal antibody of the present invention may be an antibody produced by a hybridoma or a recombinant antibody produced by a transformant that is transformed with an expression vector containing a gene of the antibody.

The monoclonal antibody is characterized in that it is an antibody secreted by a single clone antibody-producing cell, and recognizes only one epitope (also called antigen determinant) and has uniform amino acid sequence (primary structure) constituting the monoclonal antibody.

Examples of the epitope include a single amino acid sequence which is recognized and bound by the monoclonal antibody, a three-dimensional structure composed of the amino acid sequence, a sugar chain-bound amino acid sequence, a three-dimensional structure composed of the sugar chain-bound amino acid sequence, or the like.

The monoclonal antibody of the present invention preferably binds to the amino acid sequence of human BMP9.

The epitope bound by the monoclonal antibody of the present invention is preferably included in the amino acid sequence of human BMP9.

The hybridoma may be, for example, obtained by preparing the above described human BMP9 as an antigen, inducing antibody-producing cells with the antigen specificity in an animal immunized with the antigen, and performing fusion of the antibody-producing cells with myeloma cells. This hybridoma is cultured or injected into an animal to develop canceration of the ascitic fluid, and the culture broth or ascitic fluid is isolated and purified, thereby obtaining an anti-BMP9 monoclonal antibody.

The animal immunized with the antigen may be any one as long as it can be used for the generation of the hybridoma, and preferably mouse, rat, hamster, chicken, rabbit or the like. Further, antibodies produced from the hybridoma that is prepared by obtaining cells having an antibody-producing ability from the animals, performing immunization of these cells in vitro, and then performing fusion of the cells with myeloma cells are also included in the antibody of the present invention.

The recombinant antibody of the present invention includes antibodies generated by recombination, such as a human chimeric antibody, a human CDR grafted antibody, a human antibody, an antibody fragment thereof or the like. The recombinant antibody having the properties of monoclonal antibody, low antigenicity, and prolonged blood half-life are preferred as a therapeutic agent. Example of the recombinant antibody may include those generated by modifying the monoclonal antibody of the present invention using a recombination technique.

The human chimeric antibody refers to an antibody consists of VH and VL of an antibody of non-human animal and a heavy chain constant region (hereinbelow, referred to as CH) and a light chain constant region (hereinbelow, referred to as CL) of a human antibody. The human chimeric antibody of the present invention is prepared by obtaining cDNA encoding VH and VL from the above described hybridoma, inserting the cDNA to each of expression vectors for animal cells having genes encoding CH and CL of a human antibody so as to construct a human chimeric antibody expression vector, and introducing this vector into animal cells for expression.

CH of the human chimeric antibody may be any one as long as it belongs to human immunoglobulins (hereinafter, referred to as hIg), preferably those belonging to hIgG class, and also, any of subclasses hIgG1, hIgG2, hIgG3 or hIgG4 belonging to hIgG class. Further, CL of the human chimeric antibody may be any one as long as it belongs to hIg, and those belonging to κ or λ class can be used.

Specific example of the human chimeric antibody of the present invention may include a chimeric antibody which comprises VH of an antibody comprising the amino acid sequence represented by SEQ ID NO:48 and comprises VL of an antibody comprising the amino acid sequence represented by SEQ ID NO:51, and also a chimeric antibody which comprises VH of an antibody comprising the amino acid sequence represented by SEQ ID NO:49 and comprises VL of an antibody comprising the amino acid sequence represented by SEQ ID NO:52.

The human CDR grafted antibody, also called humanized antibody, refers to an antibody that is generated by grafting the amino acid sequence of CDR of VH and VL of a non-human animal antibody to the proper region of VH and VL of a human antibody. The human CDR grafted antibody of the present invention can be prepared by constructing cDNA encoding the variable region (hereinbelow, referred to as V region) obtained by grafting the amino acid sequence of CDR of VH and VL of a non-human animal antibody, which is produced from the hybridoma producing a non-human animal monoclonal antibody that specifically recognizes human BMP9 and binds to the amino acid sequence of human BMP9 or the three-dimensional structure thereof, to the framework (hereinafter, referred to as FR) of VH and VL of any human antibody, inserting the cDNA to each of expression vectors for animal cells having genes encoding CH and CL of a human antibody so as to construct a human CDR-grafted antibody expression vector, and introducing this vector into animal cells for expression.

CH of the human CDR grafted antibody may be any one as long as it belongs to hIg, preferably those belonging to hIgG class, and also, any of subclasses hIgG1, hIgG2, hIgG3 or hIgG4 belonging to hIgG class. Further, CL of the human CDR grafted antibody may be any one as long as it belongs to hIg, and those belonging to κ or λ class can be used.

Specific example of the human CDR grafted antibody of the present invention may include a humanized antibody which comprises VH of an antibody in which CDR1 to 3 comprising the amino acid sequences represented by SEQ ID NOs:54 to 56 and comprises VL of an antibody in which CDR1 to 3 comprising the amino acid sequences represented by SEQ ID NOs:57 to 59, and also, a humanized antibody which comprises VH of an antibody in which CDR1 to 3 comprising the amino acid sequences represented by SEQ ID NOs:60 to 62 and comprises VL of an antibody in which CDR1 to 3 comprising the amino acid sequences represented by SEQ ID NOs:63 to 65.

Specific example of the humanized antibody of the present invention may include a humanized antibody comprising at least one of the following (a) VH and (b) VL.

(a) VH of antibody comprising an amino acid sequence of SEQ ID NO:116, or an amino acid sequence in which at least one amino acid residue selected from Gly at position 8, Leu at position 18, Gly at position 49, Asn at position 79, Leu at position 81, Ala at position 94, Val at position 95, Ala at position 99, and Arg at position 100 in the amino acid sequence of SEQ ID NO:116 is substituted with other amino acid residue.

(b) VL of antibody comprising an amino acid sequence of SEQ ID NO:118, or an amino acid sequence in which at least one amino acid residue selected from Met at position 4, Tyr at position 40, Ser at position 81, Leu at position 82, Val at position 89, and Tyr at position 91 in the amino acid sequence of SEQ ID NO:118 is substituted with other amino acid residue.

Further, VH included in the humanized antibody of the present invention is preferably the following (1) to (6).

(1) VH comprising an amino acid sequence in which Gly at position 8, Leu at position 18, Gly at position 49, Asn at position 79, Leu at position 81, Ala at position 94, Val at position 95, Ala at position 99, and Arg at position 100 in the amino acid sequence of SEQ ID NO:116 are substituted with other amino acid residues.

(2) VH comprising an amino acid sequence in which Gly at position 8, Leu at position 18, Gly at position 49, Leu at position 81, Ala at position 94, Ala at position 99, and Arg at position 100 in the amino acid sequence of SEQ ID NO:116 are substituted with other amino acid residues.

(3) VH comprising an amino acid sequence in which Gly at position 8, Leu at position 18, Gly at position 49, Asn at position 79, Ala at position 94, Ala at position 99, and Arg at position 100 in the amino acid sequence of SEQ ID NO:116 are substituted with other amino acid residues.

(4) VH comprising an amino acid sequence in which Gly at position 49, Val at position 95, Ala at position 99, and Arg at position 100 in the amino acid sequence of SEQ ID NO:116 are substituted with other amino acid residues.

(5) VH comprising an amino acid sequence in which Gly at position 8, Leu at position 18, Asn at position 79, and Arg at position 100 in the amino acid sequence of SEQ ID NO:116 are substituted with other amino acid residues.
(6) VH comprising an amino acid sequence in which Gly at position 49, Ala at position 99, and Arg at position 100 in the amino acid sequence of SEQ ID NO:116 are substituted with other amino acid residues.

Example of the amino acid sequence of VH described above may include an amino acid sequence, which is introduced with at least one modification selected from substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.

Specific example of the amino acid sequence of VH introduced with 9 modifications may include an amino acid sequence, which is introduced with substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.

Specific example of the amino acid sequence of VH introduced with 8 modifications may include the amino acid sequences of the following (1) to (9).
(1) an amino acid sequence, which is introduced with substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(2) an amino acid sequence, which is introduced with substitution of Gly with Arg at position 8, substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(3) an amino acid sequence, which is introduced with substitution of Gly with Arg at position 8, substitution of Leu with Met at position 18, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(4) an amino acid sequence, which is introduced with substitution of Gly with Arg at position 8, substitution of Leu with Met at position 18, substitution of Gly with Ala at position 49, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(5) an amino acid sequence, which is introduced with substitution of Gly with Arg at position 8, substitution of Leu with Met at position 18, substitution of Gly with Ala at position 49, substitution of Asn with Ser at position 79, substitution of Ala with Gly at position 94, substitution of Val with Ile at position 95, substitution of Ala with Thr at position 99, and substitution of Arg with Gly at position 100 in the amino acid sequence of SEQ ID NO:116.
(6) an amino acid sequence, which is introduced with substitution of Gly with Arg at position 8, substitution of Leu with Met at position 18, substitution of Gly with Ala at position 49, substitution of Asn with Ser at position 79, substitution of Leu with Val at position 81, substitution of Val with Ile at position 95, substitution of Ala with Thr at position 99, and substitution of Arg with Gly at position 100 in the amino acid sequence of SEQ ID NO:116.
(7) an amino acid sequence, which is introduced with substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Ala with Thr at position 99, and substitution of Arg with Gly at position 100 in the amino acid sequence of SEQ ID NO:116.
(8) an amino acid sequence, which is introduced with substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, and substitution of Arg with Gly at position 100 in the amino acid sequence of SEQ ID NO:116.
(9) an amino acid sequence, which is introduced with substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, and substitution of Ala with Thr at position 99 in the amino acid sequence of SEQ ID NO:116.

Specific example of the amino acid sequence of VH introduced with 7 modifications may include the amino acid sequences of the following (1) to (8).
(1) an amino acid sequence, which is introduced with substitution of Gly with Arg at position 8, substitution of Leu with Met at position 18, substitution of Gly with Ala at position 49, substitution of Leu with Val at position 81, substitution of Ala with Gly at position 94, substitution of Ala with Thr at position 99, and substitution of Arg with Gly at position 100 in the amino acid sequence of SEQ ID NO:116.
(2) an amino acid sequence, which is introduced with substitution of Gly with Arg at position 8, substitution of Leu with Met at position 18, substitution of Gly with Ala at position 49, substitution of Asn with Ser at position 79, substitution of Ala with Gly at position 94, substitution of Ala with Thr at position 99, and substitution of Arg with Gly at position 100 in the amino acid sequence of SEQ ID NO:116.
(3) an amino acid sequence, which is introduced with substitution of Gly with Arg at position 8, substitution of Leu with Met at position 18, substitution of Gly with Ala at position 49, substitution of Leu with Val at position 81, substitution of Ala with Gly at position 94, substitution of Ala with Thr at position 99, and substitution of Arg with Gly at position 100 in the amino acid sequence of SEQ ID NO:116.
(4) an amino acid sequence, which is introduced with substitution of Gly with Arg at position 8, substitution of Gly with Ala at position 49, substitution of Asn with Ser at position 79, substitution of Leu with Val at position 81, substitution of Ala with Gly at position 94, substitution of Ala with Thr at position 99, and substitution of Arg with Gly at position 100 in the amino acid sequence of SEQ ID NO:116.
(5) an amino acid sequence, which is introduced with substitution of Gly with Arg at position 8, substitution of Gly with Ala at position 49, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(6) an amino acid sequence, which is introduced with substitution of Leu with Met at position 18, substitution of Gly with Ala at position 49, substitution of Asn with Ser at position 79, substitution of Leu with Val at position 81, substitution of Ala with Gly at position 94, substitution of Ala with Thr at position 99, and substitution of Arg with Gly at position 100 in the amino acid sequence of SEQ ID NO:116.
(7) an amino acid sequence, which is introduced with substitution of Leu with Met at position 18, substitution of Gly with Ala at position 49, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.
(8) an amino acid sequence, which is introduced with substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence of SEQ ID NO:116.

Specific example of the amino acid sequence of VH introduced with 6 modifications may include the amino acid sequences of the following (1) to (7).
(1) an amino acid sequence, which is introduced with substitution of Leu with Met at position 18, substitution of Gly with Ala at position 49, substitution of Leu with Val at position 81, substitution of Ala with Gly at position 94, substitution of Ala with Thr at position 99, and substitution of Arg with Gly at position 100 in the amino acid sequence of SEQ ID NO:116.
(2) an amino acid sequence, which is introduced with substitution of Gly with Arg at position 8, substitution of Gly with Ala at position 49, substitution of Leu with Val at position 81, substitution of Ala with Gly at position 94, substitution of Ala with Thr at position 99, and substitution of Arg with Gly at position 100 in the amino acid sequence of SEQ ID NO:116.
(3) an amino acid sequence, which is introduced with substitution of Gly with Arg at position 8, substitution of Leu with Met at position 18, substitution of Leu with Val at position 81, substitution of Ala with Gly at position 94, substitution of Ala with Thr at position 99, and substitution of Arg with Gly at position 100 in the amino acid sequence of SEQ ID NO:116.
(4) an amino acid sequence, which is introduced with substitution of Gly with Arg at position 8, substitution of Leu with Met at position 18, substitution of Gly with Ala at position 49, substitution of Ala with Gly at position 94, substitution of Ala with Thr at position 99, and substitution of Arg with Gly at position 100 in the amino acid sequence of SEQ ID NO:116.
(5) an amino acid sequence, which is introduced with substitution of Gly with Arg at position 8, substitution of Leu with Met at position 18, substitution of Gly with Ala at position 49, substitution of Leu with Val at position 81, substitution of Ala with Thr at position 99, and substitution of Arg with Gly at position 100 in the amino acid sequence of SEQ ID NO:116.
(6) an amino acid sequence, which is introduced with substitution of Gly with Arg at position 8, substitution of Leu with Met at position 18, substitution of Gly with Ala at position 49, substitution of Leu with Val at position 81, substitution of Ala with Gly at position 94, and substitution of Arg with Gly at position 100 in the amino acid sequence of SEQ ID NO:116.
(7) an amino acid sequence, which is introduced with substitution of Gly with Arg at position 8, substitution of Leu with Met at position 18, substitution of Gly with Ala at position 49, substitution of Leu with Val at position 81, substitution of Ala with Gly at position 94, and substitution of Ala with Thr at position 99 in the amino acid sequence of SEQ ID NO:116.

Specific example of the amino acid sequence of VH introduced with 5 modifications may include the amino acid sequences of the following (1) to (6).
(1) an amino acid sequence, which is introduced with substitution of Gly with Ala at position 49, substitution of Leu with Val at position 81, substitution of Ala with Gly at position 94, substitution of Ala with Thr at position 99, and substitution of Arg with Gly at position 100 in the amino acid sequence of SEQ ID NO:116.
(2) an amino acid sequence, which is introduced with substitution of Gly with Arg at position 8, substitution of Leu with Met at position 18, substitution of Ala with Gly at position 94, substitution of Ala with Thr at position 99, and substitution of Arg with Gly at position 100 in the amino acid sequence of SEQ ID NO:116.
(3) an amino acid sequence, which is introduced with substitution of Leu with Met at position 18, substitution of Leu with Val at position 81, substitution of Ala with Gly at position 94, substitution of Ala with Thr at position 99, and substitution of Arg with Gly at position 100 in the amino acid sequence of SEQ ID NO:116.
(4) an amino acid sequence, which is introduced with substitution of Gly with Arg at position 8, substitution of Leu with Val at position 81, substitution of Ala with Gly at position 94, substitution of Ala with Thr at position 99, and substitution of Arg with Gly at position 100 in the amino acid sequence of SEQ ID NO:116.
(5) an amino acid sequence, which is introduced with substitution of Leu with Met at position 18, substitution of Gly with Ala at position 49, substitution of Ala with Gly at position 94, substitution of Ala with Thr at position 99, and substitution of Arg with Gly at position 100 in the amino acid sequence of SEQ ID NO:116.
(6) an amino acid sequence, which is introduced with substitution of Gly with Arg at position 8, substitution of Gly with Ala at position 49, substitution of Ala with Gly at position 94, substitution of Ala with Thr at position 99, and substitution of Arg with Gly at position 100 in the amino acid sequence of SEQ ID NO:116.

Specific example of the amino acid sequence of VH introduced with 4 modifications may include the amino acid sequences of the following (1) to (7).
(1) an amino acid sequence, which is introduced with substitution of Gly with Arg at position 8, substitution of Leu with Met at position 18, substitution of Asn with Ser at position 79, and substitution of Arg with Gly at position 100 in the amino acid sequence of SEQ ID NO:116.
(2) an amino acid sequence, which is introduced with substitution of Gly with Ala at position 49, substitution of Val with Ile at position 95, substitution of Ala with Thr at position 99, and substitution of Arg with Gly at position 100 in the amino acid sequence of SEQ ID NO:116.
(3) an amino acid sequence, which is introduced with substitution of Leu with Val at position 81, substitution of Ala with Gly at position 94, substitution of Ala with Thr at position 99, and substitution of Arg with Gly at position 100 in the amino acid sequence of SEQ ID NO:116.
(4) an amino acid sequence, which is introduced with substitution of Gly with Ala at position 49, substitution of Ala with Gly at position 94, substitution of Ala with Thr at position 99, and substitution of Arg with Gly at position 100 in the amino acid sequence of SEQ ID NO:116.

(5) an amino acid sequence, which is introduced with substitution of Gly with Ala at position 49, substitution of Leu with Val at position 81, substitution of Ala with Thr at position 99, and substitution of Arg with Gly at position 100 in the amino acid sequence of SEQ ID NO:116.

(6) an amino acid sequence, which is introduced with substitution of Gly with Ala at position 49, substitution of Leu with Val at position 81, substitution of Ala with Gly at position 94, and substitution of Arg with Gly at position 100 in the amino acid sequence of SEQ ID NO:116.

(7) an amino acid sequence, which is introduced with substitution of Gly with Ala at position 49, substitution of Leu with Val at position 81, substitution of Ala with Gly at position 94, and substitution of Ala with Thr at position 99 in the amino acid sequence of SEQ ID NO:116.

Specific example of the amino acid sequence of VH introduced with 3 modifications may include the amino acid sequences of the following (1) to (6).

(1) an amino acid sequence, which is introduced with substitution of Gly with Ala at position 49, substitution of Ala with Thr at position 99, and substitution of Arg with Gly at position 100 in the amino acid sequence of SEQ ID NO:116.

(2) an amino acid sequence, which is introduced with substitution of Gly with Ala at position 49, substitution of Leu with Val at position 81, and substitution of Arg with Gly at position 100 in the amino acid sequence of SEQ ID NO:116.

(3) an amino acid sequence, which is introduced with substitution of Gly with Ala at position 49, substitution of Ala with Gly at position 94, and substitution of Arg with Gly at position 100 in the amino acid sequence of SEQ ID NO:116.

(4) an amino acid sequence, which is introduced with substitution of Leu with Val at position 81, substitution of Ala with Gly at position 94, and substitution of Arg with Gly at position 100 in the amino acid sequence of SEQ ID NO:116.

(5) an amino acid sequence, which is introduced with substitution of Leu with Val at position 81, substitution of Ala with Thr at position 99, and substitution of Arg with Gly at position 100 in the amino acid sequence of SEQ ID NO:116.

(6) an amino acid sequence, which is introduced with substitution of Ala with Gly at position 94, substitution of Ala with Thr at position 99, and substitution of Arg with Gly at position 100 in the amino acid sequence of SEQ ID NO:116.

Specific example of the amino acid sequence of VH introduced with 2 modifications may include the amino acid sequences of the following (1) to (12).

(1) an amino acid sequence, which is introduced with substitution of Gly with Arg at position 8, and substitution of Arg with Gly at position 100 in the amino acid sequence of SEQ ID NO:116.

(2) an amino acid sequence, which is introduced with substitution of Leu with Met at position 18, and substitution of Arg with Gly at position 100 in the amino acid sequence of SEQ ID NO:116.

(3) an amino acid sequence, which is introduced with substitution of Gly with Ala at position 49, and substitution of Arg with Gly at position 100 in the amino acid sequence of SEQ ID NO:116.

(4) an amino acid sequence, which is introduced with substitution of Leu with Val at position 81, and substitution of Arg with Gly at position 100 in the amino acid sequence of SEQ ID NO:116.

(5) an amino acid sequence, which is introduced with substitution of Ala with Gly at position 94, and substitution of Arg with Gly at position 100 in the amino acid sequence of SEQ ID NO:116.

(6) an amino acid sequence, which is introduced with substitution of Ala with Thr at position 99, and substitution of Arg with Gly at position 100 in the amino acid sequence of SEQ ID NO:116.

(7) an amino acid sequence, which is introduced with substitution of Gly with Arg at position 8, and substitution of Gly with Ala at position 49 in the amino acid sequence of SEQ ID NO:116.

(8) an amino acid sequence, which is introduced with substitution of Leu with Met at position 18, and substitution of Gly with Ala at position 49 in the amino acid sequence of SEQ ID NO:116.

(9) an amino acid sequence, which is introduced with substitution of Gly with Ala at position 49, and substitution of Leu with Val at position 81 in the amino acid sequence of SEQ ID NO:116.

(10) an amino acid sequence, which is introduced with substitution of Gly with Ala at position 49, and substitution of Ala with Gly at position 94 in the amino acid sequence of SEQ ID NO:116.

(11) an amino acid sequence, which is introduced with substitution of Gly with Ala at position 49, and substitution of Ala with Thr at position 99 in the amino acid sequence of SEQ ID NO:116.

(12) an amino acid sequence, which is introduced with substitution of Gly with Ala at position 49, and substitution of Arg with Gly at position 100 in the amino acid sequence of SEQ ID NO:116.

Specific example of the amino acid sequence of VH introduced with 1 modification may include the amino acid sequences of the following (1) to (9).

(1) an amino acid sequence, which is introduced with substitution of Gly with Arg at position 8 in the amino acid sequence of SEQ ID NO:116.

(2) an amino acid sequence, which is introduced with substitution of Leu with Met at position 18 in the amino acid sequence of SEQ ID NO:116.

(3) an amino acid sequence, which is introduced with substitution of Gly with Ala at position 49 in the amino acid sequence of SEQ ID NO:116.

(4) an amino acid sequence, which is introduced with substitution of Asn with Ser at position 79 in the amino acid sequence of SEQ ID NO:116.

(5) an amino acid sequence, which is introduced with substitution of Leu with Val at position 81 in the amino acid sequence of SEQ ID NO:116.

(6) an amino acid sequence, which is introduced with substitution of Ala with Gly at position 94 in the amino acid sequence of SEQ ID NO:116.

(7) an amino acid sequence, which is introduced with substitution of Val with Ile at position 95 in the amino acid sequence of SEQ ID NO:116.

(8) an amino acid sequence, which is introduced with substitution of Ala with Thr at position 99 in the amino acid sequence of SEQ ID NO:116.

(9) an amino acid sequence, which is introduced with substitution of Arg with Gly at position 100 in the amino acid sequence of SEQ ID NO:116.

Further, VL included in the humanized antibody of the present invention is preferably the following (1) to (4).

(1) VL of antibody containing an amino acid sequence in which Met at position 4, Tyr at position 40, Ser at position 81, Leu at position 82, Val at position 89, and Tyr at position 91 in the amino acid sequence of SEQ ID NO:118 are substituted with other amino acid residues.

(2) VL of antibody containing an amino acid sequence in which Met at position 4, Ser at position 81, Leu at position 82, and Val at position 89 in the amino acid sequence of SEQ ID NO:118 are substituted with other amino acid residues.

(3) VL of antibody containing an amino acid sequence in which Tyr at position 40, Ser at position 81, and Tyr at position 91 in the amino acid sequence of SEQ ID NO:118 are substituted with other amino acid residues.

(4) VL of antibody containing an amino acid sequence in which Tyr at position 40, and Tyr at position 91 in the amino acid sequence of SEQ ID NO:118 are substituted with other amino acid residues.

Example of the amino acid sequence of VL described above may include an amino acid sequence which is introduced with at least one modification selected from substitution of Met with Leu at position 4, substitution of Tyr with Phe at position 40, substitution of Ser with Pro at position 81, substitution of Leu with Met at position 82, substitution of Val with Met at position 89, and substitution of Tyr with Phe at position 91 in the amino acid sequence of SEQ ID NO:118.

Specific example of the amino acid sequence of VL introduced with 6 modifications may include the amino acid sequence which is introduced with substitution of Met with Leu at position 4, substitution of Tyr with Phe at position 40, substitution of Ser with Pro at position 81, substitution of Leu with Met at position 82, substitution of Val with Met at position 89, and substitution of Tyr with Phe at position 91 in the amino acid sequence of SEQ ID NO:118.

Specific example of the amino acid sequence of VL introduced with 5 modifications may include the amino acid sequences of the following (1) to (6).

(1) an amino acid sequence, which is introduced with substitution of Tyr with Phe at position 40, substitution of Ser with Pro at position 81, substitution of Leu with Met at position 82, substitution of Val with Met at position 89, and substitution of Tyr with Phe at position 91 in the amino acid sequence of SEQ ID NO:118.

(2) an amino acid sequence, which is introduced with substitution of Met with Leu at position 4, substitution of Ser with Pro at position 81, substitution of Leu with Met at position 82, substitution of Val with Met at position 89, and substitution of Tyr with Phe at position 91 in the amino acid sequence of SEQ ID NO:118.

(3) an amino acid sequence, which is introduced with substitution of Met with Leu at position 4, substitution of Tyr with Phe at position 40, substitution of Leu with Met at position 82, substitution of Val with Met at position 89, and substitution of Tyr with Phe at position 91 in the amino acid sequence of SEQ ID NO:118.

(4) an amino acid sequence, which is introduced with substitution of Met with Leu at position 4, substitution of Tyr with Phe at position 40, substitution of Ser with Pro at position 81, substitution of Val with Met at position 89, and substitution of Tyr with Phe at position 91 in the amino acid sequence of SEQ ID NO:118.

(5) an amino acid sequence, which is introduced with substitution of Met with Leu at position 4, substitution of Tyr with Phe at position 40, substitution of Ser with Pro at position 81, substitution of Leu with Met at position 82, and substitution of Tyr with Phe at position 91 in the amino acid sequence of SEQ ID NO:118.

(6) an amino acid sequence, which is introduced with substitution of Met with Leu at position 4, substitution of Tyr with Phe at position 40, substitution of Ser with Pro at position 81, substitution of Leu with Met at position 82, and substitution of Val with Met at position 89 in the amino acid sequence of SEQ ID NO:118.

Specific example of the amino acid sequence of VL introduced with 4 modifications may include the amino acid sequences of the following (1) to (6).

(1) an amino acid sequence, which is introduced with substitution of Met with Leu at position 4, substitution of Ser with Pro at position 81, substitution of Leu with Met at position 82, and substitution of Val with Met at position 89 in the amino acid sequence of SEQ ID NO:118.

(2) an amino acid sequence, which is introduced with substitution of Ser with Pro at position 81, substitution of Leu with Met at position 82, substitution of Val with Met at position 89, and substitution of Tyr with Phe at position 91 in the amino acid sequence of SEQ ID NO:118.

(3) an amino acid sequence, which is introduced with substitution of Tyr with Phe at position 40, substitution of Leu with Met at position 82, substitution of Val with Met at position 89, and substitution of Tyr with Phe at position 91 in the amino acid sequence of SEQ ID NO:118.

(4) an amino acid sequence, which is introduced with substitution of Tyr with Phe at position 40, substitution of Ser with Pro at position 81, substitution of Val with Met at position 89, and substitution of Tyr with Phe at position 91 in the amino acid sequence of SEQ ID NO:118.

(5) an amino acid sequence, which is introduced with substitution of Tyr with Phe at position 40, substitution of Ser with Pro at position 81, substitution of Leu with Met at position 82, and substitution of Val with Met at position 89 in the amino acid sequence of SEQ ID NO:118.

(6) an amino acid sequence, which is introduced with substitution of Met with Leu at position 4, substitution of Ser with Pro at position 81, substitution of Leu with Met at position 82, and substitution of Val with Met at position 89 in the amino acid sequence of SEQ ID NO:118.

Specific example of the amino acid sequence of VL introduced with 3 modifications may include the amino acid sequences of the following (1) to (6).

(1) an amino acid sequence, which is introduced with substitution of Tyr with Phe at position 40, substitution of Ser with Pro at position 81, and substitution of Tyr with Phe at position 91 in the amino acid sequence of SEQ ID NO:118.

(2) an amino acid sequence, which is introduced with substitution of Tyr with Phe at position 40, substitution of Leu with Met at position 82, and substitution of Val with Met at position 89 in the amino acid sequence of SEQ ID NO:118.

(3) an amino acid sequence, which is introduced with substitution of Tyr with Phe at position 40, substitution of Leu with Met at position 82, and substitution of Tyr with Phe at position 91 in the amino acid sequence of SEQ ID NO:118.

(4) an amino acid sequence, which is introduced with substitution of Leu with Met at position 82, substitution of Val with Met at position 89, and substitution of Tyr with Phe at position 91 in the amino acid sequence of SEQ ID NO:118.

(5) an amino acid sequence, which is introduced with substitution of Ser with Pro at position 81, substitution of Val with Met at position 89, and substitution of Tyr with Phe at position 91 in the amino acid sequence of SEQ ID NO:118.

(6) an amino acid sequence, which is introduced with substitution of Ser with Pro at position 81, substitution of Leu with Met at position 82, and substitution of Val with Met at position 89 in the amino acid sequence of SEQ ID NO:118.

Specific example of the amino acid sequence of VL introduced with 2 modifications may include the amino acid sequences of the following (1) to (10).

(1) an amino acid sequence, which is introduced with substitution of Tyr with Phe at position 40, and substitution of Ser with Pro at position 81 in the amino acid sequence of SEQ ID NO:118.
(2) an amino acid sequence, which is introduced with substitution of Tyr with Phe at position 40, and substitution of Leu with Met at position 82 in the amino acid sequence of SEQ ID NO:118.
(3) an amino acid sequence, which is introduced with substitution of Tyr with Phe at position 40, and substitution of Val with Met at position 89 in the amino acid sequence of SEQ ID NO:118.
(4) an amino acid sequence, which is introduced with substitution of Tyr with Phe at position 40, and substitution of Tyr with Phe at position 91 in the amino acid sequence of SEQ ID NO:118.
(5) an amino acid sequence, which is introduced with substitution of Ser with Pro at position 81, and substitution of Leu with Met at position 82 in the amino acid sequence of SEQ ID NO:118.
(6) an amino acid sequence, which is introduced with substitution of Ser with Pro at position 81, and substitution of Val with Met at position 89 in the amino acid sequence of SEQ ID NO:118.
(7) an amino acid sequence, which is introduced with substitution of Ser with Pro at position 81, and substitution of Tyr with Phe at position 91 in the amino acid sequence of SEQ ID NO:118.
(8) an amino acid sequence, which is introduced with substitution of Leu with Met at position 82, and substitution of Val with Met at position 89 in the amino acid sequence of SEQ ID NO:118.
(9) an amino acid sequence, which is introduced with substitution of Leu with Met at position 82, and substitution of Tyr with Phe at position 91 in the amino acid sequence of SEQ ID NO:118.
(10) an amino acid sequence, which is introduced with substitution of Val with Met at position 89, and substitution of Tyr with Phe at position 91 in the amino acid sequence of SEQ ID NO:118.

Specific example of the amino acid sequence of VL introduced with 1 modification may include the amino acid sequences of the following (1) to (6).
(1) an amino acid sequence, which is introduced with substitution of Met with Leu at position 4 in the amino acid sequence of SEQ ID NO:118.
(2) an amino acid sequence, which is introduced with substitution of Tyr with Phe at position 40 in the amino acid sequence of SEQ ID NO:118.
(3) an amino acid sequence, which is introduced with substitution of Ser with Pro at position 81 in the amino acid sequence of SEQ ID NO:118.
(4) an amino acid sequence, which is introduced with substitution of Leu with Met at position 82 in the amino acid sequence of SEQ ID NO:118.
(5) an amino acid sequence, which is introduced with substitution of Val with Met at position 89 in the amino acid sequence of SEQ ID NO:118.
(6) an amino acid sequence, which is introduced with substitution of Tyr with Phe at position 91 in the amino acid sequence of SEQ ID NO:118.

Figure 11A:
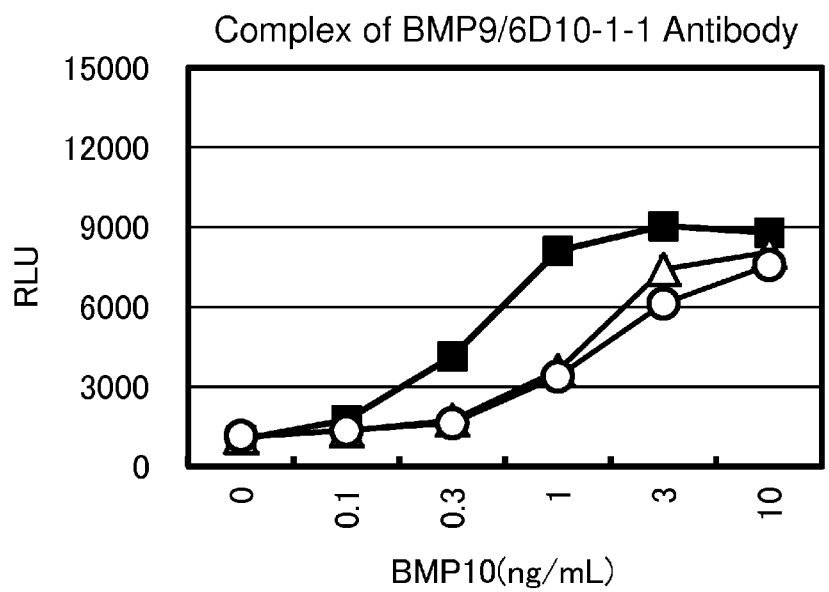
FIG. 11A shows the effect of the complex of the obtained anti-BMP9 monoclonal antibody and human BMP9 on human BMP10-dependent human ALK1 signaling, and the graph of FIG. 11A represents the result of the complex of 6D 10-1-1 antibody and human BMP9, in which the horizontal axis represents the human BMP10 concentration, and the vertical axis represents the relative luciferase unit. Single addition group of anti-BMP9 monoclonal antibody (3 μg/mL) is represented by ■, addition group of the complex of anti-BMP9 monoclonal antibody (3 μg/mL) and 2 ng/mL human BMP9 is represented by Δ, and addition group of the complex of anti-BMP9 monoclonal antibody (3 μg/mL) and 10 ng/mL human BMP9 is represented by ○.
Figure 11B:
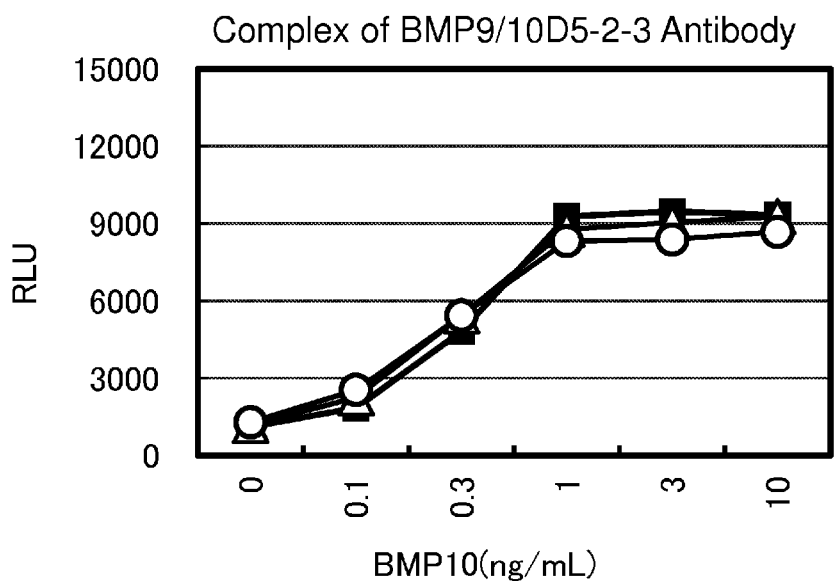
FIG. 11B shows the effect of the complex of the obtained anti-BMP9 monoclonal antibody and human BMP9 on human BMP10-dependent human ALK1 signaling, and the graph of FIG. 11B represents the result of the complex of 10D5-2-3 antibody and human BMP9, in which the horizontal axis represents the human BMP10 concentration, and the vertical axis represents the relative luciferase unit. Single addition group of anti-BMP9 monoclonal antibody (3 μg/mL) is represented by ■, addition group of the complex of anti-BMP9 monoclonal antibody (3 μg/mL) and 2 ng/mL human BMP9 is represented by Δ, and addition group of the complex of anti-BMP9 monoclonal antibody (3 μg/mL) and 10 ng/mL human BMP9 is represented by ○.

Further, specific example of the humanized antibody of the present invention may comprise a humanized antibody containing VH of the amino acid sequence of SEQ ID NO:116 and/or VL of the amino acid sequence of SEQ ID NO:118, a humanized antibody comprising VH of the amino acid sequence of SEQ ID NO:116 and/or VL of any one amino acid sequence shown in FIG. 12, a humanized antibody comprising VH of any one amino acid sequence shown in FIG. 11 and/or VL of the amino acid sequence of SEQ ID NO:118, or the like.

A human antibody means an antibody naturally existing in the human body, and also includes an antibody obtained from a human antibody phage library or a human antibody-producing transgenic animal, which is prepared based on the recent advanced techniques in genetic engineering, cell engineering and developmental engineering.

The antibody naturally existing in the human body can be prepared, for example by isolating a human peripheral blood lymphocyte, immortalizing it by infecting with EB virus or the like, and then cloning it to thereby lymphocytes capable of producing the antibody can be cultured and the antibody can be purified from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment on the phage surface having the desired antigen binding activity can be recovered from the library, using its activity to bind to an antigen-immobilized substrate as the index. The antibody fragment can be converted further into a human antibody molecule consisting of two full H chains and two full L chains by genetic engineering techniques.

A human antibody-producing transgenic animal means an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it into a complete animal. A human antibody derived from the human antibody-producing transgenic non-human animal can be prepared by obtaining a human antibody-producing hybridoma by a hybridoma preparation method usually carried out in non-human animals, culturing the obtained hybridoma and producing and accumulating the human antibody in the supernatant of the culture.

An antibody or antibody fragment thereof in which one or more amino acids are deleted, substituted, inserted or added in the amino acid sequence constituting the above antibody or antibody fragment, having activity similar to the above antibody or antibody fragment is also included in the antibody or antibody fragment of the present invention.

The number of amino acid residues which are deleted, substituted, inserted and/or added is one or more, and is not specifically limited, but it is within the range where deletion, substitution or addition is possible by known methods such as the site-directed mutagenesis [*Molecular Cloning*, Second Edition, Cold Spring Harbor Laboratory Press (1989); *Current Protocols in Molecular Biology*, John Wiley & Sons (1987-1997); *Nucleic Acids Research*, 10, 6487 (1982), *Proc. Natl. Acad. Sci. USA*, 79, 6409 (1982); *Gene*, 34, 315 (1985), *Nucleic Acids Research*, 13, 4431 (1985); *Proc. Natl. Acad. Sci. USA*, 82, 488 (1985)] or the like. For example, the number is 1 to dozens, preferably 1 to 20, more preferably 1 to 10, and most preferably 1 to 5.

Deleting, substituting, inserting and/or adding one or more amino acid residue(s) in the amino acid sequence of the above antibody means the followings. That is, it means there is deletion, substitution, insertion or addition of one or plural amino acid residues at any positions in one or plural amino acid sequences in a single sequence. Also, the deletion, substitution, insertion or addition may exist at the same case and the amino acid which is substituted, inserted or added may be either a natural type or a non-natural type.

The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.
Group A: leucine, isoleucine, norleucine, valine, norvaline, alanine, 2-aminobutanoic acid, methionine, O-methylserine, t-butylglycine, t-butylalanine, cyclohexylalanine
Group B: aspartic acid, glutamic acid, isoaspartic acid, isoglutamic acid, 2-aminoadipic acid, 2-aminosuberic acid
Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine The antibody fragment of the present invention includes Fab, F(ab')$_2$, Fab', a single-chain antibody (scFv), a dimerized V region (diabody), a disulfide-stabilized V region (dsFv), a peptide comprising CDR and the like.

An Fab is an antibody fragment having a molecular weight of about 50,000 and antigen binding activity, in which about a half of the N-terminal side of H chain and the entire L chain, among fragments obtained by treating an IgG antibody molecule with a protease, papain (cleaved at an amino acid residue at position 224 of the H chain), are bound together through a disulfide bond.

The Fab of the present invention can be obtained by treating the monoclonal antibody of the present invention with papain. Also, the Fab can be produced by inserting DNA encoding Fab of the antibody into an expression vector for prokaryote or an expression vector for eukaryote, and introducing the vector into a prokaryote or an eukaryote to express the Fab.

An F(ab')$_2$ is an antibody fragment having a molecular weight of about 100,000 and having antigen binding activity and comprising two Fab regions which are bound in the hinge portion obtained by digesting the lower part of disulfide bonds in the hinge region of IgG with an enzyme, pepsin.

The F(ab')$_2$ of the present invention can be obtained by treating the monoclonal antibody of the present invention with pepsin. Also, the F(ab')$_2$ can be produced by binding Fab' described below via a thioether bond or a disulfide bond.

An Fab' is an antibody fragment having a molecular weight of about 50,000 and antigen binding activity, in which a disulfide bond at the hinge region of the above F(ab')$_2$ is cleaved. The Fab' of the present invention can be obtained by treating F(ab')$_2$ of the present invention with a reducing agent, such as dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which a VH and a VL are linked using an appropriate peptide linker (hereinafter referred to as "P") and is an antibody fragment having antigen binding activity.

The scFv of the present invention can be produced by obtaining cDNAs encoding VH and VL of the monoclonal antibody, constructing a DNA encoding the scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, is an antibody fragment having divalent antigen binding activity. In the divalent antigen binding activity, two antigens may be the same or different.

The diabody of the present invention can be produced by obtaining cDNAs encoding VH and VL of the monoclonal antibody of the present invention, constructing DNA encoding scFv so that the length of the amino acid sequence of the peptide linker is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a conformation prediction of the antibody in accordance with a known methods [*Protein Engineering*, 7, 697 (1994)].

The dsFv of the present invention can be produced by obtaining cDNAs encoding VH and VL of the monoclonal antibody of the present invention, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one or more regions of CDRs of VH or VL. Peptides comprising plural CDRs can be connected directly or via an appropriate peptide linker.

The peptide comprising CDR of the present invention can be produced by constructing DNAs encoding CDRs of VH and VL of the monoclonal antibody of the present invention, inserting the DNAs into an expression vector for prokaryote or an expression vector for eukaryote, and then introducing the expression vector into a prokaryote or eukaryote to express the peptide. The peptide comprising CDRs can also be produced by a chemical synthesis method such as Fmoc method or tBoc method.

A monoclonal antibody of the present invention includes an antibody derivative in which the monoclonal antibody or the antibody fragment of the present invention is chemically or genetically bound to a radioisotope, a low-molecular weight agent, a high-molecular weight agent, a protein or the like. When the antibody derivative is used as a method for detection, a method for quantification, an agent for detection or an agent for quantification, an agent binding to the monoclonal antibody or the antibody fragment thereof of the present invention includes a label which is used for a usual method for immunological detection or determination.

The antibody derivative of the present invention can be produced by conjugating a radioisotope, a low-molecular-weight agent, a high-molecular-weight agent, a protein or the like to the N-terminal side or C-terminal side of an H chain or an L chain, adequate substituent or sidechain, sugarchain, and the like of the monoclonal antibody or the antibody fragment thereof or the present invention using chemical methods [*Kotai Kogaku Nyumon*, published by Chij in Shokan (1994)].

Also, the antibody derivative of the present invention can be genetically produced by linking a DNA encoding the monoclonal antibody or the antibody fragment of the present invention to other DNA encoding a protein to be conjugated, inserting the DNA into an expression vector, and introducing the expression vector into an appropriate host cell.

The radioisotopes include $^{131}$I, $^{125}$I, $^{90}$Y, $^{64}$Cu, $^{199}$Tc, $^{77}$Lu, $^{211}$At and the like. The radioisotope can be directly conjugated with the antibody by Chloramine-T method or the like. Also, a substance chelating the radioisotope can be conjugated with the antibody. The chelating agent includes 1-isothiocyanatobenzyl-3-methyldiethylene-triaminepentaacetic acid (MX-DTPA) and the like.

The low-molecular-weight agent includes, for example, a luminescent substance such as acridinium ester, rofin or the like, or a fluorescent substance such as fluorescein isothiocyanate (FITC), tetramethylrhodamine isothiocyanate (RITC) or the like.

The method for conjugating the low-molecular-weight agent with the antibody include a method in which the agent and an amino group of the antibody are conjugated via glutaraldehyde, a method in which an amino group of the agent and a carboxyl group of the antibody are conjugated via water-soluble carbodiimide, and the like.

The high-molecular-weight agents include polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like. By binding these high-molecular-weight compounds to the antibody or antibody fragment, the following effects are expected: (1) improvement of stability against various chemical, physical or biological factors, (2) remarkable prolongation of half life in blood, (3) depletion of immunogenicity or suppression of antibody production, and the like [*Bioconjugate Drug*, Hirokawa Shoten (1993)]. Examples of the methods for conjugating PEG to the antibody include a method for reacting an antibody with a PEG-modifying reagent [*Bioconjugate Drug*, Hirokawa Shoten (1993)]. The PEG-modifying reagents include a modifying agent for ϵ-amino group of lysine (Japanese Published Unexamined Patent Application No. 178926/86), a modifying agent for a carboxyl group of aspartic acid and glutamic acid (Japanese Published Unexamined Patent Application No. 23587/81), a modifying agent for a guanidino group of arginine (Japanese Published Unexamined Patent Application No. 117920/90) and the like.

The protein includes, for example, an enzyme such as alkaline phosphatase, peroxidase, luciferase or the like.

Further, the present invention relates to a therapeutic agent comprising the monoclonal antibody or the antibody fragment thereof of the present invention as an active ingredient for the treatment of diseases accompanying BMP9-involved anemia.

The diseases accompanying BMP9-involved anemia may include primary anemia caused by disorders in the blood or hematopoietic functions and secondary anemia caused by other diseases. Primary anemia includes iron-deficiency anemia, megaloblastic anemia, hemolytic anemia, aplastic anemia or the like, and secondary anemia includes renal diseases, infections (tuberculosis, infective endocarditis, hepatic abscess, etc.), collagen diseases (chronic rheumatoid arthritis, systemic erythematosus, etc.), malignant diseases such as cancer, liver diseases, endocrine diseases, or the like.

Examples of the cancer may include blood cancer, breast cancer, uterine cancer, colorectal cancer, esophageal cancer, gastric cancer, ovarian cancer, lung cancer, renal cancer, rectal cancer, thyroid cancer, uterine cervix cancer, small intestinal cancer, prostate cancer, pancreatic cancer or the like, and preferably, blood cancer, esophageal cancer, gastric cancer, colorectal cancer, liver cancer or prostate cancer.

Examples of the blood cancer may include acute myeloid leukemia (AML), chronic myeloid leukemia (CML), myelodysplasticsyndromes (MDS), multiple myeloma, cutaneous T cell lymphoma (CTCL), peripheral T-cell lymphoma (PTCL), anaplastic large cell lymphoma (ALCL), acute lymphocytic leukemia (ALL), chronic lymphocytic leukemia (CLL), other lymphoid leukemia, NK cell lymphoma, Hodgkin lymphoma, non-Hodgkin's lymphoma such as Burkitt's lymphoma, or the like.

Examples of the liver disease may include chronic hepatitis, cirrhosis, hepatic insufficiency or the like, and examples of endocrine disease may include hypothyroidism, hypoadrenocorticism, hypopituitarism, hyperparathyroidism or the like.

The therapeutic agent of the present invention comprises the above described monoclonal antibody or the antibody fragment thereof of the present invention as an active ingredient.

The therapeutic agent including the antibody or the antibody fragment thereof of the present invention, or derivative thereof may comprise only the antibody or the antibody fragment thereof, or the derivative thereof as an active ingredient. It is preferable that the therapeutic agent is provided as a pharmaceutical preparation produced by mixing it with one or more pharmaceutically acceptable carriers in accordance with an appropriate method well known in the technical field of pharmaceutics.

Preferably, the therapeutic agent is administered via the route that is most effective for the treatment. Examples of the route may include oral administration and parenteral administration, such as buccal, tracheal, rectal, subcutaneous, intramuscular or intravenous administration, and intravenous or subcutaneous administration is preferred.

Examples of the dosage form includes sprays, capsules, tablets, powders, granules, syrups, emulsions, suppositories, injections, ointments, tapes or the like.

Although the dose or the frequency of administration varies depending on the desired therapeutic effect, administration method, treatment period, age, body weight or the like, it is usually administered at a daily dose of 10 µg/kg to 10 mg/kg per adult.

Further, the present invention relates to a method for immunologically detecting or measuring BMP9, including the monoclonal antibody or the antibody fragment thereof that specifically recognizes and binds to the amino acid sequence of BMP9 or three-dimensional structure thereof, as an active ingredient.

In the present invention, the method for detecting or measuring the amount of BMP9 may be any known method, for example, an immunological detecting or measuring method.

The immunological detecting or measuring method is a method for detecting or determining the amount of an antibody or an antigen using a labeled antigen or antibody. Examples of the immunological detecting or measuring method include a radioactive substance-labeled immunoantibody method (RIA), an enzyme immunoassay (EIA or ELISA), a fluorescent immunoassay (FIA), a luminescent immunoassay, a Western blotting method, a physicochemical method or the like.

Hereinafter, a method for preparing the antibody of the present invention, a method for treating the disease and a method for diagnosing the disease will be described in detail.

1. Preparation Method of Monoclonal Antibody (1) Preparation of Antigen

BMP9 or tissues expressing BMP9 as an antigen can be obtained by introducing an expression vector comprising cDNA encoding a full length of BMP9 or a partial length thereof into *Escherichia coli*, yeast, an insect cell, an animal cell or the like. In addition, BMP9 can be purified and obtained from human tissues or the like which express a large amount of BMP9, and such tissue or the like can be directly allowed to use as antigens. Furthermore, a synthetic peptide having a partial sequence of the BMP9 can be prepared by a chemical synthesis method such as Fmoc method or tBoc method, and used as an antigen.

BMP9 used in the present invention can be produced, for example, by expressing a DNA encoding BMP9 in a host cell using a method described in Molecular Cloning, A Laboratory Manual, Second Edition, Cold Spring Harbor Laboratory Press (1989) or Current Protocols in molecular Biology, John Wiley&Sons (1987-1997) or the like according to the following method.

First, a recombinant vector is prepared by inserting a full length cDNA comprising the region encoding BMP9 into downstream of a promoter of an appropriate expression vector. A DNA fragment having an appropriate length containing a region encoding the polypeptide, prepared based on the full length cDNA, may be used instead of the above full-length cDNA. Subsequently, a transformant producing polypeptide can be obtained by introducing the recombinant vector into a host cell suitable for the expression vector.

The expression vector may be any one, as long as it can replicate autonomously in the host cell to be used, or it can be integrated into a chromosome including an appropriate promoter at such a position that the DNA encoding the polypeptide can be transcribed.

The host cell may be any one, as long as it can express the desired gene, such as a microorganism belonging to the genera *Escherichia*, including *Escherichia coli*, yeast, an insect cell, an animal cell or the like.

When a prokaryote such as *Escherichia coli* is used as the host cell, it is preferred that the recombinant vector is autonomously replicable in the prokaryote and comprises a promoter, a ribosome binding sequence, the DNA encoding BMP9, and a transcription termination sequence. The recombinant vector is not necessary to have a transcription termination sequence, but a transcription termination sequence is preferably set just subsequent to the structural gene. The recombinant vector may further comprise a gene regulating the promoter.

The recombinant vector is preferably a plasmid in which the space between Shine-Dalgarno sequence (hereinafter, referred to as SD sequence), which is the ribosome binding sequence, and the initiation codon is adjusted to an appropriate distance (for example, 6 to 18 nucleotides).

Furthermore, the base sequence of the DNA encoding BMP9 can be substituted with another base so as to be a codon suitable for expressing in a host cell, thereby improve the productivity of the desired BMP9.

Any expression vector can be used, as long as it can function in the host cell to be used, and exemplified by pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [Agricultural Biological Chemistry, 48, 669 (1984)], pLSA1[AgricBiol. Chem., 53, 277 (1989)], pGEL1 [Proc. Natl. Acad. Sci. USA, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. Nos. 4,686,191, 4,939,094, 5160735), pSupex, pUB110, pTP5, pC194, pEG400 [J. Bacteriol., 172, 2392 (1990)], pGEX (manufactured by Pharmacia), pET system (manufactured by Novagen), pME18SFL3 or the like.

Any promoter can be used, as long as it can function in the host cell to be used. Examples thereof may include promoters derived from *Escherichia coli*, phage or the like, such as a trp promoter (Ptrp), a lac promoter, a PL promoter, a PR promoter, a T7 promoter or the like. Also, artificially designed and modified promoters, such as a promoter in which two Ptrp promoters are tandemly linked, a tac promoter, a lacT7 promoter, a letI promoter or the like, can be used.

Examples of the host cell may include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α or the like.

Any method of introducing the recombinant vector into the host cell can be used, as long as it is a method for introducing DNA into the host cell, and examples thereof may include a method using a calcium ion [Proc. Natl. Acad. Sci. USA, 69, 2110 (1972), Gene, 17, 107 (1982), Molecular&General Genetics, 168, 111 (1979)].

When an animal cell is used as the host cell, any expression vector can be used, as long as it can function in the animal cell. Examples thereof may include pcDNAI, pcDM8 (manufactured by Funakoshi), pAGE107 [Japanese Published Unexamined Patent Application No. 22979/91; Cytotechnology, 3, 133 (1990)], pAS3-3 (Japanese Published Unexamined Patent Application No. 227075/90), pCDM8 [Nature, 329, 840, (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (WO 97/10354), or the like.

Any promoter can be used, as long as it can function in an animal cell. Examples thereof may include a promoter of immediate early (IE) gene of cytomegalovirus (CMV), an SV40 early promoter, a promoter of retrovirus, a metallothionein promoter, a heat shock promoter, an SRa promoter, a Molony murine leukemia virus promoter or enhancer, or the like. Also, the enhancer of the IE gene of human CMV can be used together with the promoter.

Examples of the host cell may include human Namalwa leukemia cell, monkey COS cell, Chinese hamster ovary (CHO) cell (Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cellgenetics, Appendix I, II (pp. 883-900)), CHO/DG44, CHO-K1 (ATCC accession NO: CCL-61), DUkXB11 (ATCC accession NO: CCL-9096), Pro-5 (ATCC accession NO: CCL-1781), CHO-S (Life Technologies, Cat#11619), Pro-3, rat myeloma cell YB2/3HL.P2.G11.16Ag.20 (also called as YB2/0), mouse myeloma cell NS0, mouse myeloma cell 5P2/0-Ag14, Syrian hamster cell BHK or HBT5637 (Japanese Published Unexamined Patent Application No. 299/88), or the like.

Any introduction method of the recombinant vector into the host cell can be used, as long as it is a method for introducing DNA into an animal cell, and examples thereof may include electroporation [Cytotechnology, 3, 133 (1990)], a calcium phosphate method (Japanese Published Unexamined Patent Application No. 227075/90), a lipofection method [Proc. Natl. Acad. Sci. USA, 84, 7413 (1987)], or the like.

BMP9 can be produced by culturing the transformant derived from a microorganism, an animal cell or the like having a recombinant vector including the DNA encoding BMP9 in a medium to form and accumulate BMP9 in the culture, and recovering it from the culture. The method for culturing the transformant in the medium is carried out according to the usual method used in culturing of hosts.

When BMP9 is expressed in a cell derived from eukaryote, BMP9 to which sugars or sugar chains bind can be obtained. When a microorganism transformed with a recombinant vector containing an inducible promoter is cultured, an inducer can be added to the medium, if necessary. For example, isopropyl-β-D-thiogalactopyranoside or the like can be added to the medium when a microorganism transformed with a recombinant vector using a lac promoter is cultured; or indoleacrylic acid or the like can be added thereto when a microorganism transformed with a recombinant vector using a trp promoter is cultured.

When a transformant obtained using an animal cell as the host cell is cultured, the medium includes generally used RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], 199 medium [Proc. Soc. Exp. Biol. Med., 73, 1 (1950)], Iscove's modified Dulbecco's medium (IMDM), the media supplemented with fetal bovine serum (FBS), etc., or the like. Culture is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Regarding the expression method of the gene encoding BMP9, in addition to direct expression, secretory production, fusion protein expression or the like [Molecular Cloning, A Laboratory Manual, Second Edition, Cold Spring Harbor Laboratory Press (1989)] can be carried out.

The process for producing BMP9 includes a method of intracellular expression in a host cell, a method of extracellular secretion from a host cell, a method of producing it on a host cell outer membrane, or the like. The appropriate method can be selected by changing the host cell used or the structure of the BMP9 produced.

When BMP9 is produced in a host cell or on a host cell membrane outer membrane, BMP9 can be positively secreted extracellularly in accordance with the method of Paulson et al. [J. Biol. Chem., 264, 17619 (1989)], the method of Lowe et al. [Proc. Natl. Acad. Sci. USA, 86, 8227 (1989), Genes Develop., 4, 1288 (1990)], the methods described in Japanese Published Unexamined Patent Application No. 336963/93 and WO 94/23021, or the like.

Also, the production amount of BMP9 can be increased by a gene amplification system using a dihydrofolate reductase gene (Japanese Published Unexamined Patent Application No. 227075/90). The resulting BMP9 can be isolated and purified, for example, as follows. When BMP9 is intracellularly expressed in a dissolved state, the cells after culturing are recovered by centrifugation, suspended in an aqueous buffer and then disrupted using a ultrasonicator, French press, Manton Gaulin homogenizer, dynomill or the like to obtain a cell-free extract.

The cell-free extract is centrifuged to obtain a supernatant, and a purified preparation can be obtained by subjecting the supernatant to a general protein isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; or the like which may be used alone or in combination.

When BMP9 is expressed intracellularly by forming an inclusion body, the cells are recovered, disrupted and centrifuged in the same manner, and the inclusion body of BMP9 are recovered as a precipitation fraction. The recovered inclusion body of the BMP9 protein is solubilized with a protein denaturing agent. The protein is made into a normal three-dimensional structure by diluting or dialyzing the solubilized solution, and then a purified preparation of polypeptide is obtained by the same isolation purification method as above.

When BMP9 or the derivative such as a glycosylated product is secreted extracellularly, BMP9 or the derivative such as a glycosylated product can be recovered from the culture supernatant. The culture is treated by a method such as centrifugation in the same manner as above to obtain a soluble fraction, and a purified preparation can be obtained from the soluble fraction by the same isolation purification method as above.

Also, BMP9 used in the present invention can be produced by a chemical synthesis method, such as Fmoc method or tBoc method. Also, it can be chemically synthesized using a peptide synthesizer manufactured by Advanced ChemTech, PerkinElmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat, hamster or the like which is 3 to 20-week-old is immunized with the antigen prepared in the above (1), and antibody-producing cells within the spleen, lymph node or peripheral blood of the animal are collected. Also, when the increase of a sufficient antibody titer in the above animal is not recognized due to low immunogenecity, a BMP9 knockout mouse may be used as an animal to be immunized.

The immunization is carried out by administering the antigen to the animal through subcutaneous, intravenous or intraperitoneal injection together with an appropriate adjuvant such as complete Freund's adjuvant, combination of aluminum hydroxide gel with pertussis vaccine, or the like. When the antigen is a partial peptide, a conjugate is produced with a carrier protein such as BSA (bovine serum albumin), KLH (keyhole limpet hemocyanin) or the like, which is used as the antigen.

The administration of the antigen is carried out 2 to 10 times every one week or every two weeks after the first administration. On the $3^{rd}$ to $7^{th}$ day after each administration, a blood sample is collected from the venous plexus in ocular fundus, the antibody titer of the serum is tested by enzyme immunoassay [Antibodies—A Laboratory Manual, Cold Spring Harbor Laboratory (1988)] or the like. An animal showing a sufficient antibody titer in their sera against the antigen used for the immunization is used as the source of antibody-producing cells for fusion.

Three to seven days after final administration of the antigen, tissue containing the antibody-producing cells such as the spleen is excised from the immunized animal to collect the antibody-producing cells. When the spleen cells are used, the spleen is cut out and loosened, followed by centrifugation. Then, antibody-producing cells for fusion are obtained by removing erythrocytes.

(3) Preparation of Myeloma Cell

An established cell line obtained from mouse is used as myeloma cells. Examples thereof may include 8-azaguanine-resistant mouse (derived from Balb/C) myeloma cell line P3-X63Ag8-U1 (P3-U1) [Current Topics in Microbiology and Immunology, 18, 1 (1978)], P3-NS1/1Ag41(NS-1) [European J. Immunology, 6, 511 (1976)], SP2/0-Ag14(SP-2) [Nature, 276, 269 (1978)], P3-X63-Ag8653(653) [J. Immunology, 123, 1548 (1979)], P3-X63-Ag8(X63) [Nature, 256, 495 (1975)] or the like.

The myeloma cells are subcultured in a normal medium [a RPMI1640 medium containing glutamine, 2-mercaptoethanol, gentamicin, FBS and 8-azaguanine] and they are subcultured in the normal medium 3 to 4 days before cell fusion to ensure the cell number of $2 \times 10^7$ or more on the day for fusion.

(4) Cell Fusion and Preparation of Hybridoma for Producing Monoclonal Antibody

The antibody-producing cells for fusion obtained by the above (2) and myeloma cells obtained by the above (3) are sufficiently washed with a Minimum Essential Medium (MEM) or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells:the myeloma cells=5 to 10:1, followed by centrifugation. Then, the supernatant is discarded.

The precipitated cell group is sufficiently loosened. The mixture of polyethylene glycol-1000 (PEG-1000), MEM and dimethylsulfoxide is added to the cell under stirring at 37° C. In addition, 1 to 2 mL of MEM medium is added several times every one or two minutes, and MEM is added to give a total volume of 50 mL. After centrifugation, the supernatant is discarded. After the precipitated cells are gently loosened, the antibody-producing cells for fusion are gently suspended in HAT medium [a normal medium containing hypoxanthine, thymidine and aminopterin]. The suspension is cultured in a 5% $CO_2$ incubator for 7 to 14 days at 37° C.

After the culturing, a portion of the culture supernatant is sampled and a cell group which is reactive to an antigen containing BMP9 and is not reactive to an antigen containing no BMP9 is selected by binding assay as described below. Then, cloning is carried out twice by a limiting dilution method [primarily, HT medium (HAT medium from which aminopterin is removed) is used, and secondarily, the normal medium is used], and a hybridoma which stably shows a high antibody titer is selected as the monoclonal antibody-producing hybridoma.

(5) Preparation of Purified Monoclonal Antibody

The hybridoma cells producing monoclonal antibodies obtained by the above (4) are administered by intraperitoneal injection into 8 to 10-week-old mice or nude mice treated with pristane [0.5 mL of 2,6,10,14-tetramethylpentadecane (pristane) is intraperitoneally administered, followed by feeding for 2 weeks]. The hybridoma develops ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained by the above (4) is cultured in RPMI1640 medium containing 10% FBS or the like and the supernatant is removed by centrifugation, followed by suspending in Hybridoma-SFM medium and culturing for 3 to 7 days. The purified monoclonal antibody can be obtained by centrifuging the obtained cell suspension, followed by purification of the resulting supernatant with Protein A column or Protein G column to collect the IgG fractions. Additionally, Hybridoma-SFM medium can contain 5% DIGO GF21.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using an enzyme immunoassay method and kinetic analysis with Biacore.

(6-a) Binding Assay

As the antigen, a gene-introduced cell obtained by introducing an expression vector comprising a cDNA encoding BMP9 obtained in (1) into *Escherichia coli*, yeast, an insect cell, an animal cell or the like, a recombinant protein, or a purified polypeptide or partial peptide obtained from a human tissue is used. When the antigen is a partial peptide, a conjugate is prepared with a carrier protein such as BSA or KLH, which can be used.

After making these antigens into a solid layer by dispensing them in a 96-well plate, a substance to be tested such as serum, a culture supernatant of a hybridoma or a purified monoclonal antibody is dispensed therein as the primary antibody and allowed to react. After thoroughly washing with PBS, PBS-Tween or the like, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction appropriate to the label of the secondary antibody is carried out to select a monoclonal antibody which specifically reacts with the antigen.

In addition, the monoclonal antibody of the present invention can be obtained by adding a subject antibody to the above binding assay system to allow to react. Namely, a monoclonal antibody which competes with the obtained monoclonal antibody in the binding of an amino acid sequence of BMP9 or a three-dimensional structure thereof can be obtained by screening an antibody which inhibits the binding of the monoclonal antibody upon adding to the subject antibody.

Furthermore, an antibody which binds to the same epitope recognized by the monoclonal antibody of the present invention can be obtained by identifying an epitope of the antibody obtained by the above binding assay system, preparing a partial synthetic peptide of the epitope or a synthetic peptide which mimics the three-dimentional structure of the epitope, and immunizing with the peptide.

(6-b) Kinetic Analysis with Biacore

The kinetics between an antigen and a test substance is measured using Biacore T100, and then the results are analyzed using analysis software accompanied with the apparatus. After anti-mouse IgG antibody is immobilized onto to a CM 5 sensor chip by an amine coupling method, a test substance such as a culture supernatant of a hybridoma, a purified monoclonal antibody or the like is allowed to flow and bind at an appropriate amount, and an antigen at various known concentrations is further allowed to flow. Then, the association and dissociation are measured.

Using the obtained data and the software accompanied with the apparatus, the kinetics analysis is carried out using the 1:1 binding model to obtain various parameters. Otherwise, after human BMP9 is immobilized onto the sensor chip by an amine coupling method, a purified monoclonal antibody is allowed to flow at various known concentrations followed by measuring the association and dissociation. Using the obtained data and the software accompanied with the apparatus, the kinetics analysis is carried out using a bivalent binding model to obtain various parameters.

2. Preparation of Recombinant Antibody

As preparation examples of recombinant antibodies, processes for producing a human chimeric antibody and a human CDR-grafted antibody are shown below.

(1) Construction of Vector for Recombinant Antibody Expression

A vector for recombinant antibody expression is an expression vector for animal cell into which DNAs encoding CH and CL of a human antibody have been inserted, and is constructed by cloning each of DNAs encoding CH and CL of a human antibody into an expression vector for animal cell.

The constant region (hereinafter, referred to as C region) of a human antibody may be CH and CL of any human antibody. Examples include CH of γ1 subclass and CL of κ class of human antibody, or the like. As the DNAs encoding CH and CL of a human antibody, the cDNA may be generally used and a chromosomal DNA composed of an exon and an intron can be also used.

As the expression vector for animal cell, any expression vector can be used, as long as a gene encoding the C region of a human antibody can be inserted thereinto and expressed therein. Examples thereof include pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] or the like.

Examples of a promoter and an enhancer used for an expression vector for animal cell include an SV40 early promoter [J. Biochem., 101, 1307 (1987)], a Moloney mouse leukemia virus LTR [Biochem. Biophys. Res. Commun., 149, 960 (1987)], an immunoglobulin H chain promoter [Cell, 41, 479 (1985)], an enhancer [Cell, 33, 717 (1983)] or the like.

As the vector for recombinant antibody expression, a type of the vector for recombinant antibody expression in which both of antibody H and L chains exist on the same vector (tandem type) [J. Immunol. Methods, 167, 271 (1994)] may be used, in terms of easiness of construction of a vector for recombinant antibody expression, easiness of introduction into animal cells, and balance between the expression levels of antibody H and L chains in animal cells, and a type in which antibody H and L chains exist on separate vectors may be also used. Examples of the tandem type of the vector for recombinant antibody expression include pKANTEX93 (WO 97/10354), pEE18 [Hybridoma, 17, 559 (1998)], or the like.

(2) Acquisition of cDNA Encoding V Region of Antibody Derived from Non-Human Animal and Analysis of Amino Acid Sequence Acquisition of cDNAs encoding VH and VL of a non-human antibody and analysis of amino acid sequence can be carried out as follows.

mRNA is extracted from hybridoma cells producing a non-human antibody to synthesize cDNA. The synthesized cDNA is cloned into a vector such as a phage or a plasmid, to prepare a cDNA library.

Each of a recombinant phage or recombinant plasmid containing cDNA encoding VH or VL is isolated from the library using DNA encoding the C region or V region of a mouse antibody as the probe. The full length of the base sequences of VH and VL of a mouse antibody of interest on the recombinant phage or recombinant plasmid are determined, and the full length of the amino acid sequences of VH and VL are deduced from the base sequences, respectively.

Examples of the non-human animal for preparing a hybridoma cell which produces a non-human antibody include mouse, rat, hamster, rabbit or the like. Any animals can be used as long as a hybridoma cell can be produced therefrom.

Total RNA can be prepared from a hybridoma cell using a guanidine thiocyanate-cesium trifluoroacetate method [Methods in Enzymol., 154, 3 (1987)], or a kit such as RNA easy kit (manufactured by Qiagen) or the like.

mRNA can be prepared from total RNA using an oligo (dT) immobilized cellulose column method [Molecular Cloning, A Laboratory Manual, Second Edition, Cold Spring Harbor Laboratory Press (1989)], a method using a kit such as Oligo-dT30 <Super> mRNA Purification Kit (manufactured by Takara Bio) or the like. In addition, mRNA can be prepared from hybridoma cells using a kit such as a Fast Track mRNA Isolation kit (manufactured by Invitrogen), a QuickPrep mRNA Purification Kit (manufactured by Pharmacia) or the like.

Examples of the method for synthesizing cDNA and preparing a cDNA library include known methods [Molecular Cloning, A Laboratory Manual, Second Edition, Cold Spring Harbor Laboratory Press (1989), Current Protocols in Molecular Biology, Supplement 1, John Wiley & Sons (1987-1997)], a method using a kit such as a Super Script Plasmid System for cDNA Synthesis and Plasmid Cloning (manufactured by Invitrogen), a ZAP-cDNA Synthesis Kit (manufactured by Stratagene), or the like.

The vector for preparing a cDNA library, into which cDNA synthesized using mRNA extracted from a hybridoma cell as the template is inserted, may be any vector, as long as the cDNA can be inserted thereto. Examples thereof include ZAP ExPress [Strategies, 5, 58 (1992)], pBluescript II SK(+) [Nucleic Acids Research, 17, 9494 (1989)], λZAPII (manufactured by Stratagene), λgt10 and λgt11 [DNA Cloning: A Practical Approach, I, 49 (1985)], Lambda BlueMid (manufactured by Clontech), λExCell, pT7T3-18U (manufactured by Pharmacia), pcD2 [Mol. Cell. Biol., 3, 280 (1983)], pUC18 [Gene, 33, 103 (1985)], or the like.

Any *Escherichia coli* for introducing the cDNA library constructed by a phage or plasmid vector may be used, as long as the cDNA library can be introduced, expressed and maintained. Examples thereof include XL1-Blue MRF [Strategies, 5, 81 (1992)], C600 [Genetics, 39, 440 (1954)], Y1088 and Y1090 [Science, 222: 778 (1983)], NM522 [J. Mol. Biol., 166, 1 (1983)], K802 [J. Mol. Biol., 16, 118 (1966)], JM105 [Gene, 38, 275 (1985)], or the like.

A colony hybridization or plaque hybridization method using an isotope- or fluorescence-labeled probe [Molecular Cloning, A Laboratory Manual, Second Edition, Cold Spring Harbor Laboratory Press (1989)] may be used for selecting cDNA clones encoding VH or VL of a non-human antibody or the like from the cDNA library.

Also, the cDNA encoding VH or VL can be prepared through polymerase chain reaction [hereinafter, referred to as "PCR"; Molecular Cloning, A Laboratory Manual, Second Edition, Cold Spring Harbor Laboratory Press (1989), Current Protocols in molecular Biology, Supplement 1, John Wiley&Sons (1987-1997)] by preparing primers and using cDNA prepared from mRNA or a cDNA library as the template.

The base sequence of the cDNA can be determined by digesting the cDNA selected with appropriate restriction enzymes or the like, cloning the fragments into a plasmid such as pBluescript SK(–) (manufactured by Stratagene), carrying out a sequence analyzing method usually used. For example, the sequence analyzing method is carried out by using an automatic nucleotide sequence analyzer such as ABI PRISM3700 (manufactured by PE Biosystems) or A.L.F. DNA sequencer (manufactured by Pharmacia) after reaction such as the dideoxy method [Proc. Natl. Acad. Sci. USA, 74, 5463 (1977)].

Whether the obtained cDNAs encode the full amino acid sequences of VH and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [A.L.F. DNA sequencer, US Dept. Health and Human Services (1991)].

With respect to the full amino acid sequences of VH and VL of the antibody containing a secretory signal sequence, the length of the secretory signal sequence and N-terminal amino acid sequence can be estimated by comparing them with the full length of the amino acid sequences of VH and VL of known antibodies [A.L.F. DNA sequencer, US Dept. Health and Human Services (1991)], and furthermore the subgroup to which they belong can be determined. In addition, the amino acid sequence of each CDR of VH and VL can be determined by comparing them with the amino acid sequences of VH and VL of known antibodies [A.L.F. DNA sequencer, US Dept. Health and Human Services (1991)].

Moreover, the novelty of the full length of the amino acid sequence of VH and VL can be examined by carrying out a homology search with sequences in any database, for example, SWISS-PROT, PIR-Protein or the like using the obtained full length of the amino acid sequences of VH and VL, for example, according to the BLAST method [J. Mol. Biol., 215, 403 (1990)] or the like.

(3) Construction of Vector for Human Chimeric Antibody Expression cDNA encoding each of VH and VL of antibody of non-human animal is cloned in the upstream of genes encoding CH or CL of human antibody of vector for expression of recombinant antibody mentioned in the above (1), thereby constructing a vector for human chimeric antibody expression.

In order to ligate the 3'-terminus of cDNA encoding VH or VL of antibody of non-human animal and the 5'-terminus of CH or CL of human antibody, each cDNA encoding VH and VL is prepared so as to encodes appropriate amino acids encoded by a base sequence of a linkage portion and designed to have an appropriate recognition sequence of a restriction enzyme.

The prepared cDNAs of VH and VL are respectively cloned so that each of them is expressed in an appropriate form in the upstream of gene encoding CH or CL of the human antibody of the vector for the human CDR-grafted antibody expression mentioned in the above (1) to construct a vector for human chimeric antibody expression.

In addition, cDNA encoding VH or VL of a non-human animal antibody is amplified by PCR using a synthetic DNA having a recognition sequence of an appropriate restriction enzyme at both ends, and each of them is cloned to the vector obtained in the above (1) for recombinant antibody expression.

(4) Construction of cDNA Encoding V Region of Human CDR-Grafted Antibody cDNAs encoding VH or VL of a human CDR-grafted antibody can be obtained as follows.

Amino acid sequences of FR in VH or VL of a human antibody to which amino acid sequences of CDRs in VH or VL of a non-human antibody are grafted are selected, respectively. Any amino acid sequences of FR can be used, as long as they are derived from human.

Examples thereof include amino acid sequences of FRs of human antibodies registered in database such as Protein Data Bank or the like, or amino acid sequences common to subgroups of FRs of human antibodies [A. L. F. DNA, US Dept. Health and Human Services (1991)] or the like. In order to inhibit the decrease in the binding activity of the antibody, amino acid sequences of FR having high homology (at least 60% or more) with the amino acid sequence of FR in VH or VL of the original antibody is selected.

Then, amino acid sequences of CDRs of the original antibody are grafted to the selected amino acid sequence of FR in VH or VL of the human antibody, respectively, to design each amino acid sequence of VH or VL of a human CDR-grafted antibody. The designed amino acid sequences are converted to DNA sequences by considering the frequency of codon usage found in nucleotide sequences of genes of antibodies [A. L. F. DNA, US Dept. Health and Human Services (1991)], and the DNA sequence encoding the amino acid sequence of VH or VL of a human CDR-grafted antibody is designed.

Based on the designed DNA sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR and the lengths of DNAs which can be synthesized.

Furthermore, the cDNA encoding VH or VL of a human CDR-grafted antibody can be easily cloned into the vector for expressing the human CDR-grafted antibody constructed in (1) by introducing the recognition sequence of an appropriate restriction enzyme to the 5' terminal of the synthetic DNAs existing on the both ends.

Otherwise, it can be carried out using a synthetic DNA as a single DNA encoding each of the full-length H chain and the full-length L chain based on the designed DNA sequence.

After PCR, an amplified product is cloned into a plasmid such as pBluescript SK (–) (manufactured by Stratagene) or the like, and the base sequence is determined according to a method similar to the method described in (2) to obtain a plasmid having a DNA sequence encoding the amino acid sequence of VH or VL of a desired human CDR-grafted antibody.

(5) Modification of Amino Acid Sequence of V Region of Human CDR-Grafted Antibody It is known that when a human CDR-grafted antibody is produced by simply grafting only CDRs in VH and VL of a non-human antibody into FRs of VH and VL of a human antibody, its antigen binding activity is lower than that of the original non-human antibody [BIO/TECHNOLOGY, 9, 266 (1991)].

In human CDR-grafted antibodies, among the amino acid sequences of FRs in VH and VL of a human antibody, an amino acid residue which directly relates to binding to an antigen, an amino acid residue which interacts with an amino acid residue in CDR, and an amino acid residue which maintains the three-dimensional structure of an antibody and indirectly relates to binding to an antigen are identified and replaced with an amino acid residue which is found in the original non-human antibody, thereby increasing the antigen binding activity which has been decreased.

In order to identify the amino acid residues relating to the antigen binding activity in FR, three-dimensional structure of an antibody can be constructed and analyzed by X-ray crystallography [J. Mol. Biol., 112, 535 (1977)], computer-modeling [Protein Engineering, 7, 1501 (1994)] or the like. In addition, modified human CDR-grafted antibody having sufficient binding activity against antigen can be obtained by trial and error, such as producing several modified antibodies of each antibody and examining their antigen binding activities.

The modification of the amino acid sequence of FR in VH and VL of a human antibody can be accomplished using various synthetic DNA for modification according to PCR as described in (4). With regard to the amplified product obtained by PCR, the base sequence is determined according to the method as described in (2) so as to examine whether the desired modification has been carried out.

(6) Construction of Vector for Human CDR-Grafted Antibody Expression

A vector for human CDR-grafted antibody expression can be constructed by cloning each cDNA encoding VH or VL of a constructed recombinant antibody into upstream of each gene encoding CH or CL of the human antibody in the vector for recombinant antibody expression as described in (1).

For example, recognizing sequences of an appropriate restriction enzymes are introduced to the 5'-terminal of synthetic DNAs positioned at both ends among synthetic DNAs used in the construction of VH or VL of the human CDR-grafted antibody in (4) and (5), and cloning can be carried out so that they are expressed in an appropriate form in the upstream of each gene encoding CH or CL of the human antibody in the vector for a human CDR-grafted antibody expression as described in (1).

(7) Transient Expression of Recombinant Antibody

The recombinant antibodies can be expressed transiently using the vector for recombinant antibody expression obtained in (3) and (6) or the modified expression vector thereof so as to efficiently evaluate the antigen binding activity of various human CDR-grafted antibodies.

Any cell can be used as a host cell, as long as the host cell is able to express a recombinant antibody. For example, COS-7 cell (ATCC CRL1651) is used [Methods in Nucleic Acids Res., CRC Press, 283 (1991)]. Introduction of the expression vector into COS-7 cell is performed by using a DEAE-dextran method [Methods in Nucleic Acids Res., CRC Press, 283 (1991)], a lipofection method [Proc. Natl. Acad. Sci. USA, 84, 7413 (1987)], or the like.

After introduction of the expression vector, the expression level and antigen binding activity of the recombinant antibody in the culture supernatant can be determined by the enzyme immunoassay [Monoclonal Antibodies—Principles and practice, Third edition, Academic Press (1996), Antibodies—A Laboratory Manual, Cold Spring Harbor Laboratory (1988), Monoclonal Antibody Experiment Manual, Kodansha Scientific (1987)] or the like.

(8) Acquisition of Transformant which Stably Expresses Recombinant Antibody and Preparation of Recombinant Antibody A transformant which stably expresses a recombinant antibody can be obtained by introducing the vector for recombinant antibody expression obtained in (3) and (6) into an appropriate host cell.

Introduction of the expression vector into a host cell is performed by electroporation [Japanese Published Unexamined Patent Application No. 257891/90, Cytotechnology, 3, 133 (1990)] or the like. As the host cell into which a vector for recombinant antibody expression is introduced, any cell can be used, as long as it is a host cell which is able to produce the recombinant antibody.

Examples thereof include CHO-K1 (ATCC CCL-61), DUkXB11 (ATCC CCL-9096), Pro-5 (ATCC CCL-1781), CHO-S (Life Technologies, Cat #11619), rat myeloma cell YB2/3HL.P2.G11.16Ag.20 (also called YB2/0), mouse myeloma cell NSO, mouse myeloma cell SP2/0-Ag14 (ATCC No. CRL1581), mouse P3-X63-Ag8653 cell (ATCC No. CRL1580), CHO cell in which a dihydrofolate reductase gene is defective [Proc. Natl. Acad. Sci. U.S.A., 77, 4216 (1980)], lectin resistance-acquired Lec13 [Somatic Cell and Molecular genetics, 12, 55 (1986)], CHO cell in which $\alpha 1,6$-fucosyltransaferse gene is defected (WO 2005/35586, WO 02/31140), rat YB2/3HL.P2.G11.16Ag.20 cell (ATCC No. CRL1662), or the like.

After introduction of the expression vector, transformants which stably express a recombinant antibody are selected by culturing them in a medium for animal cell culture containing an agent such as G418 sulfate or the like (Japanese Published Unexamined Patent Application No. 257891/90).

Examples of the medium for animal cell culture include RPMI1640 medium (manufactured by Invitrogen), GIT medium (manufactured by Nihon Pharmaceutical), EX-CELL301 medium (manufactured by JRH), IMDM medium (manufactured by Invitrogen), Hybridoma-SFM medium (manufactured by Invitrogen), media obtained by adding various additives such as FBS to these media, or the like.

The recombinant antibody can be produced and accumulated in a culture supernatant by culturing the obtained transformants in a medium. The expression level and antigen binding activity of the recombinant antibody in the culture supernatant can be measured by ELISA or the like. Also, in the transformant, the expression level of the recombinant antibody can be increased by using DHFR amplification system (Japanese Published Unexamined Patent Application No. 257891/90) or the like.

The recombinant antibody can be purified from the culture supernatant of the transformant by using a protein A column [Monoclonal Antibodies-Principles and practice, Third edition, Academic Press (1996), Antibodies—A Laboratory Manual, Cold Spring Harbor Laboratory (1988)]. In addition, the recombinant antibody can be purified by combining the protein purification methods such as gel filtration, ion-exchange chromatography, ultrafiltration or the like.

The molecular weight of the H chain or the L chain of the purified recombinant antibody or the antibody molecule as a whole is determined by polyacrylamide gel electrophoresis [Nature, 227, 680 (1970)], Western blotting [Monoclonal Antibodies—Principles and practice, Third edition, Academic Press (1996), Antibodies—A Laboratory Manual, Cold Spring Harbor Laboratory (1988)], or the like.

3. Activity Evaluation of Monoclonal Antibody or Antibody Fragment Thereof.

The activity of the purified monoclonal antibody or the antibody fragment thereof of the present invention can be evaluated in the following manner.

The binding activity to BMP9 and BMP9-expressing tissue is evaluated by the binding assay described in the above 1-(6-a) and a surface plasmon resonance method using such as the Biacore system described in the above (6-b). Furthermore, it can be measured by fluorescent antibody technique [Cancer Immunol. Immunother, 36, 373 (1993)] or the like.

4. Method for Treating Disease Using Anti-BMP9 Monoclonal Antibody or Antibody Fragment of the Present Invention The monoclonal antibody or the antibody fragment thereof of the present invention can be used for treating diseases accompanying BMP9-involved anemia.

The therapeutic agent comprising the monoclonal antibody or the antibody fragment thereof of the present invention or the derivative thereof may comprise only the antibody or the antibody fragment thereof or the derivative thereof as an active ingredient, and is preferably supplied as a pharmaceutical preparation produced by mixing it with one or more pharmaceutically acceptable carriers in accordance with an appropriate method well known in the technical field of pharmaceutics.

Examples of administration route may include oral administration and parenteral administration, such as buccal, tracheal, rectal, subcutaneous, intramuscular or intravenous administration. Examples of the dosage form may include sprays, capsules, tablets, powder, granules, syrups, emulsions, suppositories, injections, ointments, tapes or the like.

Examples of the pharmaceutical preparation suitable for oral administration may include emulsions, syrups, capsules, tablets, powders, granules or the like.

Liquid preparations such as emulsions and syrups can be produced using, as additives, water; sugars such as sucrose, sorbitol or fructose; glycols such as polyethylene glycol or propylene glycol; oils such as sesame oil, olive oil or soybean oil; antiseptics such as p-hydroxybenzoic acid esters; flavors such as strawberry flavor or peppermint; or the like.

Capsules, tablets, powders, granules or the like can be produced using, as additives, excipients such as lactose, glucose, sucrose or mannitol; disintegrating agents such as starch or sodium alginate; lubricants such as magnesium stearate or talc; binders such as polyvinyl alcohol, hydroxypropylcellulose or gelatin; surfactants such as fatty acid ester; plasticizers such as glycerin; or the like.

Examples of the pharmaceutical preparation suitable for parenteral administration may include injections, suppositories, sprays or the like.

Injections can be prepared using a carrier such as a salt solution, a glucose solution or a mixture of both thereof. Suppositories can be prepared using a carrier such as cacao butter, hydrogenated fat, carboxylic acid or the like.

Sprays can be prepared using a carrier which does not stimulate the buccal or airway mucous membrane of the patient and can facilitate absorption of the monoclonal antibody or the antibody fragment thereof by dispersing it as fine particles. Examples of the carrier include lactose, glycerol or the like. It is possible to produce pharmaceutical preparations as aerosols or dry powders.

In addition, the components exemplified as additives for oral preparations can also be added to the parenteral preparations.

Hereinafter, the present invention will be described in detail with reference to Examples. However, the present invention is not limited to the following Examples. Unless otherwise specified, all reagents are used in accordance with the accompanying documents.

EXAMPLES

Example 1

Construction of Targeting Vector for Mouse BMP9 Gene Knockout 1-1) Construction of Cassette Vector pBlueLAB-LoxP-Neo-DT-A A cassette vector pBlueLAB-LoxP-Neo-DT-A as a basic vector for the construction of a knockout (KO) targeting vector is a vector that is prepared by adding a restriction enzyme site to pBluescript and then inserting LoxP-Neo having LoxP sequences at both ends of neomycin-resistance marker gene expression unit and diphtheria toxin A chian gene (DT-A), and is the same as the vector described in Example 7 of WO 2006/078072. Hereinbelow, a strategy for vector construction will be described.

To add new restriction enzyme sites to the pBluescript II SK(−) (manufactured by TOYOBO) vector, the following oligoDNAs (LinkA1: SEQ ID NO:1, LinkA2: SEQ ID NO:2, LinkB1: SEQ ID NO:3, and LinkB2: SEQ ID NO:4) were synthesized.

pBluescript II SK(−) was treated with restriction enzymes, SaiI and XhoI, and then plasmid fragments were extracted from the reaction mixture using phenol/chloroform, followed by ethanol precipitation. To add the new restriction enzyme sites for NruI, SgrAI and AscI to this plasmid fragment, a linker consisting of LinkA1 and LinkA2 was inserted thereto, and introduced into E. coli DH5a. A plasmid pBlueLA was acquired from the obtained transformant.

pBlueLA was treated with restriction enzymes, NotI and EcoRI and then plasmid fragments were extracted from the reaction mixture using phenol/chloroform, followed by ethanol precipitation. To add the new restriction enzyme sites for PacI, FseI and SalI to this plasmid fragment, a linker consisting of LinkB1 and LinkB2 was inserted thereto, and introduced into E. coli DH5α. A plasmid pBlueLAB was acquired from the obtained transformant.

A plasmid pLoxP-STneo described in WO 00/10383 was digested with XhoI to obtain the Neo-resistance gene (LoxP-Neo) having LoxP sequence at both ends. The both ends of LoxP-Neo were converted to blunt ends using T4 DNA polymerase so as to obtain LoxP-Neo-B.

pBlueLAB was digested with EcoRV, and then plasmid fragments were extracted from the reaction mixture using phenol/chloroform, followed by ethanol precipitation. LoxP-Neo-B was inserted into the obtained plasmid fragment, and introduced into E. coli DH5α. A plasmid pBlueLAB-LoxP-Neo was acquired from the obtained transformant.

pMC1 DT-A (manufactured by Lifetech Oriental) was digested with XhoI and SalI, and a fragment containing DT-A gene was recovered using a QIAquick Gel Extraction Kit (manufactured by Qiagen).

pBlueLAB-LoxP-Neo was digested with XhoI, and then plasmid fragments were extracted from the reaction mixture using phenol/chloroform, followed by ethanol precipitation. The fragment containing DT-A gene was inserted into the obtained plasmid fragment, and introduced into E. coli DH5α. A cassette vector pBlueLAB-LoxP-Neo-DT-A was acquired from the obtained transformant.

1-2) Acquisition of 3' Genomic Region Fragment of Mouse BMP9 Gene

Based on the genomic DNA sequence (Accession No. ENSMUSG00000072625) including the mouse BMP9 (GDF2) gene obtained from Ensemble Genome Browser, primers (SEQ ID NOs:5 and 6) were designed.

DNA derived from the clone RP23-181N8 comprising C57BL/6J mouse BMP9 gene in bacterial artificial chromosome (BAC) as a template, each 10 pmol of the primers of SEQ ID NOs:5 and 6, and KOD-plus-(manufactured by TOYOBO) were added to prepare 50 μl of a reaction mixture. The reaction mixture was incubated at 94° C. for 3 minutes, and 35 cycles of PCR consisting of 98° C. for 10 seconds and 68° C. for 5 minutes was carried out.

The PCR amplified fragment was subjected to agarose gel electrophoresis, and 2.1 kbp of a fragment was recovered using a QIAquick Gel Extraction Kit (manufactured by Qiagen). The PCR amplified fragment thus recovered was digested with ClaI and AscI, and was subjected to agarose gel electrophoresis. The enzyme-digested fragment (ClaI-AscI fragment) was recovered using the QIAquick Gel Extraction Kit.

pBlueLAB was digested with ClaI and AscI, and treated with Shrimp Alkaline Phosphatase (SAP). Then, the ClaI-AscI fragment was extracted using phenol/chloroform, followed by ethanol precipitation. The ClaI-AscI fragment recovered was inserted, and introduced into *E. coli* DH5α.

Clones having a gene insert with no mutation due to PCR were selected from the obtained transformants, and the plasmid DNA was digested with ClaI and AscI, and subjected to agarose gel electrophoresis. 2.1 kbp of the enzyme-treated fragment including the 3' genomic region of mouse BMP9 gene was recovered using the QIAquick Gel Extraction Kit.

1-3) Acquisition of 5' Genomic Region Fragment of Mouse BMP9 Gene

Based on the genomic DNA sequence (Accession No. ENSMUSG00000072625) including the mouse BMP9 gene obtained from Ensemble Genome Browser, primers (SEQ ID NOs:7 and 8) were designed.

DNA derived from the BAC clone RP23-181N8 as a template, each 10 pmol of the primers of SEQ ID NOs:7 and 8, and KOD-plus-(manufactured by TOYOBO) were added to prepare 50 μl of a reaction mixture. The reaction mixture was incubated at 94° C. for 3 minutes, and 35 cycles of PCR consisting of 98° C. for 10 seconds and 68° C. for 5 minutes was carried out.

The PCR amplified fragment was subjected to agarose gel electrophoresis, and 5.1 kbp of a fragment was recovered using a QIAquick Gel Extraction Kit (manufactured by Qiagen). The PCR amplified fragment thus recovered was digested with PacI and FseI, and was subjected to agarose gel electrophoresis. The enzyme-digested fragment (PacI-FseI fragment) was recovered using the QIAquick Gel Extraction Kit.

pBlueLAB was digested with PacI and FseI, and treated with SAP. Then, the PacI-FseI fragment was extracted using phenol/chloroform, followed by ethanol precipitation. The PacI-FseI fragment thus recovered was inserted, and introduced into *E. coli* DH5α.

Clones having a gene insert with no mutation due to PCR were selected from the obtained transformants, and the plasmid DNA was digested with PacI and FseI, and subjected to agarose gel electrophoresis. 5.1 kbp of the enzyme-treated fragment comprising the 5' genomic region of mouse BMP9 gene was recovered using the QIAquick Gel Extraction Kit.

1-4) Insertion of the 3' Genomic Region Fragment of Mouse BMP9 Gene into Cassette Vector pBlueLAB-Lox-Neo-DT-A obtained in Example 1-1 was digested with ClaI and AscI, and subjected to agarose gel electrophoresis. Then, the DNA fragment was recovered using the QIAquick Gel Extraction Kit. The enzyme-treated fragment obtained in Example 1-2 was inserted into about 7.6 kbp of the recovered DNA fragment, which was introduced into *E. coli* DH5α. The DNA fragment-inserted clones were selected from the obtained transformant. The base sequence of the ligation portion was confirmed.

1-5) Insertion of 5' Genomic Region Fragment of Mouse BMP9 Gene into Cassette Vector Having 3' Genomic Region Fragment of Mouse BMP9 Gene The plasmid obtained in Example 1-4 was digested with PacI and FseI, and subjected to agarose gel electrophoresis. The enzyme-treated fragment was recovered using the QIAquick Gel Extraction Kit. The enzyme-treated fragment prepared in Example 1-3 was inserted into 9.7 kbp of the recovered DNA fragment, which was introduced into *E. coli* DH5α.

The DNA fragment-inserted clones were selected from the obtained transformants, and accuracy of the base sequence of the ligation portion was confirmed, so as to obtain pBluem-Bmp9-Lox-Neo-DT-A-3'KO-5'KO, which is a targeting vector for mouse BMP9 gene knockout (FIG. 1).

Example 2

Preparation of Mouse BMP9 Gene-Targeting Vector

60 μg of pBluemBmp9-Lox-Neo-DT-A-3'KO-5'KO obtained in Example 1-5 was digested with NotI in an H buffer for restriction enzyme prepared at pH 7.0 (manufactured by Roche Diagnostics) which was added at a final concentration of 1 mmol/L of spermidine (manufactured by SIGMA).

The vector fragment was extracted from the reaction mixture using phenol/chloroform, followed by ethanol precipitation. An HBS solution at pH 7.05 [containing 5 g of HEPES, 8 g of NaCl, 0.37 g of KCl, 0.125 g of $Na_2HPO_4 2H_2O$, and 1 g of Dextrose (D-Glucose) per 1 liter] was added to prepare a 0.5 μg/μl DNA solution and stored at room temperature for 1 hour. In this way, the mouse BMP9 gene-targeting vector, pBluemBmp9-Lox-Neo-DT-A-3'KO-5'KO-NotI for electroporation was prepared.

Example 3

Preparation of Probe for Southern Blot Analysis of Genome 3-1) Preparation of Probe for 5' Genomic Region of Mouse BMP9 Gene The primers (SEQ ID NOs:9 and 10) were designed in order to obtain a probe containing about 500 bp of the 5' genomic region of the mouse BMP9 gene, based on the nucleotide sequence information of BAC clone RP23-181N8.

50 μL of a reaction mixture was prepared by adding DNA derived from BAC clone RP23-181N8 as a template, each 10 pmol of the primers of SEQ ID NOs:9 and 10, and Takara Z Taq (manufactured by Takara Shuzo). After the reaction mixture was incubated at 94° C. for 2 minutes, 25 cycles of PCR consisting of 94° C. for 30 seconds, 60° C. for 20 seconds, and 72° C. for 1 minute was carried out. The amplified PCR fragment was subjected to agarose gel electrophoresis, and about 500 bp of a probe (5'KO-probe) for Southern blot analysis of the 5' genomic region was recovered using the QIAquick Gel Extraction Kit (manufactured by Qiagen).

3-2) Preparation of Probe for 3' Genomic Region of Mouse BMP9 Gene

The primers (SEQ ID NOs:11 and 12) were designed in order to obtain a probe containing about 500 bp of the 3' genomic region of the mouse BMP9 gene, based on the nucleotide sequence information of BAC clone RP23-181N8.

50 μL of a reaction mixture was prepared by adding DNA derived from BAC clone RP23-181N8 as a template, each 10 pmol of the primers of SEQ ID NOs:11 and 12, and Takara Z Taq (manufactured by Takara Shuzo). After the reaction mixture was incubated at 94° C. for 2 minutes, 25 cycles of PCR consisting of 94° C. for 30 seconds, 60° C. for 20 seconds, and 72° C. for 1 minute was carried out. The amplified PCR fragment was subjected to agarose gel electrophoresis, and about 500 bp of a probe (3'KO-probe) for Southern blot analysis of the 3' genomic region was recovered using the QIAquick Gel Extraction Kit (manufactured by Qiagen).

Example 4

Acquisition of Mouse BMP9 KO ES Cell Line

To obtain mouse BMP9 KO ES cells by homologous recombination, pBluemBmp9-Lox-Neo-DT-A-3'KO-5'KO- NotI prepared in Example 2 was introduced into mouse ES cell TT2 (Yagi et al., Analytical Biochem., 214:70, 1993) in accordance with the established method (Shinichi Aizawa, Gene Targeting, in Bio-Manual Series 8, YODOSHA CO., LTD., 1995). A detailed description of the method will be given in below.

TT2 cells were cultured under conditions of 37° C. and 5% $CO_2$ using, as a feeder cell, the G418 resistant primary cultured cell (manufactured by Invitrogen), which was treated with mitomycin C (manufactured by SIGMA). The TT2 cells were treated with trypsin and suspended in the HBS solution described in Example 2 at a density of $3 \times 10^7$ cells/ml. Thereafter, 0.5 ml of the cell suspension was mixed with 10 μg of pBluemBmp9-Lox-Neo-DT-A-3'KO-5'KO-NotI, placed in a gene pulsar cuvette (distance between electrodes: 0.4 cm; manufactured by Bio-Rad) and subjected to electroporation (capacity: 960 μF, voltage: 240 V, room temperature).

After electroporation, the cells were suspended in 10 ml of ES medium [containing 180 mL of fetal bovine serum (FBS), 3.5 g of D-glucose, 10 g of Dulbecco's Modified Eagle's Medium powder (manufactured by Invitrogen), 10 mL of non-essential amino acid solution (100-fold concentrate; manufactured by Invitrogen), and 1.9 g of sodium hydrogen carbonate per 1 liter] and seeded in a 100-mm plastic tissue-culture Petri dish (manufactured by Falcon) having feeder cells previously seeded therein. After 24 hours, the medium was replaced with fresh ES medium containing 200 μg/ml neomycin (manufactured by Sigma). The colonies generated after 7 days were picked up, and individually transferred to 24-well plates.

After the cells were grown up to the confluent state, one third of the cells was seeded in a 12-well gelatin coated plate and cultured for 2 days. From $10^6$ to $10^7$ cells, genomic DNA was prepared using Puregene DNA Isolation Kits (manufactured by Gentra System). The genomic DNA of the neomycin-resistant TT2 cells was digested with the restriction enzyme EcoRI and subjected to agarose gel electrophoresis. Subsequently, Southern blot was performed using the 3'KO-probe obtained in Example 3-2. In the wild-type TT2 cell, a single band (about 15.5 kbp) was detected. In the homologous recombinant, two bands (about 11.5 kbp and about 15.5 kbp) were detected.

The genomic DNA of clones which were confirmed as homologous recombinants was further digested with NcoI and subjected to agarose gel electrophoresis. Subsequently, Southern analysis was performed using the 5'KO-probe obtained in Example 3-1. In the wild-type TT2 cell, a single band (about 13.4 kbp) was detected. In the homologous recombinant, two bands (about 8.5 kbp and about 13.4 kbp) were detected.

As a result, 7 homologous recombinants expected to have the mouse BMP9 gene knockout were detected. Subsequently, karyotyping of the homologous recombinants was performed in accordance with the method as described in Bio-Manual Series 8, Gene Targeting (by Shinichi Aizawa, YODOSHA CO., LTD., 1995). As a result, it was confirmed that 5 out of 7 were mouse BMP9 gene KO ES Cells having a normal karyotype.

Example 5

Preparation of BMP9 KO Heterozygous Mouse

The ES cells obtained in Example 4 are TT2 cells derived from CBA×C57BL/6 F1 mouse with dark brown hair (Yagi et al., Analytical Biochemistry, 214: 70-76, 1993). Herein, to simply distinguish a chimeric mouse having a gene derived from ES cells and a host mouse having no gene derived from ES cells, ICR mouse with white hair was selected as the host mouse.

First, 4 out of the mouse BMP9 gene KO ES cell lines that were confirmed to have a normal karyotype in Example 4 were injected to 8-cell-stage embryos collected from female ICR mice mated with ICR males at a density of 8 to 10 cells per embryo, respectively. Thereafter, the embryos were incubated in ES media overnight to develop the injected embryos to blastocysts. About 10 injection embryos developed to blastocysts were transplanted in each one of the two uteri of a surrogate ICR mouse (CLEA Japan) 2.5 days after pseudopregnancy treatment.

When total 260 injection embryos developed to blastocysts were transplanted, 102 offspring chimeric mice were born. 89 out of 102 offsprings born were chimeric mice with the dark brown hair, in which the contribution of ES cells was observed. 40 of 89 offsprings were chimeric mice derived from ES cells with a high chimeric rate which had the dark brown hair and had no white hair.

Subsequently, when male chimeric mice with a high chimeric rate were crossed with female C57BL/6, offspring mice with dark brown hair were born, indicating transfer of the genome of ES cell to reproductive cell lineage.

The screening of the BMP9 gene-targeted heterozygous mouse was performed by PCR using DNA from the mouse tail biopsy as a template. To this end, mBMP9_FW5915 (SEQ ID NO:13) and mBMP9_RV17165 (SEQ ID NO:14) were prepared, which are the primers specific to the neomycin resistance gene region in the vector for mouse BMP9 gene knockout, pBluemBmp9-Lox-Neo-DT-A-3'KO-5'KO prepared in Example 1.

Tails were obtained from mice at 3 weeks or longer after birth (edited by Motoya Katsuki, A Laboratory Manual of Embryological Engineering, Kodansha Scientific, 1987), and genomic DNAs were extracted using a Puregene DNA Isolation Kit. 50 μL of a reaction mixture was prepared by using the genomic DNA as a template and each 10 pmol of the primers of SEQ ID NOs:13 and 14, and EX Taq (manufactured by TAKARA SHUZO), and 35 cycles of PCR consisting of 95° C. for 30 seconds, 60° C. for 1 minute and 72° C. for 2 minutes was carried out.

The result of agarose gel electrophoresis showed that about 1.3 kbp of PCR product was detected in a plurality of individuals. This result indicates that a plurality of heterozygous mice [BMP9KO(+/−)], in which homologous recombination of endogenous BMP9 gene occurred and the neomycin resistance gene was inserted, were obtained.

Example 6

Preparation of BMP9 KO Homozygous Mouse

Female and male BMP9KO(+/−) prepared in Example 5 were mated to obtain offsprings. In the same manner as in Example 5, genomic DNA was extracted from the mouse tail using the Puregene DNA Isolation Kit. PCR was carried out in the same manner as in Example 5 using this genomic DNA as a template. In addition, agarose electrophoresis was carried out to select BMP9KO heterozygous [BMP9KO(+/−) ] and homozygous [BMP9KO(−/−)].

50 μL of a reaction mixture was prepared by using the genomic DNAs of the selected individuals as a template and each 10 pmol of the primers of SEQ ID NOs:15 and 16, and EX Taq (manufactured by TAKARA SHUZO), and 35 cycles of PCR consisting of 95° C. for 30 seconds, 60° C. for 30 seconds and 72° C. for 1 minute was carried out. The result of agarose gel electrophoresis showed that there were about 200 bp of PCR product-detected individuals and non-detected individuals.

About 200 bp of PCR product was detected in BMP9KO (+/−) having the wild type allele, but not in BMP9KO(−/−). Thus, the result indicates acquisition of BMP9KO(−/−). 10 female mice out of the female and male homozygous [BMP9KO(−/−) ] mice were used for acquisition of anti-BMP9 monoclonal antibody.

Example 7

Preparation of Anti-Human BMP9 Monoclonal Antibody 7-1) Preparation of Immunogen The human BMP9 recombinant protein used as an immunogen was prepared according to the method described in Example 12 of WO 2010/126169.

7-2) Immunization of Animal and Preparation of Antibody-Producing Cell

The BMP9 KO(−/−) mice obtained in Example 6 were immunized with the human BMP9 recombinant protein prepared in Example 7-1 using RIBI adjuvant (manufactured by Corixa) or Titer Max Gold (manufactured by Titermax) as an adjuvant. In detail, a suspension of the human BMP9 recombinant protein was prepared according to the accompanying document of RIBI adjuvant, and administered into KO mice by intraperitoneal injection so that 25 μg of the human BMP9 recombinant protein per mouse was administered.

In the case of using Titer Max Gold, a suspension of the human BMP9 recombinant protein was also prepared according to the accompanying document, and administered into KO mice by subcutaneous injection so that 25 μg of the human BMP9 recombinant protein per mouse was administered. Immunization was performed three times in total, including the final boosting. 3 days after final administration, the spleens were excised.

The spleens excised were mashed in PBS (phosphate-buffered saline), and then splenocytes were collected by centrifugation (1500 rpm, 3 minutes). Because erythrocytes were included in the splenocytes thus obtained, the splenocytes were treated with RED Blood Cell Lysing Buffer (manufactured by SIGMA) on ice, so as to remove erythrocyte. The splenocytes thus obtained were washed with DMEM (Dulbecco's modified Eagle's Medium; Invitrogen) twice, and provided for cell fusion.

7-3) Preparation of Mouse Myeloma Cells

The mouse myeloma cell line (Sp2/0, ATCC: CRL1581) was cultured in DMEM supplemented with 10% fetal bovine serum and used as a parental strain for cell fusion.

7-4) Preparation of Hybridoma

The mouse splenocytes obtained in Example 7-2 and the myeloma cells obtained in Example 7-3 were mixed at a ratio of 5:1, followed by centrifugation (1500 rpm, 3 minutes). 1 mL of polyethylene glycol-1500 (manufactured by Roche Diagnostics) was slowly added to the precipitated fraction (cell groups) thus obtained, while gently agitating the solution. Subsequently, 5 mL of DMEM was added to the cell solution while gently agitating the solution. 10 mL of DMEM medium was further added thereto. Thereafter, the tube containing the cell solution was incubated at 37° C. for 5 minutes, followed by centrifugation (1500 rpm, 3 minutes).

The precipitated fraction (cell groups) thus obtained was suspended in a complete medium (DMEM medium containing 10 v/v % FCS, 50 μmol/L of β-mercaptoethanol, 50 μg/mL of insulin, and 10 ng/mL of IL-6] at a density of $1\times10^6$ splenocytes/mL, and 100 μL it thereof were seeded in a 96-well plate.

1.5 hours later, 100 μL of the complete medium containing HAT media supplement (manufactured by SIGMA, Cat#H0262-10VL) at two-fold higher concentration than the final concentration recommended by the manufacturer were added to each well, followed by incubation under the conditions of 37° C. and 5% $CO_2$. The medium replacement was performed using the complete medium containing HAT media supplement at the final concentration recommended by the manufacturer three times a week, until the number of cells in the well became suitable for screening.

7-5) Construction of ALK1/BMP9 Sandwich ELISA

ALK1/BMP9 sandwich ELISA was constructed using the anti-human BMP9 mouse monoclonal antibody (manufactured by R&D systems, clone No. 360107, hereinafter, referred to as R&D antibody), and a fusion protein (hsALK1-Fc) of human ALK1 extracellular domain known as a human BMP9 type I receptor and human IgG1 Fc region, as follows.

First, 0.05 μg/mL of hsALK1-Fc prepared according to the method described in Example 1 of WO 2010/126169 in 50 mmol/L $NaHCO_3$ buffer (manufactured by Wako, Cat#191-01305) was added to a 96-well plate for ELISA (F96 MAX-ISORP NUNC-IMMUNO PLATE, manufactured by Thermo Fisher Scientific, Cat#439454) at an amount of 100 μL/well, and left at 4° C. overnight for adsorption.

After removal of the solid phase reagent, 250 μL/well of SuperBlock (manufactured by Thermo SCIENTIFIC, Cat#37535) was added, and left at room temperature for 1 hour for blocking, and washing was carried out using PBS containing 0.1% Tween-20 (PBS-T) three times.

Subsequently, 1 ng/mL of human mature dimer BMP9 recombinant protein (manufactured by R&D, Cat#3209-BP) in 10% SuperBlock in PBS-T that was prepared by mixing SuperBlock and PBS-T at a ratio of 1:9 was aliquoted at an amount of 100 μL/well, and left at room temperature for 1 hour, followed by washing using PBS-T four times.

Subsequently, R&D antibody labeled with biotin using a SureLINK Chromophoric Biotin Labeling Kit (manufactured by KPL) was prepared at a concentration of 30 ng/mL using 10% SuperBlock in PBS-T, and 100 μL/well thereof was aliquoted and left at room temperature for 1 hour. The plate was washed with PBS-T four times, and then 100 μL/well of Streptavidin-polyHRP80 (manufactured by Stereospecific Detection Technologies, Cat#SP80D50) which was a 500-fold dilution in 10% SuperBlock in PBS-T was aliquoted and left at room temperature for 30 minutes to 1 hour.

The plate was washed with PBS-T four times, and 100 μL/well of a TMB chromogen reagent (TMB+ Substrate-Chromogen, manufactured by Dako, Cat#S 1599) was added for color-development. When proper color was developed, 100 μL/well of the 1 N sulfuric acid solution (manufactured by Wako, Cat#192-04755) was added, and absorbance at 450 nm was determined using ARVO (manufactured by PerkinElmer).

7-6) Screening of Anti-Human BMP9 Antibody-Producing Hybridoma Using ALK1/BMP9 Sandwich ELISA When the human mature dimer BMP9 recombinant protein was added to the sandwich ELISA constructed in Example 7-5, 10% SuperBlock in PBS-T solution which was prepared to contain 1 ng/mL of human mature dimer BMP9 recombinant protein, and 50% hybridoma culture supernatant prepared in Example 7-4 was aliquoted at an amount of 100 μL/well.

A medium for hybridoma was used as a negative control. The wells whose coloring was suppressed compared to the wells to which the medium for hybridoma added was considered as positive, and hybridomas that produced antibodies inhibiting interaction of hsALK1-Fc and human mature dimer BMP9 recombinant protein, or interaction of human mature dimer BMP9 recombinant protein and R&D antibody were selected.

Limiting dilution of the selected hybridomas was performed using the complete medium containing HT (manufactured by SIGMA, Cat#H0137-10VL), and the hybridomas were seeded in a 96-well plate for cloning. The hybridomas derived from the well which was determined as positive in the first round was subjected to cloning in total three times. By the above manipulation, hybridomas producing 6D 10-1-1 antibody, 10D5-2-3 antibody and 3B7-3-3 antibody were isolated.

7-7) Adaptation of Hybridoma to eRDF Medium

To obtain a large amount of antibodies, the complete medium for hybridomas was serially replaced by eRDF medium [e-RDF medium (Kyokuto Pharmaceutical Industrial Co., Ltd) containing 1 v/v % of Ultra-Low IgG FBS (manufactured by GIBCO), 5 µg/mL of Transfelin, 5 µg/mL of insulin, 10 mmol/L of ethanolamine, and 25 nmol/L of Sodium Selenite], and adaptation of hybridoma cells to eRDF medium was performed.

7-8) Mass-Production of Antibody from Hybridoma

The hybridomas adapted in Example 7-8 were seeded in 100 roller bottles (850 cm$^2$, manufactured by BD Biosciences) at a density of 1 to $2 \times 10^5$ cells/mL. eRDF medium was used as a medium. The roller bottles were incubated with shaking using a rotary incubator for roller bottles at 37° C. for 6-8 days, and then the medium containing cells were recovered. The recovered medium was centrifuged, and the resulting culture supernatant was filtered using a 0.22 µm filter.

Anti-human BMP9 antibodies were purified from the filtered culture supernatant using an open column packed with Protein Sepharose 4 Fast Flow (manufactured by GE Healthcare). The antibodies thus obtained were sterilized using a 0.22 µm filter, and provided for in vivo test.

Example 8

Specificity Evaluation of Obtained Antibodies by Enzyme-Linked Immunosorbent Assay (ELISA) Using Immobilized Antigen To examine specificity of the obtained antibodies to human BMP9, their binding ability to human BMP9 and human BMP10 having the highest homology to human BMP9 was tested by comparison. First, 100 ng/mL of human mature dimer BMP9 recombinant protein (manufactured by R&D systems, Cat#3209-BP), or human mature dimer BMP10 recombinant protein (manufactured by R&D systems, Cat#2926-BP) prepared in 50 mmol/L NaHCO$_3$ buffer (manufactured by Wako, Cat#191-01305) was added to a 96-well plate for ELISA (F96 MAXISORP NUNC-IMMUNO PLATE, manufactured by Thermo Fisher Scientific, Cat#442404) at an amount of 50 µL/well, and left at 4° C. overnight for adsorption.

After removal of the reagent for immobilization, 200 µL/well of SuperBlock (manufactured by Thermo SCIENTIFIC, Cat#37535) was added, and left at room temperature for 1 hour for blocking, and washing was carried out using TBST (Tris Buffered Saline with Tween 20; manufactured by SANTA CRUZ, SC-24953) three times.

Subsequently, 6D10-1-1 antibody, 10D5-2-3 antibody, 3B7-3-3 antibody, R&D antibody, or anti-BMP10 antibody (manufactured by R&D, Cat#MAB2926) that was labeled with biotin using a Biotin Labeling Kit-NH2 (manufactured by COSMO BIO, Cat#LK03) was prepared at a concentration of 100 ng/mL using 10% Super Block in TBST which was prepared by mixing SuperBlock and TBST at a ratio of 1:9. 50 µL/well thereof was aliquoted as a primary antibody, and left at room temperature for 1 hour.

The plate was washed with TBST three times, and then 100 µL/well of Streptavidin-polyHRP80 (manufactured by Stereospecific Detection Technologies, Cat#SP80D50) which was a 500-fold dilution in 10% Super Block in TBST was aliquoted and left at room temperature for 1 hour.

The plate was washed with TBST five times, and 50 µL/well of the TMB substrate reagent (TMB+ Substrate-Chromogen, manufactured by Dako, Cat#S1599) was added for color-development. When proper color was developed, 50 µL/well of the 1 N sulfuric acid solution (manufactured by Wako, Cat#192-04755) was added, and absorbance (450 nm-570 nm) at a sample wavelength of 450 nm and at a reference wavelength of 570 nm was determined using a plate reader (manufactured by Spectra Max, Molecular Devices).

Figure 2:
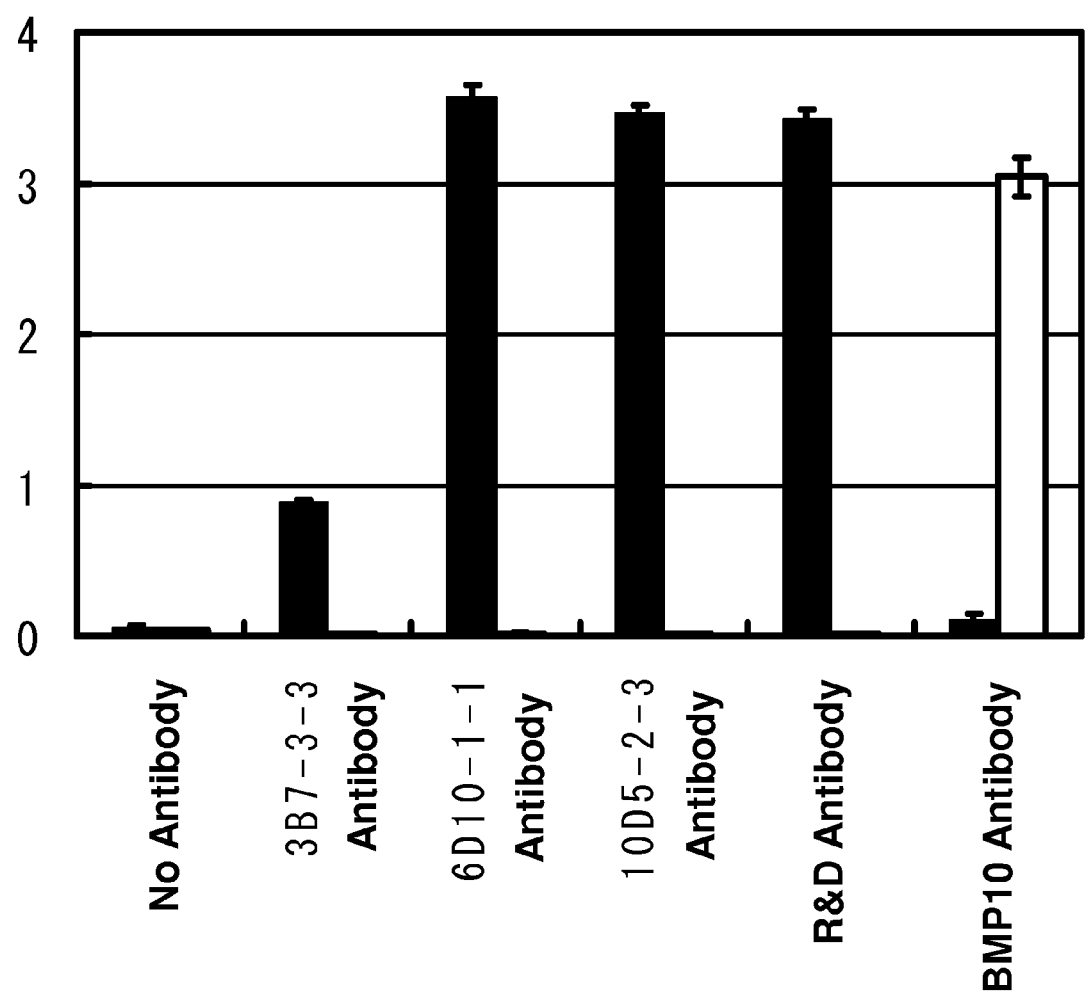
FIG. 2 shows the results of Enzyme-Linked Immunosorbent Assay (ELISA) for measuring binding specificity of the obtained anti-BMP9 monoclonal antibody to human BMP9, in which the vertical axis represents absorbance (450-570 nm), and if the solid-phase antigen is human BMP9, it is represented by black, and if the solid-phase antigen is human BMP10, it is represented by white.

The results are shown in FIG. 2. As shown in FIG. 2, 6D10-1-1 antibody, 10D5-2-3 antibody and 3B7-3-3 antibody showed a strong binding to human BMP9 and no binding to human BMP10, like R&D antibody, indicating that 6D10-1-1 antibody, 10D5-2-3 antibody and 3B7-3-3 antibody are antibodies specifically binding to human BMP9.

Example 9

Evaluation of Binding Property of Obtained Antibodies to Human BMP9 Recombinant Protein To determine binding activity of the obtained anti-human BMP9 antibody to human BMP9, the following experiment was performed.

First, 100 ng/mL of human mature dimer BMP9 recombinant protein (manufactured by R&D systems, Cat#3209-BP) prepared in 50 mmol/L NaHCO$_3$ buffer was added to a 96-well plate for ELISA (F96 MAXISORP NUNC-IMMUNO PLATE, manufactured by Thermo Fisher Scientific, Cat#439454) at an amount of 50 µL/well, and left at 4° C. overnight for adsorption.

After removal of the reagent for immobilization, 200 µL/well of SuperBlock (manufactured by Thermo SCIENTIFIC, Cat#37535) was added, and left at room temperature for 1 hour for blocking, and washing was carried out using TBST three times. Subsequently, the biotin-labeled 6D10-1-1 antibody, 10D5-2-3 antibody, 3B7-3-3 antibody or R&D antibody was prepared at a concentration of 1, 5, 20, 100, or 300 ng/mL using 10% Super Block in TBST. Each 50 µL/well thereof was aliquoted, and left at room temperature for 1 hour.

The plate was washed with TBST three times, and then 100 µL/well of Streptavidin-polyHRP80 which was a 500-fold dilution in 10% Super Block in TBST was aliquoted and left at room temperature for 1 hour.

The plate was washed with TBST five times, and 50 µL/well of the TMB substrate reagent (TMB+ Substrate-Chromogen, manufactured by Dako, Cat#S1599) was added for color-development. When proper color was developed, 50 µL/well of the 1 N sulfuric acid solution (manufactured by Wako, Cat#192-04755) was added, and absorbance (450 nm-570 nm) at a sample wavelength of 450 nm and at a reference wavelength of 570 nm was determined using a plate reader (manufactured by Spectra Max, Molecular Devices).

Figure 3:
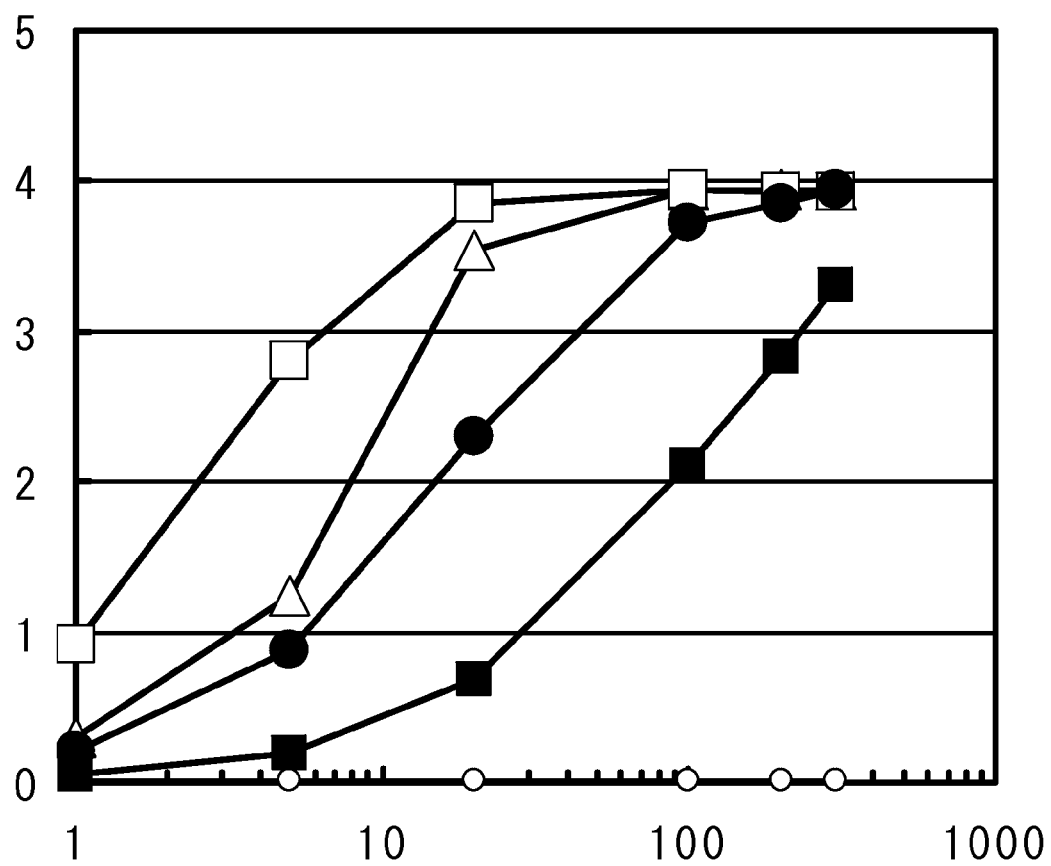
FIG. 3 shows the results of Enzyme-Linked Immunosorbent Assay (ELISA) for measuring binding property of the obtained anti-BMP9 monoclonal antibody to human BMP9, in which the horizontal axis represents antibody concentration (ng/mL), the vertical axis represents absorbance (450-570 nm) at each antibody concentration, 6D10-1-1 antibody is represented by △, 10D5-2-3 antibody is represented by □, 3B7-3-3 antibody is represented by ■, and R&D antibody is represented by ●.

The results are shown in FIG. 3. As shown in FIG. 3, 6D10-1-1 antibody, 10D5-2-3 antibody and 3B7-3-3 antibody bound to human BMP9 as the antibody concentration increased, like R&D antibody. It was also revealed that the binding activity of 6D10-1-1 antibody and 10D5-2-3 antibody to human BMP9 was higher than that of R&D antibody.

Example 10

Effect of Obtained Antibody on Binding of Human BMP9 and R&D Antibody

Based on the characteristics of the system used in Example 7, it is considered that the obtained antibodies inhibit any one of interaction of hsALK1-Fc and human mature dimer BMP9 recombinant protein or interaction of human mature dimer BMP9 recombinant protein and R&D antibody. Therefore, a binding assay system of human BMP9 and R&D antibody was first constructed.

100 ng/mL of the human BMP9 recombinant protein of Example 7-1 prepared in 50 mmol/L NaHCO₃ buffer was added to a 96-well plate for ELISA (F96 MAXISORP NUNC-IMMUNO PLATE, manufactured by Thermo Fisher Scientific, Cat#439454) at an amount of 100 µL/well, and left at room temperature for 1 hour for adsorption. After removal of the reagent for immobilization, 250 µL/well of Super Block was added, and left at room temperature for 1 hour for blocking, and washing was carried out using PBS-T three times.

Subsequently, 100 to 3000 ng/mL of the obtained antibody and 50 ng/mL of the biotin-labeled R&D antibody were prepared using 10% Super Block in PBS-T. Each 100 tit/well thereof was aliquoted, and left at room temperature for 1 hour. The plate was washed with PBS-T four times, and then 100 pt/well of Streptavidin-polyHRP80 (manufactured by Stereospecific Detection Technologies, Cat#SP80D50) which was a 500-fold dilution in 10% Super Block in PBS-T was aliquoted and left at room temperature for 30 minutes to 1 hour.

The plate was washed with PBS-T four times, and 100 µL/well of the TMB chromogen reagent (TMB+ Substrate-Chromogen, manufactured by Dako, Cat#S1599) was added for color-development. When proper color was developed, 100 µL/well of the 1 N sulfuric acid solution (manufactured by Wako, Cat#192-04755) was added, and absorbance at 450 nm was determined using ARVO (manufactured by PerkinElmer). The results are shown in FIG. 4.

Figure 4:
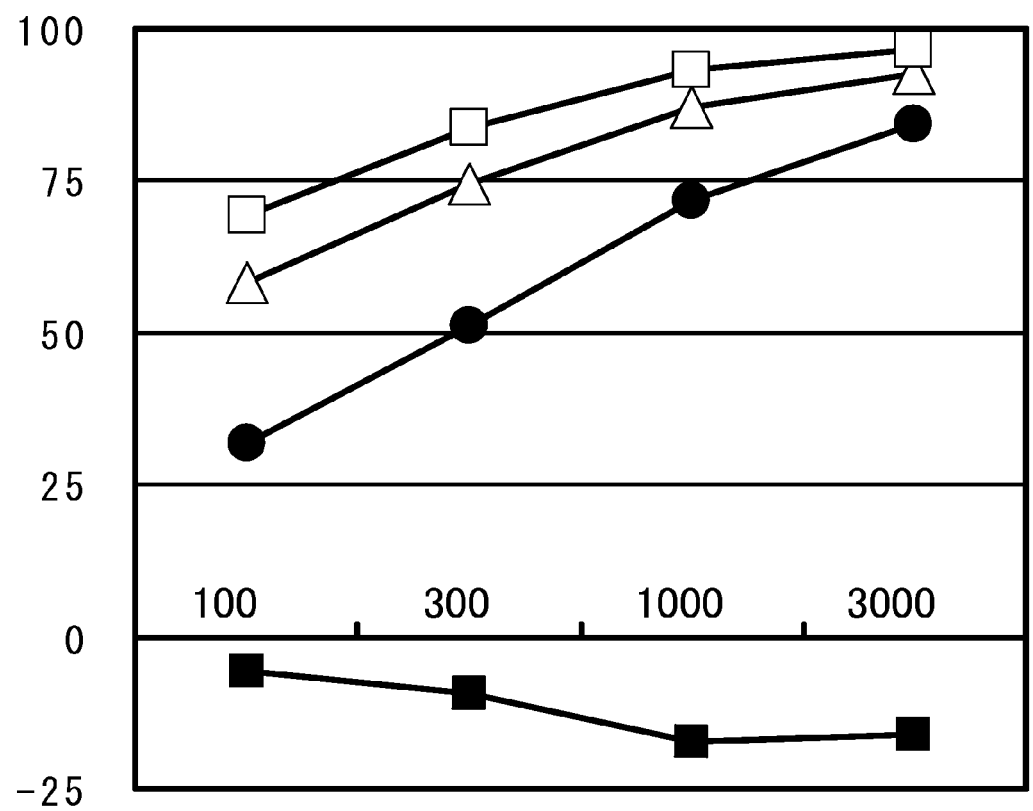
FIG. 4 shows the inhibitory effect of the obtained anti-BMP9 monoclonal antibody on binding of human BMP9 and labeled R&D antibody, in which the horizontal axis represents the concentration (ng/mL) of non-labeled antibody, the vertical axis represents inhibitory activity (%), 6D10-1-1 antibody is represented by A, 10D5-2-3 antibody is represented by □, 3B7-3-3 antibody is represented by ■, and R&D antibody is represented by ●.

As shown in FIG. 4, binding of human BMP9 and biotin-labeled R&D antibody was inhibited by addition of non-labeled R&D antibody, and also by addition of 10D5-2-3 antibody or 6D10-1-1 antibody. Meanwhile, the inhibition was not observed by addition of 3B7-3-3 antibody.

These results indicate that human BMP9 recognition sites (epitopes) of 10D5-2-3 antibody and 6D10-1-1 antibody are identical or close to that of R&D antibody, but human BMP9 recognition site (epitopes) of 3B7-3-3 antibody is different from that of R&D antibody.

Because they showed the inhibitory activity at a lower concentration than R&D antibody, binding activities (affinity) of 10D5-2-3 antibody and 6D10-1-1 antibody to human BMP9 are higher than that of R&D antibody.

Example 11

Effect of Obtained Antibodies on Binding of Human BMP9 and Human ALK1

Subsequently, a binding assay system of human BMP9 and human ALK1 was constructed. 100 ng/mL of the human BMP9 recombinant protein of Example 7-1 prepared in 50 mmol/L NaHCO₃ buffer was added to a 96-well plate for ELISA (F96 MAXISORP NUNC-IMMUNO PLATE, manufactured by Thermo Fisher Scientific, Cat#439454) at an amount of 100 µL/well, and left at room temperature for 1 hour for adsorption.

After removal of the reagent for immobilization, 250 µL/well of Super Block was added, and left at room temperature for 1 hour for blocking, and washing was carried out using PBS-T three times. Subsequently, 100, 1000 or 10000 ng/mL of the obtained antibody or R&D antibody, and 100 ng/mL of the biotin-labeled hsALK1-Fc protein were prepared using 10% Super Block in PBS-T. Each 100 µL/well thereof was aliquoted, and left at room temperature for 1 hour.

The plate was washed with PBS-T four times, and then 100 µL/well of Streptavidin-polyHRP80 (manufactured by Stereospecific Detection Technologies, Cat#SP80D50) which was a 500-fold dilution in 10% Super Block in PBS-T was aliquoted and left at room temperature for 30 minutes to 1 hour.

The plate was washed with PBS-T four times, and 100 µL/well of the TMB chromogen reagent (TMB+ Substrate-Chromogen, manufactured by Dako, Cat#S1599) was added for color-development. When proper color was developed, 100 µL/well of the 1 N sulfuric acid solution (manufactured by Wako, Cat#192-04755) was added, and absorbance at 450 nm was determined using ARVO (manufactured by PerkinElmer).

100, 1000 or 10000 ng/mL of 3B7-3-3 antibody showed 10.3%, 29.2%, or 64% inhibition on the binding of human BMP9 and human ALK1, respectively. The inhibition was not observed even though 6D10-1-1 antibody, 10D5-2-3 antibody and R&D antibody were added at the maximum dose of 10000 ng/mL.

These results revealed that 3B7-3-3 antibody is an anti-BMP9 antibody inhibiting the binding of human BMP9 and human ALK1, whereas 6D10-1-1 antibody, 10D5-2-3 antibody or R&D antibody is an anti-BMP9 antibody not inhibiting the binding of human BMP9 and human ALK1.

Example 12

Effect of Obtained Antibody on Binding of Human BMP9 and Human BMPRII

It is known that the BMP9 receptor consists of BMP type I receptor and BMP type II receptor, and BMP9 binds to both types of the receptor. Example 11 revealed that 10D5-2-3 antibody, 6D10-1-1 antibody and R&D antibody do not inhibit binding of human BMP9 and human ALK1, suggesting that these antibodies do not inhibit binding of BMP9 and BMP type I receptor.

Subsequently, to examine whether these antibodies inhibit binding of BMP9 and BMP type II receptor, a binding assay system of human BMP9 and human BMPRII that is known as one of human BMP9 type II receptor was constructed.

3 µg/mL of the human BMP9 recombinant protein of Example 7-1 prepared in 50 mmol/L NaHCO₃ buffer was added to a 96-well plate for ELISA (F96 MAXISORP NUNC-IMMUNO PLATE, manufactured by Thermo Fisher Scientific, Cat#439454) at an amount of 100 µL/well, and left at room temperature for 1 hour for adsorption. After removal of the reagent for immobilization, 260 µL/well of Super Block was added, and left at room temperature for 1 hour for blocking, and washing was carried out using TBST four times.

Subsequently, 1000 ng/mL of the obtained antibodies, R&D antibody, or a negative control mouse IgG1 monoclonal antibody (manufactured by DAKO, X0931) and 3 μg/mL of BMPRII-Fc (fusion recombinant protein of extracellular domain of human BMPRII and human IgG1Fc region, manufactured by R&D systems) were prepared using 10% Super Block in TBST. Each 100 μL/well thereof was aliquoted, and left at room temperature for 1 hour.

The plate was washed with TBST four times, and then 100 μL/well of Goat anti-human IgG HRP (manufactured by Thermo Scientific) which was a 20000-fold dilution in 10% SuperBlock in TBST was aliquoted and left at room temperature for 30 minutes to 1 hour.

The plate was washed with TBST four times, and 100 μL/well of the TMB chromogen reagent (TMB+ Substrate-Chromogen, manufactured by Dako, Cat#S 1599) was added for color-development. When proper color was developed, 100 μL/well of the 1 N sulfuric acid solution (manufactured by Wako, Cat#192-04755) was added, and absorbance at 450 nm was determined using Multiskan Ascent (manufactured by Thermo Labsystems). The results are shown in FIG. 5.

Figure 5:
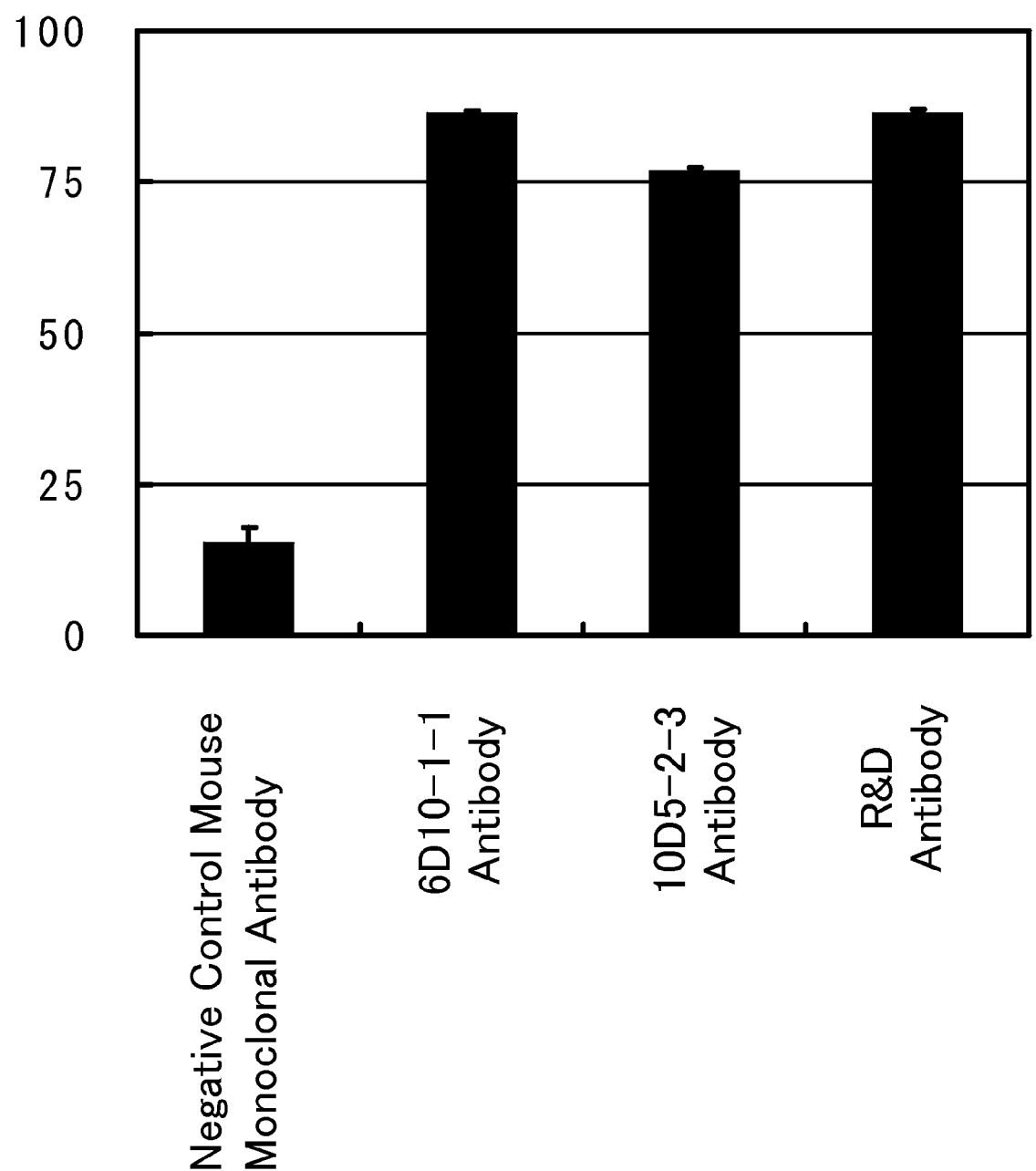
FIG. 5 shows the inhibitory effect of the obtained anti-BMP9 monoclonal antibody on binding of human BMP9 and BMPRII, in which the vertical axis represents inhibitory activity (%).

As shown in FIG. 5, binding of human BMP9 and human BMPRII was inhibited by 6D10-1-1 antibody, 10D5-2-3 antibody and R&D antibody, indicating that these antibodies are anti-human BMP9 antibodies inhibiting binding of BMP9 and BMPRII receptor.

Example 13

Binding Activity of Obtained Antibodies to Human BMP9 Recombinant Protein (Biacore Analysis)

The binding activity (affinity) of the obtained antibodies to human BMP9 recombinant protein was examined using BIAcore 2000 (manufactured by GE Healthcare). After anti-mouse IgG antibody was immobilized onto a CM5 sensor chip using a Mouse Antibody Capture Kit (manufactured by GE Healthcare), anti-human BMP9 antibody was coupled to an RU value of 700-1100.

Thereafter, 0.152 nmol/L, 0.457 nmol/L, 1.37 nmol/L, 4.1 nmol/L, 12.3 nmol/L, 36.89 nmol/L, 110.67 nmol/L, and 322 nmol/L of the human BMP9 recombinant protein prepared in Example 7-1 were prepared by using an HBS-EP solution (manufactured by GE Healthcare) and added as analytes, and binding affinity was measured.

Based on the obtained values, the dissociation constant (Kd value) was calculated by single cycle kinetics (BIAevaluation Software ver. 3, manufactured by GE Healthcare). The results are given in Table 1.

TABLE 1

| Antibody name | Kd (M) | Relative binding affinity (to R&D antibody) |
|---|---|---|
| R&D antibody | $6.16 \times 10^{-10}$ | 1-fold |
| 6D10-1-1 antibody | $2.97 \times 10^{-11}$ | 20.7-fold |
| 10D5-2-3 antibody | $9.69 \times 10^{-12}$ | 63.6-fold |

As shown in Table 1, Kd value of R&D antibody was $6.16 \times 10^{-10}$ mol/L, whereas Kd values of 6D10-1-1 antibody and 10D5-2-3 antibody were $2.97 \times 10^{-11}$ mol/L and $9.69 \times 10^{-12}$ mol/L, respectively. Binding activities of 6D10-1-1 antibody and 10D5-2-3 antibody to human BMP9 showed 20.7-fold and 63.6-fold, respectively, which are remarkably higher than that of R&D antibody. These results are consistent with those of Examples 9 and 10.

Example 14

Activity of Obtained Antibodies on Erythropoiesis in Normal Balb/c Mouse (Short-Term Administration)

As revealed in Example 9, 6D10-1-1 antibody and 10D5-2-3 antibody are antibodies binding to human BMP9 mature dimer. 106 amino acids of mouse BMP9 and 104 amino acids of rat BMP9 completely matched with human BMP9 mature region composed of 110 amino acids, represented by SEQ ID NO:67, indicating that BMP9 is very highly conserved between species. Therefore, it is inferred that these antibodies bind to rodent BMP9, like to human BMP9.

Therefore, erythropoietic activity of 6D10-1-1 antibody and 10D5-2-3 antibody was evaluated using BALB/c mouse. 6-week-old male BALB/c mise (Charles River Laboratories Japan Inc.) were purchased and provided for experiment. Sterile tap water was used as drinking water, and solid feed FR-2 (manufactured by Funabashi Farm) was provided as diet with free access.

After pre-breeding, mice were divided into 7 groups (n=6 per group) based on body weight, and 6D10-1-1 antibody, 10D5-2-3 antibody or R&D antibody was administered at a dose of 1 mg/kg or 3 mg/kg by subcutaneous injection. In detail, each antibody was prepared in a concentration of 0.1 mg/mL or 0.3 mg/mL using physiological saline, and each was administered at a dose of 10 mL/kg. The vehicle group was administered with physiological saline at a dose of 10 mg/kg by subcutaneous injection.

The antibody or vehicle was administered once a week in total twice. 2 weeks after first administration, laparotomy was performed under isoflurane anesthesia, and blood was collected from the postcaval vein, put in an EDTA-containing tube, and used as a blood sample.

The number of blood cells and the concentration of hemoglobin in the blood samples thus obtained were determined using an automated blood cell counter Celltac α (manufactured by Nihon Kohden Corporation). The results are shown in FIGS. 6A and 6B.

Figure 6A:
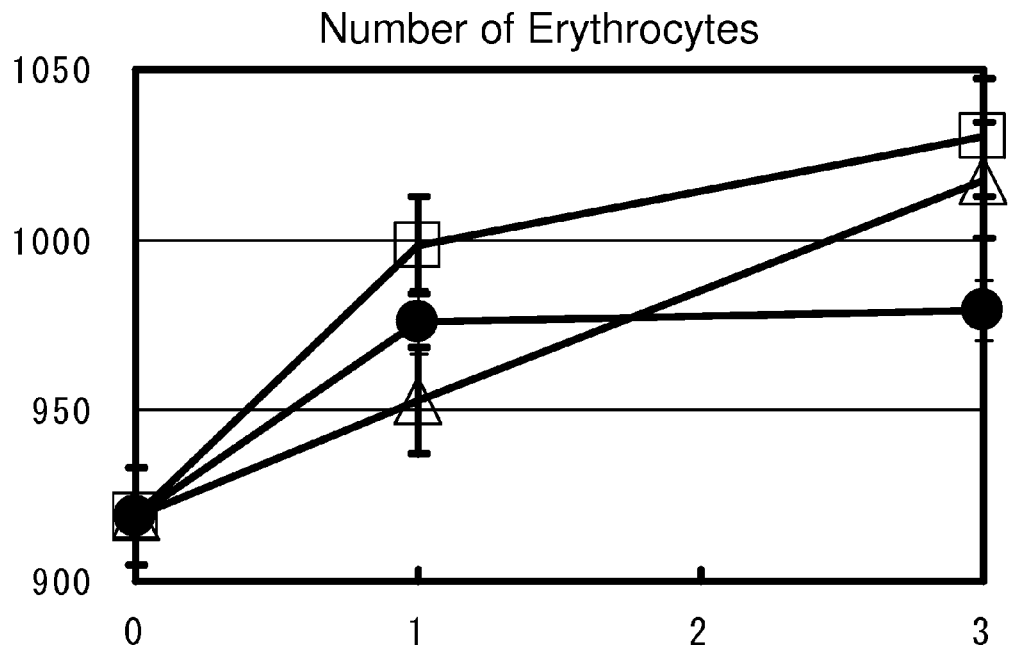
FIG. 6A shows the effect of the obtained anti-BMP9 monoclonal antibody on mouse erythropoiesis by short-term administration (for 2 weeks), and the graph of FIG. 6A represents changes in the number of erythrocyte, in which the horizontal axis represents the administration dose of antibody (mg/kg) and the vertical axis represents the number of erythrocyte ($\times 10^4$ µL), 6D10-1-1 antibody is represented by △, 10D5-2-3 antibody is represented by □, and R&D antibody is represented by ●. In the drawing, the value of 0 mg/kg represents that of the vehicle-treated group, and the error bar represents standard error of mean (SE, n=6).
Figure 6B:
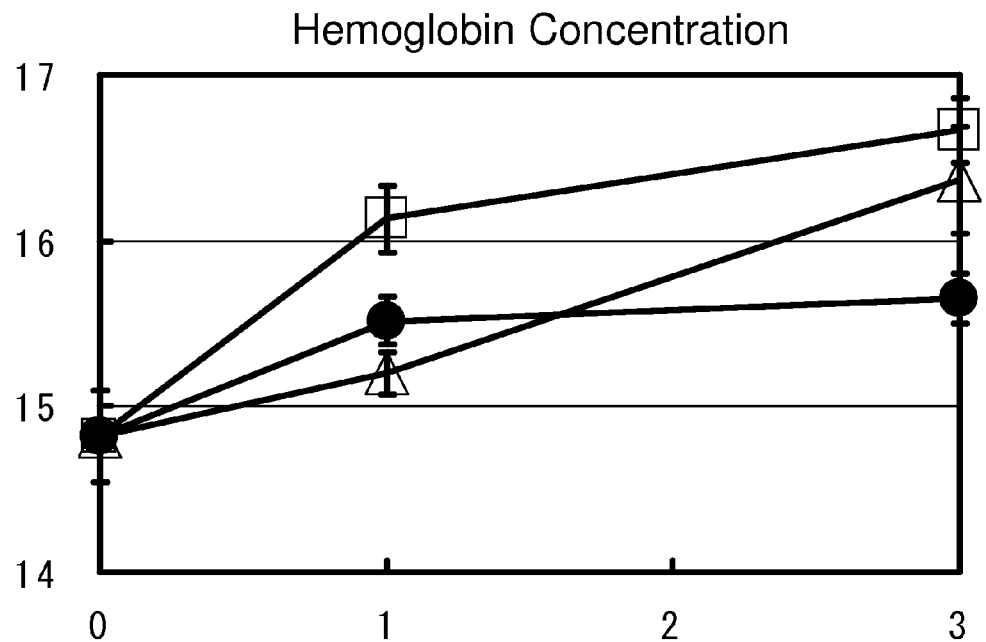
FIG. 6B shows the effect of the obtained anti-BMP9 monoclonal antibody on mouse erythropoiesis by short-term administration (for 2 weeks), and the graph of FIG. 6B represents changes in the hemoglobin concentration, in which the horizontal axis represents the administration dose of antibody (mg/kg) and the vertical axis represents the hemoglobin concentration (g/dL), 6D10-1-1 antibody is represented by A, 10D5-2-3 antibody is represented by □, and R&D antibody is represented by ●. In the drawing, the value of 0 mg/kg represents that of the vehicle-treated group, and the error bar represents standard error of mean (SE, n=6).

As shown in FIGS. 6A and 6B, the number of erythrocyte and the concentration of hemoglobin were increased by administration of any of the anti-human BMP9 antibodies, indicating that the anti-human BMP9 antibody has the erythropoietic activity. When R&D antibody was administered at a dose of 1 mg/kg or 3 mg/kg, the number of erythrocyte and the concentration of hemoglobin were increased at a similar level, indicating that R&D antibody exhibits the maximum activity at a dose of 1 mg/kg or less. Meanwhile, when the antibody was administered at the maximum activity dose of 1 mg/kg, the increase in the concentration of hemoglobin was approximately 0.7 g/dL.

Meanwhile, the maximum activities of 6D 10-1-1 antibody and 10D5-2-3 antibody were about 2-fold higher than that of R&D antibody. In particular, the increase in the hemoglobin concentration was approximately 1.5 to 2 g/dL. These results suggest that 6D10-1-1 antibody and 10D5-2-3 antibody are more excellent in the binding activity to BMP9 and the erythropoietic activity than R&D antibody.

Example 15

Activity of Obtained Antibody on Erythropoiesis in normal BALB/c mouse (Long-Term Administration)

The effects of long-term administration of 6D10-1-1 antibody and 10D5-2-3 antibody on erythropoiesis were evaluated using BALB/c mouse. 6-week-old male BALB/c mice were purchased from Charles River Laboratories Japan Inc., and provided for experiment. Sterile tap water was used as drinking water, and solid feed FR-2 (manufactured by Funabashi Farm) was provided as diet with free access.

After pre-breeding, mice were divided into 3 groups (n=8 per group) based on body weight, and allowed free access to a high fat diet (HFD-32; manufactured by CLEA Japan). Subsequently, 6D10-1-1 antibody or 10D5-2-3 antibody was administered at a dose of 1 mg/kg by subcutaneous injection. In detail, each antibody was prepared in a concentration of 0.1 mg/mL using physiological saline, and each was administered at a dose of 10 mL/kg. The vehicle group was administered with physiological saline at a dose of 10 mg/kg by subcutaneous injection.

The antibody or vehicle was administered once a week in total 8 times. 8 weeks after first administration, laparotomy was performed under isoflurane anesthesia, and blood was collected from the postcaval vein, a part of them was put in an EDTA-containing tube, and used as a blood sample. The remaining blood sample was used as a serum sample.

The number of blood cells and the concentration of hemoglobin in the blood samples thus obtained were determined using an automated blood cell counter Celltac α (manufactured by Nihon Kohden Corporation). The results are shown in FIGS. 7A and 7B.

Figure 7A:
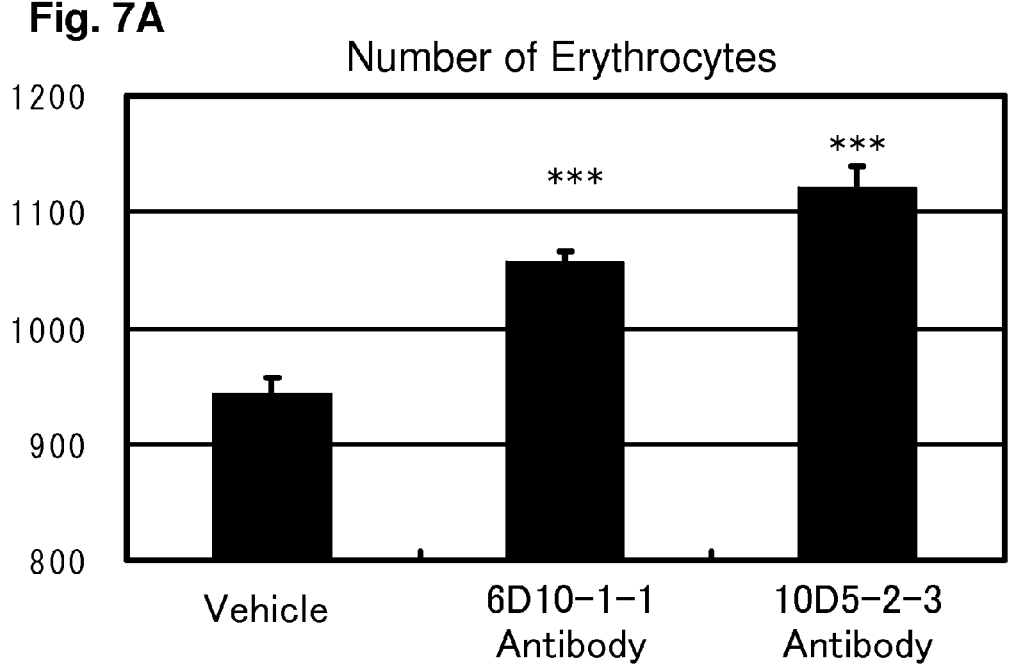
FIG. 7A shows the effect of the obtained anti-BMP9 monoclonal antibody on mouse erythropoiesis by long-term administration (for 2 months), and the graph of FIG. 7A represents changes in the number of erythrocyte, in which the vertical axis represents the number of erythrocyte ($\times 10^4$/µL). In the drawing, the error bar represents standard error of mean (SE, n=8). Student's t-test is used to test a statistically significant difference in the measured values between the vehicle-treated group and various antibody-treated groups.  represents P<0.01, and * represents P<0.001.
Figure 7B:
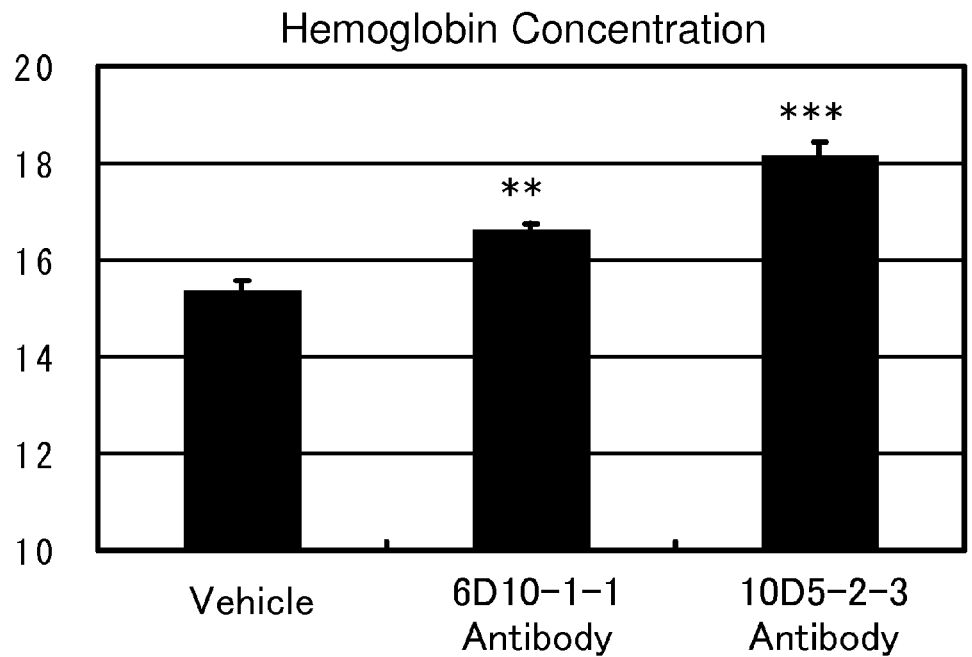
FIG. 7B shows the effect of the obtained anti-BMP9 monoclonal antibody on mouse erythropoiesis by long-term administration (for 2 months), and the graph of FIG. 7B represents changes in the hemoglobin concentration, in which the vertical axis represents the hemoglobin concentration (g/dL). In the drawing, the error bar represents standard error of mean (SE, n=8). Student's t-test is used to test a statistically significant difference in the measured values between the vehicle-treated group and various antibody-treated groups.  represents P<0.01, and * represents P<0.001.

As shown in FIGS. 7A and 7B, the number of erythrocyte and the concentration of hemoglobin were significantly increased by administration of 6D10-1-1 antibody or 10D5-2-3 antibody, and 6D10-1-1 antibody and 10D5-2-3 antibody showed persistent erythropoietic activities by long-term administration (for two months) as well as short-term administration. None of the antibodies affected the body weight.

Subsequently, in order to examine whether or not the erythropoietic activity of anti-human BMP9 antibody is mediated by the blood erythropoietin (EPO) as an erythropoiesis-stimulating factor, the blood EPO concentration in the serum sample was determined using a Quantikine Mouse/Rat Erythropoetin ELISA kit (manufactured by R&D systems). The results are shown in FIG. 8.

Figure 8:
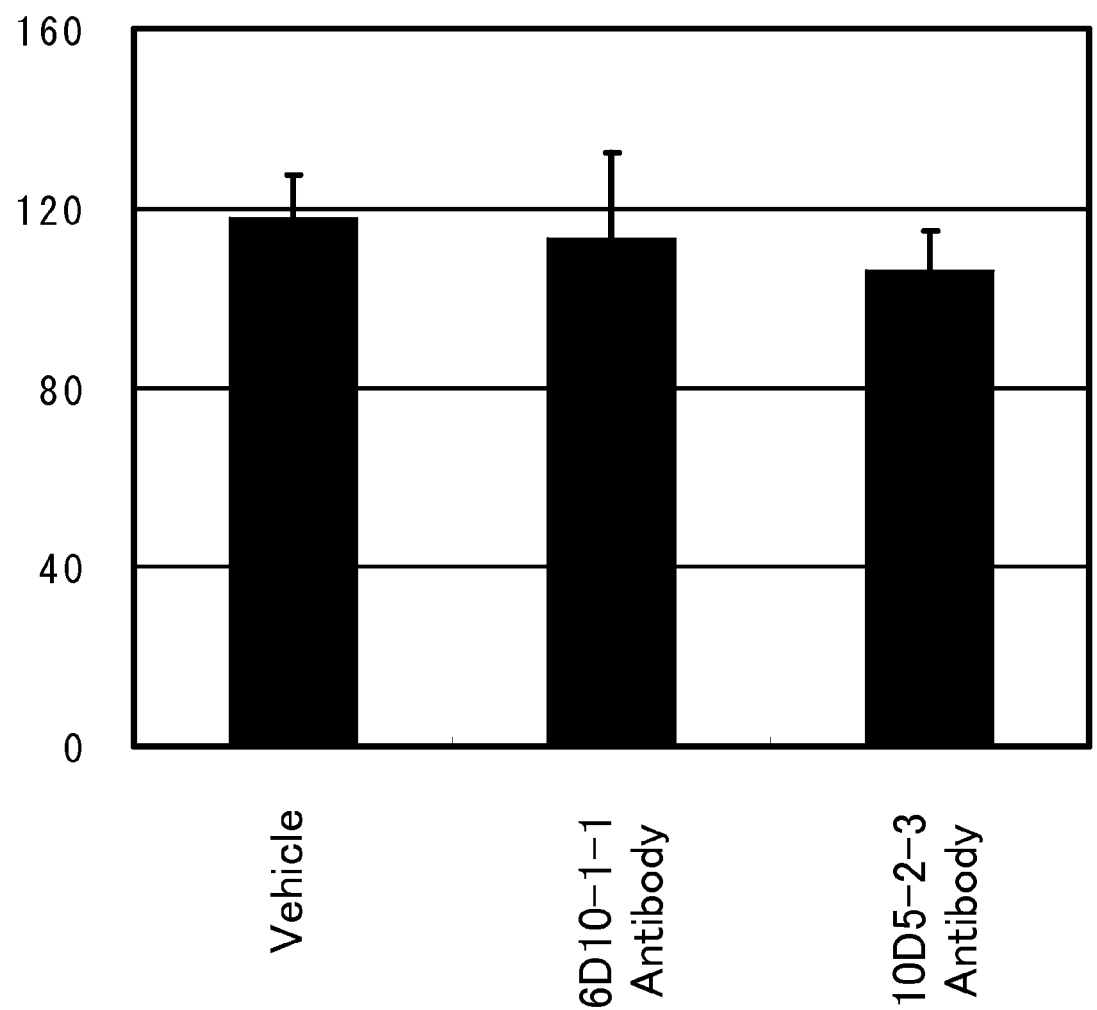
FIG. 8 shows the effect of the obtained anti-BMP9 monoclonal antibody on the blood erythropoietin (EPO) concentration in mice by long-term administration, in which the vertical axis represents mouse EPO concentration (pg/mL). In the drawing, the error bar represents standard error of mean (SE, n=8).

As shown in FIG. 8, the blood EPO concentration tended to decrease by administration of anti-human BMP9 antibody, and no significant change was observed, suggesting that the erythropoietic activity of anti-human BMP9 antibody is not mediated by the increase in EPO production.

Example 16

Activity of Anti-Human BMP9 Antibody on Erythropoiesis in Different Mouse Strains The erythropoietic activity of 10D5-2-3 antibody was evaluated using mice other than BALB/c mouse. CBA/J and ICR mice were used as the mice other than BALB/c mouse. 7-week-old male mice were purchased from Charles River Laboratories Japan Inc., and provided for experiment. Sterile tap water was used as drinking water, and solid feed FR-2 (manufactured by Funabashi Farm) was provided as diet with free access.

After pre-breeding, mice were divided into 2 groups (n=6 per group) based on body weight, and 10D5-2-3 antibody was administered at a dose of 1 mg/kg by subcutaneous injection. In detail, 10D5-2-3 antibody was prepared in a concentration of 0.1 mg/mL using physiological saline, and administered at a dose of 10 mL/kg. The vehicle group was administered with physiological saline at a dose of 10 mg/kg by subcutaneous injection.

The antibody or vehicle was administered once a week in total twice. 14 days after first administration, laparotomy was performed under isoflurane anesthesia, and blood was collected from the postcaval vein, a part of them was put in an EDTA-containing tube, and used as a blood sample. The remaining blood sample was used as a serum sample.

The number of blood cells and the concentration of hemoglobin in the blood samples thus obtained were determined using the automated blood cell counter Celltac α (manufactured by Nihon Kohden Corporation). As a result, with respect to BALB/c, CBA/J, and ICR, the vehicle group showed the number of erythrocyte ($\times 10^4/\mu L$) of 958±8.0, 789±25.3, and 717±22.9 (mean±standard error), respectively, whereas the 10D5-2-3 antibody-treated group showed the number of erythrocyte ($\times 10^4/\mu L$) of 1028±18.1, 853±8.1, and 777±13.2 (mean±standard error), respectively. The increase in the number of erythrocyte by treatment of 10D5-2-3 antibody was 70, 64 and 60, respectively.

With respect to BALB/c, CBA/J, and ICR, the vehicle group showed the hemoglobin concentration (g/dL) of 15.4±0.16, 12.9±0.13, and 13.1±0.50 (mean±standard error), respectively, whereas the 10D5-2-3 antibody-treated group showed the hemoglobin concentration (g/dL) of 16.6±0.26, 13.6±0.13, and 13.7±0.25 (mean±standard error), respectively. The increase in the hemoglobin concentration by treatment of 10D5-2-3 antibody was 1.2, 0.7 and 0.6, respectively.

In all mice, the 10D5-2-3 antibody was recognized to have the erythropoietic activity, suggesting that the anti-human BMP9 antibody exhibits the erythropoietic activity regardless of mouse strains.

Subsequently, in order to examine whether or not the erythropoietic activity of 10D5-2-3 antibody is mediated by EPO increase, the blood EPO concentration in the obtained serum sample was determined using a Quantikine Mouse/Rat Erythropoetin ELISA kit (manufactured by R&D systems).

With respect to BALB/c, CBA/J, and ICR, the vehicle group showed the blood EPO concentration (pg/mL) of 88.5±8.7, 181.2±28.5, and 291.5±106.4 (mean±standard error), respectively, whereas the 10D5-2-3 antibody-treated group showed the blood EPO concentration (pg/mL) of 77.6±5.7, 126.1±20.1, and 236.2±46.1 (mean±standard error), respectively. The decrease in the blood EPO concentration by treatment of 10D5-2-3 antibody was 10.9, 55.1 and 55.3, respectively.

These results suggest that the erythropoietic activity of 10D5-2-3 antibody is not mediated by the increase in EPO production, which are consistent with the results of Example 15.

Example 17

Activity of Obtained Antibodies on Erythropoiesis in Normal Rat

The erythropoietic activities of 6D10-1-1 antibody and 10D5-2-3 antibody in rats were evaluated using Wistar rat. 5-week-old male Wistar rats (CLEA (Japan)) were purchased and provided for experiment. Sterile tap water was used as drinking water, and solid feed FR-2 (manufactured by Funabashi Farm) was provided as diet with free access.

After pre-breeding, rats were divided into 4 groups (n=6 per group) based on body weight, and 6D10-1-1 antibody, 10D5-2-3 antibody or R&D antibody was administered at a dose of 1 mg/kg by subcutaneous injection. In detail, each antibody was prepared in a concentration of 0.5 mg/mL using physiological saline, and administered at a dose of 2 mL/kg.

The vehicle group was administered with physiological saline at a dose of 2 mg/kg by subcutaneous injection.

The antibody or vehicle was administered once a week in total twice. 2 weeks after first administration, laparotomy was performed under isoflurane anesthesia, and blood was collected from the abdominal aorta, a part of them was put in an EDTA-containing tube, and used as a blood sample. The remaining blood sample was used as a serum sample.

The number of blood cells and the concentration of hemoglobin in the blood samples thus obtained were determined using the automated blood cell counter Celltac α (manufactured by Nihon Kohden Corporation). The results are shown in FIGS. 9A and 9B.

Figure 9A:
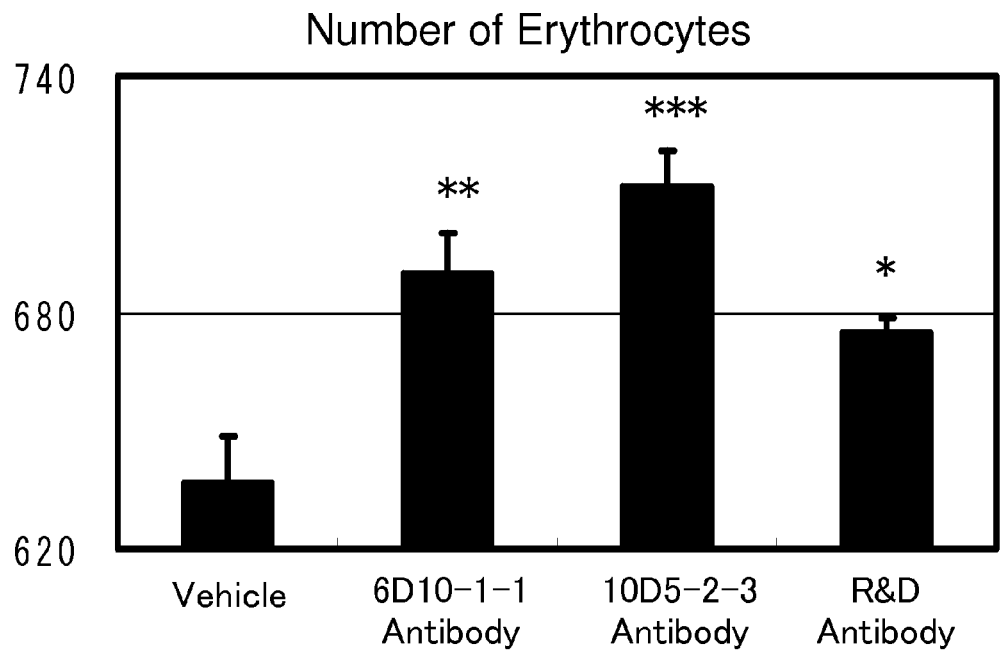
FIG. 9A shows the effect of the obtained anti-BMP9 monoclonal antibody on rat erythropoiesis by short-term administration (for 2 weeks), and the graph of FIG. 9A represents changes in the number of erythrocyte, in which the vertical axis represents the number of erythrocyte ($\times 10^4/\mu L$). In the drawing, the error bar represents standard error of mean (SE, n=6). Student's t-test is used to test a statistically significant difference in the measured values between the vehicle-treated group and various antibody-treated groups. * represents P<0.05,  represents P<0.01, and * represents P<0.001.
Figure 9B:
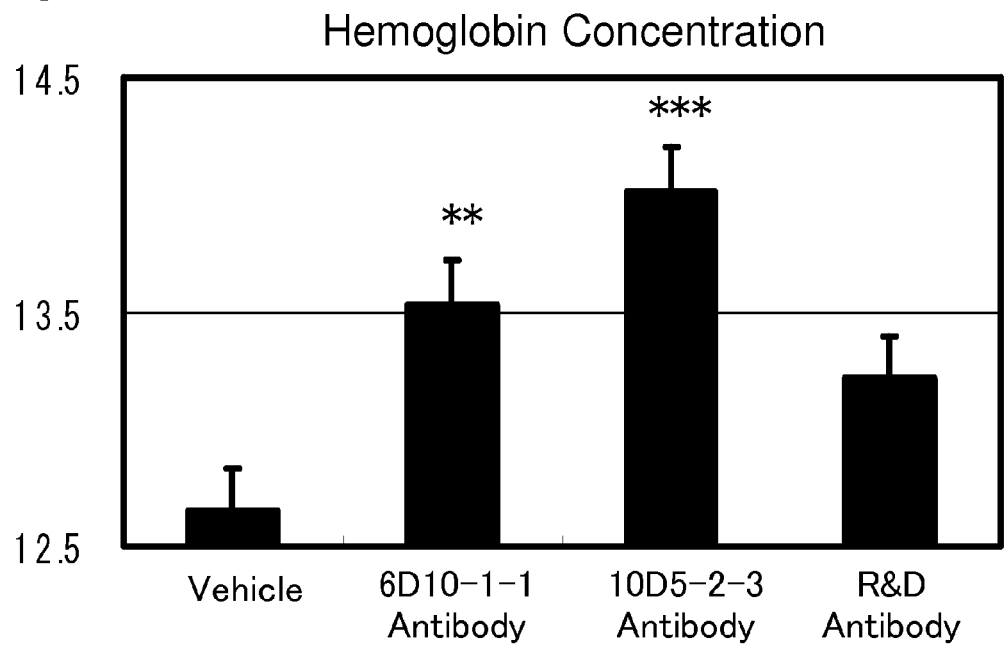
FIG. 9B shows the effect of the obtained anti-BMP9 monoclonal antibody on rat erythropoiesis by short-term administration (for 2 weeks), and the graph of FIG. 9B represents changes in the hemoglobin concentration, in which the vertical axis represents the hemoglobin concentration (g/dL). In the drawing, the error bar represents standard error of mean (SE, n=6). Student's t-test is used to test a statistically significant difference in the measured values between the vehicle-treated group and various antibody-treated groups. * represents P<0.05,  represents P<0.01, and * represents P<0.001.

As shown in FIGS. 9A and 9B, the number of erythrocyte and the concentration of hemoglobin were increased by administration of any of the anti-human BMP9 antibodies, indicating that anti-human BMP9 antibody exhibits the erythropoietic activity in rats as well as mice. It was also recognized that 6D10-1-1 antibody and 10D5-2-3 antibody exhibit stronger erythropoietic activity than R&D antibody in rats as well as mice.

Example 18

Activity of Human BMP9 Antibody on Anemia in Rat with Renal Failure

The activity of 6D10-1-1 antibody and 10D5-2-3 antibody on renal anemia were evaluated using Wistar rats with renal failure, which had undergone 5/6 nephrectomy. 5-week-old male Wistar rats (CLEA (Japan)) were purchased and provided for experiment. Sterile tap water was used as drinking water, and solid feed FR-2 (manufactured by Funabashi Farm) was provided as diet with free access.

After pre-breeding, the left kidney was first exposed via the left dorsal incision under pentobarbital anesthesia, and 2/3 of the kidney was excised. After cessation of bleeding, the excision site was sutured. 1 week later, the right kidney was sutured and excised via the right dorsal incision under pentobarbital anesthesia of the rat, so as to prepare rats with 5/6 nephrectomy. A normal control group was subjected to only dorsal incision and suture as pseudo-operation.

2 weeks after 5/6 nephrectomy, blood was collected from the tail vein of each unanesthetized rat, and a part of them was put in an EDTA-containing tube, and used as a blood sample. The remaining blood sample was used as a serum sample.

The number of blood cells and the concentration of hemoglobin in the blood samples thus obtained were determined using the automated blood cell counter Celltac α (manufactured by Nihon Kohden Corporation).

Subsequently, the concentrations of blood urea nitrogen (BUN) and creatinine in the serum samples thus obtained were determined using a HITACHI Auto Analyzer 7170 (manufactured by Hitachi).

Based on the number of erythrocyte, the concentration of hemoglobin, the concentrations of blood urea nitrogen (BUN) and creatinine, the rats were divided into 3 groups (n=8 per group), so that the difference in the mean value between the groups was as small as possible, and 6D10-1-1 antibody or 10D5-2-3 antibody was administered at a dose of 1 mg/kg by subcutaneous injection.

In detail, each antibody was prepared in a concentration of 0.5 mg/mL using physiological saline, and administered at a dose of 2 mL/kg. The vehicle group was administered with physiological saline at a dose of 2 mL/kg by subcutaneous injection. As the normal control group, the pseudo-operation group (n=5) was administered with the vehicle, physiological saline at a dose of 2 mL/kg.

The antibody or vehicle was administered once a week. 2, 4, 6, and 8 weeks after first administration, blood was collected from the tail vein, and a part of them was put in an EDTA-containing tube, and used as a blood sample. The remaining blood sample was used as a serum sample.

Figure 10A:
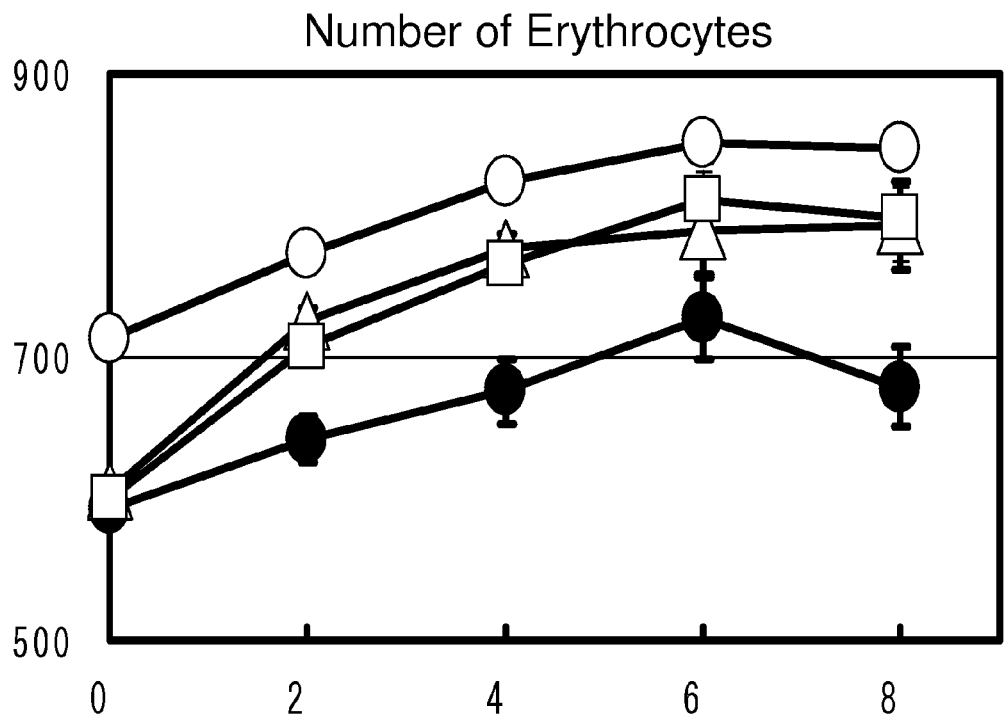
FIG. 10A shows the effect of the obtained anti-BMP9 monoclonal antibody on the renal anemia rat model, and the graph of FIG. 10A represents changes in the number of erythrocyte, in which the horizontal axis represents the elapsed time (week) after antibody administration, and the vertical axis represents the number of erythrocyte ($\times 10^4/\mu L$). The vehicle-treated pseudo-operation group is represented by ○, the vehicle-treated 5/6 nephrectomy group is represented by ●, the 6D10-1-1 antibody-treated 5/6 nephrectomy group is represented by Δ, and the 10D5-2-3 antibody-treated 5/6 nephrectomy group is represented by □. In the drawing, the value of 0 mg/kg represents that of the vehicle-treated group, and the error bar represents standard error of mean (SE, vehicle-treated group n=5, other groups n=8).
Figure 10B:
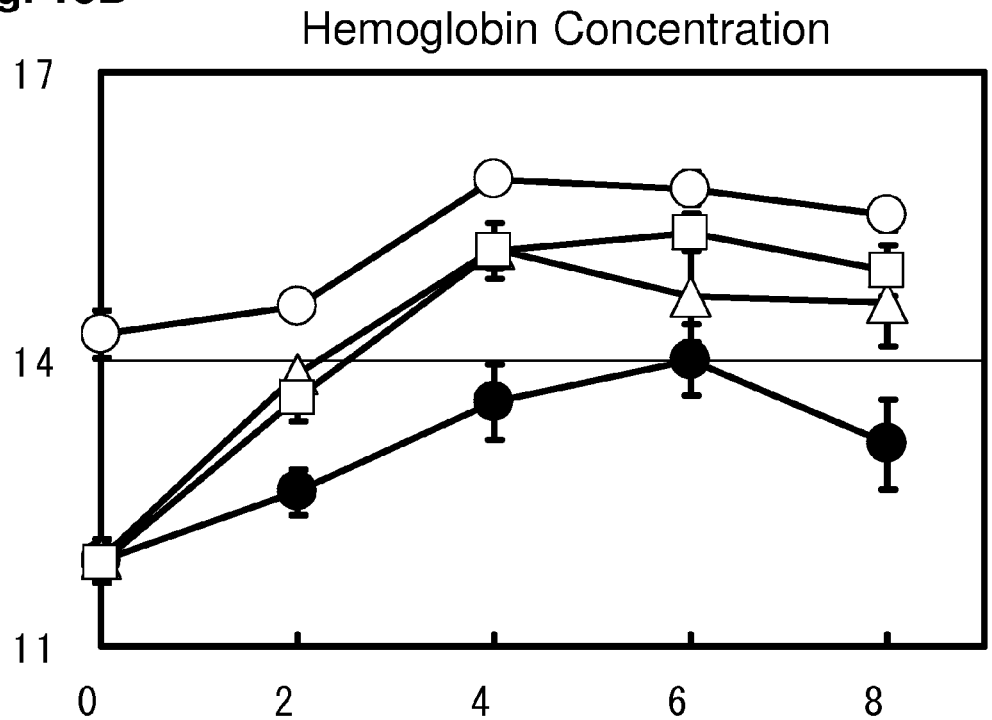
FIG. 10B shows the effect of the obtained anti-BMP9 monoclonal antibody on the renal anemia rat model, and the graph of FIG. 10B represents changes in the hemoglobin concentration, in which the horizontal axis represents the elapsed time (week) after antibody administration, and the vertical axis represents the hemoglobin concentration (g/dL). The vehicle-treated pseudo-operation group is represented by ○, the vehicle-treated 5/6 nephrectomy group is represented by ●, the 6D 10-1-1 antibody-treated 5/6 nephrectomy group is represented by Δ, and the 10D5-2-3 antibody-treated 5/6 nephrectomy group is represented by □. In the drawing, the value of 0 mg/kg represents that of the vehicle-treated group, and the error bar represents standard error of mean (SE, vehicle-treated group n=5, other groups n=8).

The number of blood cells and the concentration of hemoglobin in the blood samples thus obtained were determined using the automated blood cell counter Celltac α (manufactured by Nihon Kohden Corporation). The results are shown in FIGS. 10A and 10B. Further, Student's t-test was used to test a statistically significant difference in the measured values between 5/6 nephrectomy rats administered with the vehicle and those administered with various antibodies. P<0.05 was considered significant.

As shown in FIGS. 10A and 10B, the number of erythrocyte and the concentration of hemoglobin were decreased in the 5/6 nephrectomy rats administered with the vehicle, compared to the pseudo-operation group administered with the vehicle, throughout the experimental period from 0 to 8 weeks. From 2 weeks to 8 weeks after antibody administration, the number of erythrocyte and the concentration of hemoglobin were significantly increased in the 5/6 nephrectomy rats administered with 6D10-1-1 antibody or 10D5-2-3 antibody, excluding in the sample administered with 610D-1-1 antibody 6 weeks after antibody administration, compared to the 5/6 nephrectomy rats administered with the vehicle. None of the antibodies affected the body weight.

These results revealed that 6D10-1-1 antibody and 10D5-2-3 antibody have the activity of improving renal anemia.

Example 19

Isolation of Gene Sequences Encoding VH and VL of Anti-Human BMP9 Monoclonal Antibody 19-1) Preparation of total RNAs from Anti-Human BMP9 Monoclonal Antibody-Producing Hybridoma Cells Total RNAs were prepared from $1 \times 10^6$ of hybridomas producing 6D 10-1-1 antibody, 10D5-2-3 antibody and 3B7-3-3 antibody described in Example 7 using an RNAeasy Mini Kit (manufactured by QIAGEN, Cat#74104) and a QIA shredder (manufactured by QIAGEN, Cat#79654).

19-2) Cloning of Genes Encoding VH and VL of Anti-Human BMP9 Monoclonal Antibody cDNA was synthesized from 1 μg of the total RNA of each hybridoma obtained in Example 19-1 using a SMARTer RACE cDNA Amplification Kit (manufactured by Clontech, Cat#634924). cDNA sequence of VH was determined using the obtained cDNA as a template, a universal primer A mix (containing forward primers) in the kit, and two different reverse primers specific to heavy chain constant regions of mouse IgG1, IgG2a, IgG2b, and IgG2c in combinations.

In detail, PCR was performed using primers specific to mouse IgG1 (SEQ ID NOs:17 and 18), primers specific to mouse IgG2a (SEQ ID NOs:19 and 20), primers specific to mouse IgG2b (SEQ ID NOs:21 and 22), primers specific to mouse IgG2c (SEQ ID NO.23), or primers specific to mouse IgG3 (SEQ ID NOs:24 and 25), and the universal primer A in combinations, so as to amplify the cDNA fragment of VH of each antibody.

In addition, PCR was performed using primers specific to mouse Ig(κ) (SEQ ID NOs:26 and 27) or primers specific to mouse Ig(λ) (SEQ ID NOs:28 and 29) and the universal primer A in combinations, so as to amplify the cDNA fragment of VL of each antibody.

PCR was performed for 5 cycles consisting of 94° C. for 30 seconds and 72° C. for 3 minutes, 5 cycles consisting of 94° C. for 30 seconds, 70° C. for 30 seconds, and 72° C. for 3 minutes, and 25 cycles consisting of 94° C. for 30 seconds, 68° C. for 30 seconds, and 72° C. for 3 minutes.

As a result of agarose gel electrophoresis, PCR products of cDNAs derived from hybridomas producing 6D10-1-1 antibody, 10D5-2-3 antibody and 3B7-3-3 antibody were obtained when the primers specific to IgG1 heavy chain constant region were used.

PCR products of cDNAs derived from both hybridomas were also obtained when the primers specific to mouse Ig(κ) were used. Each PCR product was purified using a Gel Extraction Kit (manufactured by QIAEX II, QIAGEN, Cat#20021).

Each of the gene fragments thus obtained was inserted into a pCR4 vector (manufactured by Invitrogen) using a Zero Blunt TOPO PCR Cloning Kit for Sequencing (manufactured by Invitrogen, Cat#K287540SP).

The plasmid thus obtained was introduced into *E. coli* DH5α. Plasmids were extracted from the transformants using an auto-plasmid-isolator (manufactured by KURABO), followed by sequencing analysis. As a result, it was found that full-length VH cDNA and VL cDNA including the putative ATG initiation codon at the 5'-terminus were obtained.

19-3) Analysis of V Region Sequence of Anti-Human BMP9 Monoclonal Antibody

The entire base sequences of VHs of 6D10-1-1 antibody, 10D5-2-3 antibody, 3B7-3-3 antibody, obtained in Example 19-2, are represented by SEQ ID NOs:30, 31, and 32, respectively and the entire amino acid sequences thereof including the signal sequence, deduced from these base sequences, are represented by SEQ ID NOs:33, 34, and 35, respectively. The entire base sequences of VLs thereof are represented by SEQ ID NOs:36, 37, and 38, respectively and the entire amino acid sequences thereof including the signal sequence, deduced from these base sequences, are represented by SEQ ID NOs: 39, 40, and 41, respectively.

The base sequences excluding the signal sequence from SEQ ID NOs:30, 31, and 32 are represented by SEQ ID NOs:42, 43, and 44, respectively. The base sequences excluding the signal sequence from SEQ ID NOs:36, 37, and 38 are represented by SEQ ID NOs:45, 46, and 47, respectively. The amino acid sequences excluding the signal sequence from SEQ ID NOs:33, 34, and 35 are represented by SEQ ID NOs:48, 49, and 50, respectively. The amino acid sequences excluding the signal sequence from SEQ ID NOs:39, 40, and 41 are represented by SEQ ID NOs:51, 52, and 53, respectively.

Compared to the known sequence data of mouse antibody [SEQUENCES of Proteins of Immunological Interest, US Dept. Health and Human Services (1991)], the isolated cDNAs are found to be full-length cDNAs including the secretory signal sequence, which encode 6D10-1-1 antibody, 10D5-2-3 antibody, and 3B7-3-3 antibody, respectively.

CDRs of VH and VL of each monoclonal antibody were identified by comparison with the known antibody amino acid sequence. The amino acid sequences of CDR1, CDR2 and CDR3 of VH of 6D10-1-1 antibody are represented by SEQ ID NOs:54, 55 and 56, respectively. The amino acid sequences of CDR1, CDR2 and CDR3 of VL thereof are represented by SEQ ID NOs:57, 58 and 59, respectively.

The amino acid sequences of CDR1, CDR2 and CDR3 of VH of 10D5-2-3 antibody are represented by SEQ ID NOs: 60, 61 and 62, respectively. The amino acid sequences of CDR1, CDR2 and CDR3 of VL thereof are represented by SEQ ID NOs:63, 64 and 65, respectively.

Example 20

Analysis of Epitope of Obtained Antibody 20-1) Recombinant Expression of Obtained Antibody The base sequences of light chain and heavy chain variable regions (containing signal sequence) of 6D10-1-1 antibody and 10D5-2-3 antibody were bound to the base sequences of light chain (κ chain) and heavy chain (IgG1) constant regions of mouse, respectively. Each of the resultants was subcloned into an antibody-expression vector. Amplification of the base sequence of variable region of BMP9 antibody was performed by PCR using the plasmid of Example 19 as a template and primers represented by SEQ ID NOs:72 to 79, respectively.

Amplification of the base sequences of light chain (κ chain) and heavy chain (IgG1) constant regions of mouse was performed by PCR using the artificial synthetic sequences represented by SEQ ID NOs:80 and 81 (manufactured by TakaraBio) as a template and primers represented by SEQ ID NOs:82 to 85, respectively.

For All PCR, PrimeSTAR HS (Premix) (manufactured by TakaraBio, R040A) was used, and incubation was performed at 96° C. for 2 minutes, followed by 30 cycles consisting of 98° C. for 10 seconds, 55° C. for 5 seconds, and 72° C. for 1 to 2 minutes (depending on the product size). The PCR products thus obtained was subjected to agarose gel electrophoresis, purified using a QIAquick Gel Extraction Kit (manufactured by Qiagen), and used as an insert.

An N5KG1 vector (manufactured by Biogen IDEC) was digested with BglII and EcoRI, and purified in the same manner as above, and used as a vector for insertion.

The light chain variable region of 6D 10-1-1 antibody and the light chain constant region of mouse were inserted into the enzyme-treated N5KG1 vector using In-fusion Advantage PCR Cloning Kit (manufactured by TakaraBio), and transformed into *E. coli*.

Clones having the accurate insert sequence were selected from the obtained transformants. The plasmid DNA was digested with SalI and BamHI, and purified in the same manner as above. The heavy chain variable region of 6D10-1-1 antibody and the heavy chain constant region of mouse were inserted into the above vector, to which the light chains had been previously inserted, and transformed into *E. coli*.

Clones having the accurate insert sequence were selected from the obtained transformants. 10D5-2-3 antibody expression vector was also prepared in the same manner as in the 6D 10-1-1 antibody expression vector. The light chain variable region was inserted between BglII and BsiWI restriction sites, and the heavy chain variable region was inserted between SalI and NheI restriction sites.

*E. coli* was transformed with the 6D10-1-1 antibody- or 10D5-2-3 antibody-expression vector, and these vectors were prepared using a NucleoBond Xtra Maxi (manufactured by TakaraBio). Transient expression was performed using the FreeStyle 293 Expression System (manufactured by Life Technologies) to express the recombinant antibodies. The culture supernatant was obtained from the culture broth by centrifugation and filtration using a 0.22 μm filter.

Subsequently, antibodies were purified by affinity chromatography using Protein Sepharose 4 Fast Flow (manufactured by GE Healthcare). A NAP-25 column (manufactured by GE Healthcare) was used to replace the buffer with citrate buffer (10 mM citric acid-NaOH (pH 6.0), 150 mM NaCl). Absorbance at 280 nm was measured to determine the concentration. The absorption coefficient was 1.4 mL/(mg·cm).

20-2) Preparation of Human BMP9/BMP10 Chimeric Protein

The amino acid sequence represented by SEQ ID NO:86 in the human BMP9 mature region is defined as human BMP9 region C, and the amino acid sequence represented by SEQ ID NO:139 in the human BMP10 mature region is defined as human BMP10 region C.

Human BMP10 is a molecule having the highest homology to human BMP9, but the 6D10-1-1 antibody, 10D5-2-3 antibody and R&D antibody do not have the cross-reactivity to BMP10. Of the amino acid residues included in the human BMP9 region C, those different from the human BMP10 region C are Ser at position 80, Val at position 84, Lys at position 87, Asp at position 89, Met at position 90, Pro at position 93, Leu at position 95, Tyr at position 97, His at position 98, Ser at position 103, and Ala at position 105 in the human BMP9 mature region represented by SEQ ID NO:67.

Based on the difference in the region C, the amino acid residues of BMP9 were replaced by the corresponding amino acid residues of BMP10 so as to design chimeric proteins 1 to 5 of human BMP9/10.

Chimeric protein 1 was prepared by replacing the amino acid residues at positions 87, 89, and 93 with Leu, Lys, and Val, respectively and deleting the amino acid residue at position 90 in the mature region of human BMP9. Chimeric protein 2 was prepared by replacing the amino acid residues at positions 84, 95, 97 and 98 with Ile, Tyr, Phe and Lys, respectively in the mature region of human BMP9.

Chimeric protein 3 was prepared by replacing the amino acid residues at positions 80, 103 and 105 with Glu, Ala and Ser, respectively in the mature region of human BMP9. Chimeric protein 4 was prepared by replacing the amino acid residues at positions 84, 87, 89, 93, 95, 97 and 98 with Ile, Leu, Lys, Val, Tyr, Phe and Lys, respectively and deleting the amino acid residue at position 90 in the mature region of human BMP9.

Chimeric protein 5 was prepared by replacing the amino acid residues at positions 80, 84, 95, 97, 98, 103 and 105 with Glu, Ile, Tyr, Phe, Lys, Ala and Ser, respectively in the mature region of human BMP9. In chimeric proteins 1 to 5, the amino acid sequences corresponding to human BMP9 region C and human BMP10 region C are represented by SEQ ID NOs:78 to 91.

An N-terminal His-tagged hBMP9 complex recombinant expression vector (hereinafter, referred to as pLN1V5_human BMP9 vector) described in Example 12 and FIG. 7 of WO 2010/126169 was digested with StuI and XhoI, and subjected to agarose gel electrophoresis, and then purified using a QIAquick Gel Extraction Kit (manufactured by QIAGEN).

To prepare chimeric proteins 1 to 5 of human BMP9/10 region C, Fwd and Rv primers for chimeric protein construction represented by SEQ ID NOs:92 to 101 were mixed and hybridized in combinations of 1/6, 2/7, 3/8, 4/9, and 5/10, and then inserted into the purified vector using an In-fusion HD Cloning Kit (manufactured by TakaraBio, Z9649N).

Further, a pLN1V5_human BMP10 vector was prepared by the following procedure. The pLN1V5_human BMP9 vector was digested with NheI and XhoI, and subjected to agarose gel electrophoresis, and then purified using the QIAquick Gel Extraction Kit (manufactured by QIAGEN).

PCR was performed using Human Heart PCR-Ready cDNA (manufactured by Ambion, 3326) as a template and primers of Fwd-1/Rv-1 and Fwd-2/Rv-2 represented by SEQ ID NOs:102 to 105.

For PCR, PrimeSTAR HS (Premix) (manufactured by TakaraBio, R040A) was used, and incubation was performed at 96° C. for 2 minutes, followed by 32 cycles consisting of 98° C. for 10 seconds, 55° C. for 5 seconds, and 72° C. for 2 minutes.

The two PCR products thus obtained were subjected to agarose gel electrophoresis, and then purified using a QIAquick Gel Extraction Kit (manufactured by Qiagen), and used as the inserts. Subcloning was performed by inserting the inserts into the previously purified pLN1V5 vector using an In-fusion HD Cloning Kit, so as to give a pLN1V5_human BMP10 vector.

The amino acid sequences and base sequences of human BMP10 and the mature region thereof are represented by SEQ ID NOs:106 to 109. The amino acid sequence and base sequence of the N-terminal His-tagged BMP10 expressed by the pLN1V5_human BMP10 vector are represented by SEQ ID NOs:110 and 111.

*E. coli* was transformed with the pLN1V5_human BMP10 vector prepared in the previous section and the pLN1V5_human BMP9 vector, and the vectors were prepared using the NucleoBond Xtra Maxi (manufactured by TakaraBio).

Transient expression was performed using the FreeStyle 293 Expression System (manufactured by Life Technologies) to express human BMP9, human BMP10, and chimeric proteins 1 to 5 of human BMP9/10 region C.

The culture supernatant was obtained from the culture broth by centrifugation and filtration using a 0.22 μm filter. Subsequently, each protein was purified using Ni-NTA Agarose (manufactured by QIAGEN). 20 mM HEPES-NaOH (pH 7.4), 500 mM NaCl and 40 mM imidazole was used as a binding buffer, and 20 mM HEPES-NaOH (pH 7.4), 500 mM NaCl and 200 mM imidazole was used as an elution buffer. The NAP-25 column (manufactured by GE Healthcare, 17-0852-02) was used to replace the buffer with PBS.

Absorbance at 280 nm was measured to determine the concentration of each protein solution. The absorption coefficients for human BMP9 and human BMP10 were 1.05 and 0.96 mL/(mg·cm), respectively. The absorption coefficient for chimeras 1 to 5 was 1.055 mL/(mg·cm).

20-3) Specific Binding Properties of Obtained Antibodies to Chimeric Proteins

Antigen immobilized ELISA of the obtained antibodies was performed using the chimeric protein. 3 μg/mL of the recombinant human BMP9, BMP10, and BMP9/10 chimeric proteins of Example 20-2 in 50 mmol/L NaHCO₃ buffer were added to a 96-well plate for ELISA (F96 MAXISORP NUNC-IMMUNO PLATE, manufactured by Thermo Fisher Scientific, Cat#442404) at an amount of 50 μL/well, and left at 4° C. overnight for adsorption.

After removal of the reagent for immobilization, 200 μL/well of 1% BSA-PBS was added, and left at room temperature for 1 hour for blocking, and washing was carried out using PBST five times. Subsequently, 1000 ng/mL of the obtained antibody (prepared in Example 20-1), R&D antibody, BMP10 antibody (manufactured by R&D, MAB2926), BMP9 goat polyclonal antibody (manufactured by R&D, AF3209), or the negative control mouse IgG1 or IgG2b monoclonal antibody (MAB002, MAB004 (both manufactured by R&D)) prepared in 1% BSA-PBS was added in an amount of 50 μL/well, and left at room temperature for 1 hour.

This plate was washed with PBST 5 times, and then 50 μL/well of goat anti-mouse IgG HRP (manufactured by DAKO, P0447) or rabbit anti-goat IgG HRP (manufactured by DAKO, P0160) which was a 2000-fold dilution in 1% BSA-PBS was aliquoted and left at room temperature for 1 hour.

The plate was washed with PBST ten times, and 50 μL/well of the TMB chromogen reagent (TMB+ Substrate-Chromogen, manufactured by Dako, Cat#S 1599) was added for chromogenic reaction. When the intensity of chromogenic reaction became strong enough, 50 μL/well of a 1 N sulfuric acid solution (manufactured by Wako, Cat#192-04755) was added, and absorbance at 450 nm and 570 nm was determined using a Multiskan Spectrum (manufactured by Thermo Labsystems).

The results are given in Table 2. With respect to + and − in Table, absorbance of 1 or more was indicated as +, and absorbance of less than 1 was indicated as −.

TABLE 2

| Antibody | Human BMP9 | Human BMP10 | Chimera 1 | Chimera 2 | Chimera 3 | Chimera 4 | Chimera 5 |
|---|---|---|---|---|---|---|---|
| Mouse IgG1 control antibody | − | − | − | − | − | − | − |
| Mouse IgG2b control antibody | − | − | − | − | − | − | − |
| BMP9 goat polyclonal antibody | + | − | + | + | + | + | + |
| 6D10-1-1 antibody | + | − | + | − | + | − | − |
| 10D5-2-3 antibody | + | − | − | + | + | − | + |
| R&D antibody | + | − | + | − | + | − | − |
| BMP10 antibody | − | + | − | − | − | − | − |

As shown in Table 2, BMP9 goat polyclonal antibody that was used to confirm the presence of a proper amount of immobilized antigen bound to human BMP9 and all chimeric proteins 1 to 5, which indicates a sufficient amount of immobilized antigen was on the plate.

Meanwhile, it was found that 6D10-1-1 antibody and R&D antibody specifically bound to chimeric protein 1 and chimeric protein 3, whereas 10D5-2-3 antibody specifically bound to chimeric protein 2, chimeric protein 3, and chimeric protein 5.

These results indicate that 6D 10-1-1 antibody and R&D antibody bind to at least Val at position 84, Leu at position 95, Tyr at position 97, and H is at position 98 in the human BMP9 mature region, and 10D5-2-3 antibody binds to at least Lys at position 87, Asp at position 89, Met at position 90, and Pro at position 93 in the human BMP9 mature region. Taken together, it was revealed that 10D5-2-3 antibody is an antibody recognizing a BMP9 epitope different from that recognized by the conventional R&D antibody.

Example 21

Inhibitory Effect of Complex of BMP9 and Obtained Antibody on BMP10 Signaling

The results of Examples 11 and 12 showed that 10D5-2-3 antibody and 6D10-1-1 antibody do not inhibit binding of human BMP9 and human ALK1, but specifically inhibit binding of human BMP9 and human BMPRII.

Further, the result of Example 20 showed that the BMP9 epitopes of 10D5-2-3 antibody and 6D10-1-1 antibody are different from each other. In addition to BMP9, BMP10 is also known as a ligand of the ALK1 receptor. It was assumed that a complex of BMP9 and 6D10-1-1 antibody or 10D5-2-3 antibody binds to ALK1 so as to inhibit binding of BMP10 to ALK1, leading to attenuation of BMP10-ALK1 signaling.

In order to investigate this assumption, a human ALK1-expressing reporter cell line was prepared, and inhibitory effect of the complex of BMP9 and the obtained antibody on human BMP10-dependent human ALK1 signaling was evaluated. A difference in the actions between the antibodies attributed to the difference in their epitopes recognized thereby was also investigated.

21-1) Preparation of Human ALK1 Expressing Reporter Cell Line

The human ALK1 expression reporter cell was prepared by forced expression [ALK1/p(GCCG) 12-Luc/HepG2(38.5)] of the full-length human ALK1 gene in the BMP signal detection cell [p(GCCG) 12-Luc/HepG2(38.5)] described in Example 2 of WO 2010/126169.

The full-length cDNA of human ALK1 with EcoRI and NotI restriction sites at both ends was digested with EcoRI and NotI, and then integrated into the pEAK8 expression vector (manufactured by Edgebiosystems) so as to prepare the human ALK1 expression vector. The full-length cDNA of human ALK1 (cDNA Genbank Accession NO. BC042637.1, SEQ ID NO:112, Amino acid sequence GenBank Accession NO. AAH42637, SEQ ID NO:71) was prepared by PCR using a human lung cDNA library and primers (SEQ ID NOs:113 and 114).

21-2) Effect of Complex of Human BMP9 and Obtained Antibodies on BMP10-dependent ALK1 Signaling The human ALK1 reporter cell line [ALK1/p(GCCG) 12-Luc/HepG2(38.5)] prepared by the above method was suspended in a DMEM proliferation medium [DMEM (manufactured by Invitrogen) supplemented with 10% FCS] containing 1 μg/mL of hsALK1-Fc, and seeded in a 96-well white plate (manufactured by PerkinElmer) at a density of $1.5 \times 10^4$/well.

Next day, the wells were washed with 200 μL of serum-free DMEM, and then 100 μL of 0.1% BSA (Bovine serum albumin)-containing DMEM medium added with 2 ng/mL or 10 ng/mL of human mature dimer BMP9 recombinant protein (manufactured by R&D systems, Cat#3209-BP) and 3 μg/mL of 6D10-1-1 antibody or 10D5-2-3 antibody was added thereto.

30 minutes later, each 5 μL of human mature dimer BMP10 recombinant protein (manufactured by R&D systems, Cat#2926-BP-0255) that was prepared at a final concentration of 0.1, 0.3, 1.0, 3.0, or 10 ng/mL using 0.1% BSA (Bovine serum albumin) was added, and the plate was incubated for 6 hours. 6 hours later, 50 μL of a chemiluminescent reagent [Steadyglo Luciferase assay system, manufactured by Promega] was added to determine Luciferase activity. 0.1% BSA-containing DMEM was added to a negative control well. The results are shown in FIG. 11.

As shown in FIG. 11, it was revealed that the complex of human BMP9 and 6D10-1-1 antibody inhibits the BMP10-dependent ALK1 signaling, whereas the complex of human BMP9 and 10D5-2-3 antibody does not inhibit the BMP10-dependent ALK1 signaling. The BMP10-deficient animal test showed that BMP10 is an important molecule in heart development [Development, 131(9), 2219 (2004)], and in terms of side-effects, the anti-BMP9 antibody is required not to affect BMP10 signaling that is important in heart development.

Therefore, it was suggested that 10D5-2-3 antibody is a more preferred anti-BMP9 antibody than 6D 10-1-1 antibody or R&D antibody, in terms of side-effects.

Example 22

Preparation of 10D5-2-3 Chimeric Antibody (c10D5-2-3 antibody) and Humanized Antibody 22-1) Design of Amino Acid Sequences of VH and VL of 10D5-2-3 Humanized Antibody The amino acid sequence of VH of 10D5-2-3 humanized antibody was designed as follows. The amino acid sequences of FRs in VH of human antibody suitable for the grafting of the amino acid sequences of CDR1 to 3 of VH of 10D5-2-3 (SEQ ID NOs:60, 61 and 62) was selected as follow.

First, with respect to the previously known human antibody heavy chain variable region sequence, a human antibody sequence having high homology to the FR sequence in VH of 10D5-2-3 antibody was searched using a database of Ig Germline Genes provided by The National Center for Biotechnology Information. As a result, FR of IGVH3-72 was selected, because IGVH3-72 is a human antibody sequence having the highest homology. The amino acid sequences of CDR1 to 3 of VH of 10D5-2-3 antibody, represented by SEQ ID NOs:60, 61 and 62, were grafted into the proper region of the FR sequence of the human antibody thus determined, so as to design HV0 (SEQ ID NO:116).

Subsequently, the amino acid sequence of VL of 10D5-2-3 antibody-humanized antibody was designed as follows. The amino acid sequences of FRs in VL of human antibody suitable for the grafting of the amino acid sequences (SEQ ID NOs:63, 64 and 65) of CDR1 to 3 of VL of 10D5-2-3 antibody were selected as follow.

Kabat et al., have classified VL of the conventionally known various human antibodies into subgroups (HSGI to IV) based on the homology of their amino acid sequences and reported the consensus sequences for each of the subgroups [Sequences of Proteins of Immunological Interest, US Dept Health and Human Services (1991)]. Therefore, the homology search of the amino acid consensus sequences of FR of VL subgroups I to IV of human antibodies with the amino sequence of FR of VL of 10D5-2-3 antibody was conducted.

As a result of the homology search, the homologies of HSGI, HSGII, HSGIII, and HSGIV were 67.1%, 67.1%, 68.4%, and 75.9%, respectively. Therefore, the amino acid sequence of FR of VL of 10D5-2-3 antibody had the highest homology to the subgroup IV.

Based on the above results, the amino acid sequences of CDR1 to 3 of the VL of 10D5-2-3 antibody (SEQ ID NOs:63, 64 and 65) was grafted to an appropriate position of the FR amino acid sequence of the consensus sequence of subgroup IV of VL of human antibody. However, because Leu at position 108 in the amino acid sequence of VL of 10D5-2-3 antibody (SEQ ID NO:52) is an amino acid residue that is not used with the highest frequency, but is used with the relatively high frequency in the corresponding region of the amino acid sequence of FR of human antibody suggested by Kabat et al., it was decided to use an amino acid residue existing in the amino acid sequence of VL of 10D5-2-3 antibody. In this manner, 10D5-2-3 antibody LV0 (SEQ ID NO:118), i.e., the amino acid sequence of VL of 10D5-2-3 antibody-humanized antibody was designed.

The amino acid sequence of 10D5-2-3 antibody HV0 which was VH of 10D5-2-3 antibody; and the amino acid sequence of 10D5-2-3 antibody LV0 which was VL of 10D5-2-3 antibody designed in the above were the sequences in which only the amino acid sequences of CDRs derived from the mouse monoclonal antibody 10D5-2-3 were grafted into the amino acid sequence of the selected FR of human antibody.

However, in general, it is known that a humanized antibody prepared merely by grafting CDRs of a mouse antibody to FRs of a human antibody has a lower binding activity. In order to avoid decreasing of the binding activity, attempts have been made to modify the amino acid residues which were considered to have influence on the binding activity among the amino acid sequences of FRs of a human antibody which are different from a mouse antibody as well as grafting amino acid sequences of CDRs. Therefore, in Examples, the inventors decided to identify and modify the amino acid residues of FR which were considered to have influence on the binding activity in the following manner.

First, three-dimensional structure of the above designed antibody V region (hereinafter referred to as HV0LV0) including the amino acid sequence of 10D5-2-3 antibody HV0 which was VH of the 10D5-2-3 antibody-humanized antibody and the amino acid sequence of 10D5-2-3 antibody LV0 which was VL of the 10D5-2-3 antibody-humanized antibody was constructed using a computer modeling technique. Discovery Studio (manufactured by Accelrys) was used for preparation of the three-dimensional structure coordinates and display of the three-dimensional structure.

Further, a computer model of the three-dimensional structure of V region of 10D5-2-3 antibody was constructed in the same manner. Furthermore, amino acid residues which were different from those of 10D5-2-3 antibody in the amino acid sequence of FRs of VH and VL of HV0LV0 were selected, and modified with the corresponding amino acid residues of 10D5-2-3 antibody, and then a three-dimensional structure model was constructed in the same manner.

The amino acid residues which were considered to have influence on the binding activity were identified by comparing the three-dimensional structures of the V regions of 10D5-2-3 antibody and HV0LV0 and the modified product.

As a result, as amino acid residues of FR in HV0LV0 which were considered to change the three-dimensional structure of the antigen binding region and have influence on the binding activity, Gly at position 8, Leu at position 18, Gly at position 49, Asn at position 79, Leu at position 81, Ala at position 94, Val at position 95, Ala at position 99, and Arg at position 100 in the amino acid sequence of SEQ ID NO:116 were selected in 10D5-2-3 antibody HV0; and Met at position 4, Tyr at position 40, Ser at position 81, Leu at position 82, Val at position 89, and Tyr at position 91 in the amino acid sequence of SEQ ID NO:118 were selected in 10D5-2-3 antibody LV0.

Among the selected amino acid residues, at least one or more amino acid sequence was modified with amino acid residues which were present at the corresponding sites of 10D5-2-3 antibody, and VHs and VLs of the humanized antibody having various modifications were constructed.

Specifically, as for VH, at least one modification was introduced among the amino acid modifications of substitution of Gly with Arg at position 8, substitution of Leu with Met at position 18, substitution of Gly with Ala at position 49, substitution of Asn with Ser at position 79, substitution of Leu with Val at position 81, substitution of Ala with Gly at position 94, substitution of Val with Ile at position 95, substitution of Ala with Thr at position 99, and substitution of Arg with Gly at position 100 in the amino acid sequence represented by SEQ ID NO:116.

Further, as for VL, at least one modification was introduced among the amino acid modifications of substitution of Met with Leu at position 4, substitution of Tyr with Phe at position 40, substitution of Ser with Pro at position 81, substitution of Leu with Met at position 82, substitution of Val with Met at position 89, and substitution of Tyr with Phe at position 91 in the amino acid sequence represented by SEQ ID NO:118.

As the antibody V region of 10D5-2-3 antibody-humanized antibody in which at least one amino acid existing in FR of HV0LV0 was modified, HV0LV0, HV0LV2, HV0LV3, HV0LV4, HV0LV6, HV9LV0, HV9LV2, HV9LV3, HV9LV4, HV9LV6, HV3LV0, HV4aLV0, HV4bLV0, HV7aLV0, HV3LV2, HV3LV3, HV3LV6, HV4bLV2, HV4bLV3, HV4bLV6, HV7aLV2, and HV7bLV2 were designed.

In the following description, the above mentioned 10D5-2-3 antibody-humanized antibodies including the V region are abbreviated to HV0LV0, HV0LV2, HV0LV3, HV0LV4, HV0LV6, HV9LV0, HV9LV2, HV9LV3, HV9LV4, HV9LV6, HV3LV0, HV4aLV0, HV4bLV0, HV7aLV0, HV3LV2, HV3LV3, HV3LV6, HV4bLV2, HV4bLV3, HV4bLV6, HV7aLV2, and HV7bLV2.

The amino acid sequences of H chain variable region, HV3 (SEQ ID NO:120), HV4a (SEQ ID NO:122), HV4b (SEQ ID NO:124), HV7a (SEQ ID NO:126), HV7b (SEQ ID NO:128), and HV9 (SEQ ID NO:130), and the amino acid sequences of L chain variable region, LV2 (SEQ ID NO:132), LV3 (SEQ ID NO:134), LV4 (SEQ ID NO:136), and LV6 (SEQ ID NO:138) are shown in FIGS. 12 and 13, respectively.

22-2) Design of Variable Region Gene of 10D5-2-3 Antibody-Humanized Antibody

DNA encoding the amino acid sequence of the variable region of the humanized antibody was designed using codons used in the DNAs (SEQ ID NOs:31 and 37) encoding the amino acid sequences of VH of 10D5-2-3 antibody and VL of 10D5-2-3 antibody, respectively. When the amino acid modification was introduced, DNA was designed using a codon which was used in a mammal cell with a high frequency. By using these DNA sequences, antibody expression vectors were constructed and humanized antibodies were expressed.

22-3) Construction of cDNAs encoding VHs of c10D5-2-3 Antibody and Humanized Antibody cDNAs encoding VH of 10D5-2-3 antibody represented by SEQ ID NO:49, the amino acid sequence HV0 of VH of 10D5-2-3 antibody-humanized antibody designed in Example 22-1) (SEQ ID NO:116), and HV3, HV4a, HV4b, HV7a, HV7b, and HV9 designed by the method of Example 22-1) were synthesized by gene synthesis.

22-4) Construction of cDNAs encoding VLs of c10D5-2-3 Antibody and Humanized Antibody cDNAs encoding VL of 10D5-2-3 antibody represented by SEQ ID NO:52, the amino acid sequence LV0 of VL of 10D5-2-3 antibody-humanized antibody designed in Example 22-1) (SEQ ID NO:118), and LV2, LV3, LV4, and LV6 designed by the method of Example 22-1) were synthesized by gene synthesis.

22-5) Construction of Vectors Expressing c10D5-2-3 Antibody and Humanized Antibody VH of 10D5-2-3 antibody, cDNA encoding any one of HV0, HV3, HV4a, HV4b, HV7a, HV7b, and HV9 obtained in Example 22-3), and VL of 10D5-2-3 antibody, cDNA encoding any one of LV0, LV2, LV3, LV4, and LV6 obtained in Example 22-4) were inserted into an appropriate position of the humanized antibody expression vector pKANTEX93 described in WO 97/10354, so as to construct various 10D5-2-3 antibody-humanized antibody expression vectors.

22-6) Expression of c10D5-2-3 Antibody and 10D5-2-3 Antibody-Humanized Antibody in Animal Cells CHO-S cell line (manufactured by Invitrogen) was used for gene transfection of the antibody expression vectors for animal cells, which were constructed in Example 22-5).

CHO-S was used as a host cell to perform transient transfection in accordance with the instructions of FreeStyle™ MAX CHO Expression System (manufactured by Invitrogen). 312.5 µL of FreeStyle™ MAX Transfection Reagent (manufactured by Invitrogen) was mixed with OptiPro™ SFM to a final volume of 5 mL. The expression vector plasmid solution and the FreeStyle™ MAX Transfection Reagent solution were mixed, and left at room temperature for 10 minutes. Then this mixture was added to 250 mL of CHO-S cultured at a density of $1.0 \times 10^6$ cells/mL in FreeStyle™ CHO Expression Medium (manufactured by Invitrogen), and cells were further cultured under the conditions of 37° C., 8% $CO_2$, and 135 rpm for 5 days to 7 days.

After culture, a cell suspension was recovered, and centrifuged under the conditions of 3000 rpm and 4° C. for 20 minutes. The culture supernatant was recovered, and then sterilized by filtration using a Millex GV filter with a pore size of 0.22 µm (manufactured by MILLIPORE).

22-7) Acquisition of Purified c10D5-2-3 Antibody and 10D5-2-3 Antibody-Humanized Antibody A column with a diameter of 0.8 cm was packed with 0.5 mL of MabSelect SuRe (manufactured by GE Healthcare), and 3.0 mL of purified water, 2.0 mL of 0.1 M citrate buffer (pH 3.5), and 1.5 mL of 150 mM NaCl and 0.2 M sodium borate buffer (pH 7.5) were serially loaded thereto for equilibration.

Subsequently, the culture supernatant recovered in Example 22-6) was loaded to the column, and the column was washed with 5.0 mL of 150 mM NaCl and 0.2 M sodium borate buffer (pH 7.5). After washing, 2.0 mL of 0.1 M citrate buffer (pH 3.5) was used to elute the antibodies adsorbed onto the column. Elution was performed to obtain 4 fractions of each 500 µL.

Subsequently, the obtained purified fractions were subjected to SDS-PAGE, and the fractions including the desired protein were mixed and subjected to dialysis using 150 mM NaCl and 10 mM sodium citrate solution (pH 6.0) at 4° C. overnight.

After dialysis, c10D5-2-3 antibody and humanized antibody solutions were recovered, and sterilized by filtration using a MillexgV (manufactured by MILLIPORE) with a pore size of 0.22 µm. Absorbance at 280 nm (OD280 nm) was determined using a spectrometer (SHIMADZU UV-1700), and the concentrations of the purified c10D5-2-3 antibody and humanized antibody were calculated.

As a result, it was found that one type of chimeric c10D5-2-3 antibody which was composed of VH of 10D5-2-3 antibody and VL of 10D5-2-3 antibody, and 22 types of the humanized antibodies, HV0LV0, HV0LV2, HV0LV3, HV0LV4, and HV0LV6 which were composed of HV0 as VH of antibody and LV0, LV2, LV3, LV4, or LV6 as VL of antibody, the humanized antibodies, HV9LV0, HV9LV2, HV9LV3, HV9LV4, and HV9LV6 which were composed of HV9 as VH of antibody and LV0, LV2, LV3, LV4, or LV6 as VL of antibody, the humanized antibodies, HV3LV0, HV3LV2, HV3LV3, and HV3LV6 which were composed of HV3 as VH of antibody and LV0, LV2, LV3, or LV6 as VL of antibody, the humanized antibody HV4aLV0 which was composed of HV4a as VH of antibody and LV0 as VL of antibody, the humanized antibodies, HV4bLV0, HV4bLV2, HV4bLV3, and HV4bLV6 which were composed of HV4b as VH of antibody and LV0, LV2, LV3, or LV6 as VL of antibody, the humanized antibodies, HV7a LV0 and HV7a LV2 which were composed of HV7a as VH of antibody and LV0 or LV2 as VL of antibody, and the humanized antibody, HV7bLV2 which was composed of HV7b as VH of antibody and LV2 as VL of antibody were prepared.

Example 23

Evaluation of Activity of Anti-BMP9 Humanized Antibody 23-1) Evaluation of Binding Activity of c10D5-2-3 Antibody and Humanized Antibody to Human BMP9 Protein by Biacore Analysis For the purpose of comparing binding activity to human BMP9 between c10D5-2-3 antibody and 22 types of 10D5-2-3 antibody-humanized antibodies obtained in Example 22-7, binding activity to human BMP9 recombinant protein (manufactured by R&D systems) was measured by surface plasmon resonance (SPR) using a BiacoreT100 instrument (manufactured by GE Healthcare bioscience).

Anti-human IgG antibody was immobilized onto a CM5 sensor chip (manufactured by GE Healthcare bioscience) using a Human Antibody Capture Kit (manufactured by GE Healthcare bioscience) in accordance with the accompanying protocol. 0.4 μg/mL of c10D5-2-3 antibody or each humanized antibody was applied to the flow cell onto which anti-human IgG antibody was immobilized, at a flow rate of 10 μL/min for 2 minutes.

Subsequently, human BMP9 recombinant protein (manufactured by R&D systems, Cat#3209-BP) was subjected to 2-fold serial dilution starting from 1 nm to give 5 concentrations, and applied at a flow rate of 10 μL/min, and association was monitored over 3 minutes and dissociation over 3 minutes at a flow of 10 μL/min. The sensorgram thus obtained was analyzed by BiaEvaluation Software (manufactured by GE Healthcare bioscience) to calculate the rate constant of each antibody.

The association rate constant (ka1), dissociation rate constant (kd1), and dissociation constant [kd1/ka1=$K_D$] of each antibody were given in Table 3. As a result, 17 types of 10D5-2-3 antibody-humanized antibodies were found to have specific reactivity of 10E-11 or less to human BMP9 protein.

TABLE 3

| Antibody | Kd (1/Ms) | Ka (1/s) | KD (M) |
| --- | --- | --- | --- |
| c10D5-2-3 antibody | 5.32 × 10E7 | 2.40 × 10E-4 | 4.52 × 10E-12 |
| HV0LV0 | | | N.D. |
| HV0LV2 | | | N.D. |
| HV0LV3 | | | N.D. |
| HV0LV4 | | | N.D. |
| HV0LV6 | | | N.D. |
| HV9LV0 | 13.3 × 10E7 | 8.59 × 10E-4 | 6.45 × 10E-12 |
| HV9LV2 | 8.91 × 10E7 | 3.47 × 10E-4 | 3.89 × 10E-12 |
| HV9LV3 | 7.91 × 10E7 | 2.79 × 10E-4 | 3.52 × 10E-12 |
| HV9LV4 | 11.6 × 10E7 | 7.39 × 10E-4 | 6.38 × 10E-12 |
| HV9LV6 | 6.34 × 10E7 | 3.25 × 10E-4 | 5.13 × 10E-12 |
| HV3LV0 | 15.1 × 10E7 | 17.2 × 10E-4 | 11.4 × 10E-12 |
| HV4aLV0 | 15.7 × 10E7 | 14.5 × 10E-4 | 9.24 × 10E-12 |
| HV4bLV0 | 14.4 × 10E7 | 16.4 × 10E-4 | 11.4 × 10E-12 |
| HV7aLV0 | 14.7 × 10E7 | 14.2 × 10E-4 | 9.69 × 10E-12 |
| HV3LV2 | 5.12 × 10E7 | 5.96 × 10E-4 | 11.6 × 10E-12 |
| HV3LV3 | 5.43 × 10E7 | 5.16 × 10E-4 | 9.49 × 10E-12 |
| HV3LV6 | 4.67 × 10E7 | 5.55 × 10E-4 | 11.9 × 10E-12 |
| HV4bLV2 | 5.39 × 10E7 | 5.88 × 10E-4 | 10.9 × 10E-12 |
| HV4bLV3 | 5.50 × 10E7 | 5.56 × 10E-4 | 10.1 × 10E-12 |
| HV4bLV6 | 4.46 × 10E7 | 5.31 × 10E-4 | 11.9 × 10E-12 |
| HV7aLV2 | 4.98 × 10E7 | 4.77 × 10E-4 | 9.57 × 10E-12 |
| HV7bLV2 | 6.25 × 10E7 | 3.07 × 10E-4 | 4.91 × 10E-12 |

N.D.: Not Detected

Example 24

Effect of 10D5-2-3 Antibody-Humanized Antibody on Erythropoiesis in Normal BALB/c Mouse Subsequently, the erythropoietic activities of 4 types of humanized antibodies (HV9LV2, HV9LV3, HV7aLV2, and HV7bLV2) were evaluated using BALB/c mouse, in order to examine whether the 10D5-2-3 antibody-humanized antibodies actually function to increase erythrocytes. 7-week-old male BALB/c mouse (Charles River Laboratories Japan Inc.) was purchased and subjected to the experiments. Sterile tap water was used as drinking water, and solid feed FR-2 (manufactured by Funabashi Farm) was provided as diet with free access.

After pre-breeding, mice were divided into 7 groups (n=6 per group) based on body weight, and 4 types of humanized antibodies (HV9LV2, HV9LV3, HV7aLV2, and HV7bLV2) as well as c10D5-2-3 antibody and 10D5-2-3 antibody were administered at a dose of 1 mg/kg by subcutaneous injection.

In detail, each antibody was prepared in a concentration of 0.1 mg/mL using physiological saline, and each was administered at a dose of 10 mL/kg. The vehicle group was administered with physiological saline at a dose of 10 mg/kg by subcutaneous injection. 1 week after antibody administration, blood was collected from the orbital vein under isoflurane anesthesia, and put in an EDTA-containing tube, and used as a blood sample.

The blood samples thus obtained were diluted 2-fold with physiological saline, and the numbers of various blood cells were determined using an automated blood cell counter ADVIA120 (manufactured by Bayer). With respect to the number of erythrocyte of each group (×$10^4$/μL), the saline group showed 1036.3±10.9, whereas the HV9LV2-treated group, the HV9LV3-treated group, the HV7aLV2-treated group, the HV7bLV2-treated group, the c10D5-2-3 antibody-treated group, and the 10D5-2-3 antibody-treated group showed 1168.0±13.4, 1157.3±8.7, 1145.3±12.8, 1144.3±14.4, 1127.7±10.9, and 1106.0±7.5 (mean±standard error), respectively, indicating that all of the humanized antibodies significantly increase the number of erythrocyte.

While the invention has been described in detail and with reference to specific embodiments thereof, it will be apparent to one skill in the art that various changes and modifications can be made therein without departing from the spirit and scope thereof.

This application is based on U.S. provisional application No. 61/666,981, filed on Jul. 2, 2012, the entire contents of which are incorporated hereinto by reference. All references cited herein are incorporated in their entirety.

SEQ ID NO:1: Base sequence of LinkA1
SEQ ID NO:2: Base sequence of LinkA2
SEQ ID NO:3: Base sequence of LinkB1
SEQ ID NO:4: Base sequence of LinkB2

SEQ ID NO:5: Base sequence of Bmp9KOClaI-3'Fw
SEQ ID NO:6: Base sequence of Bmp9KOAscI-3'Rv
SEQ ID NO:7: Base sequence of Bmp9KOPacI-5'Fw
SEQ ID NO:8: Base sequence of Bmp9KOFseI-5'Rv
SEQ ID NO:9: Base sequence of Bmp9KO5' probe FW2
SEQ ID NO:10: Base sequence of Bmp9KO5' probe RV2
SEQ ID NO:11: Base sequence of Bmp9KO3' probe FW2
SEQ ID NO:12: Base sequence of Bmp9KO3' probe RV2
SEQ ID NO:13: Base sequence of mBMP9_FW5915
SEQ ID NO:14: Base sequence of mBMP9_RV17165
SEQ ID NO:15: Base sequence of mBMP9_FW1
SEQ ID NO:16: Base sequence of mBMP9_RV1
SEQ ID NO:17: Base sequence of mouse IgG1-specific primer RV1
SEQ ID NO:18: Base sequence of mouse IgG1-specific primer RV2
SEQ ID NO:19: Base sequence of mouse IgG2a-specific primer RV1
SEQ ID NO:20: Base sequence of mouse IgG2a-specific primer RV2
SEQ ID NO:21: Base sequence of mouse IgG2b-specific primer RV1
SEQ ID NO:22: Base sequence of mouse IgG2b-specific primer RV2
SEQ ID NO:23: Base sequence of mouse IgG2c-specific primer RV
SEQ ID NO:24: Base sequence of mouse IgG3-specific primer RV1
SEQ ID NO:25: Base sequence of mouse IgG3-specific primer RV2
SEQ ID NO:26: Base sequence of mouse Ig(κ)-specific primer RV1
SEQ ID NO:27: Base sequence of mouse Ig(κ)-specific primer RV2
SEQ ID NO:28: Base sequence of mouse Ig(λ)-specific primer RV1
SEQ ID NO:29: Base sequence of mouse Ig(λ)-specific primer RV2
SEQ ID NO:30: Entire base sequence of VH of 6D10-1-1 antibody
SEQ ID NO:31: Entire base sequence of VH of 10D5-2-3 antibody
SEQ ID NO:32: Entire base sequence of VH of 3B7-3-3 antibody
SEQ ID NO:33: Entire amino acid sequence of VH of 6D10-1-1 antibody (including signal sequence)
SEQ ID NO:34: Entire amino acid sequence of VH of 10D5-2-3 antibody (including signal sequence)
SEQ ID NO:35: Entire amino acid sequence of VH of 3B7-3-3 antibody (including signal sequence)
SEQ ID NO:36: Entire base sequence of VL of 6D10-1-1 antibody
SEQ ID NO:37: Entire base sequence of VL of 10D5-2-3 antibody
SEQ ID NO:38: Entire base sequence of VL of 3B7-3-3 antibody
SEQ ID NO:39: Entire amino acid sequence of VL of 6D10-1-1 antibody (including signal sequence)
SEQ ID NO:40: Entire amino acid sequence of VL of 10D5-2-3 antibody (including signal sequence)
SEQ ID NO:41: Entire amino acid sequence of VL of 3B7-3-3 antibody (including signal sequence)
SEQ ID NO:42: Base sequence of VH of 6D10-1-1 antibody (excluding signal sequence)
SEQ ID NO:43: Base sequence of VH of 10D5-2-3 antibody (excluding signal sequence)
SEQ ID NO:44: Base sequence of VH of 3B7-3-3 antibody (excluding signal sequence)
SEQ ID NO:45: Base sequence of VL of 6D10-1-1 antibody (excluding signal sequence)
SEQ ID NO:46: Base sequence of VL of 10D5-2-3 antibody (excluding signal sequence)
SEQ ID NO:47: Base sequence of VL of 3B7-3-3 antibody (excluding signal sequence)
SEQ ID NO:48: Amino acid sequence of VH of 6D10-1-1 antibody (excluding signal sequence)
SEQ ID NO:49: Amino acid sequence of VH of 10D5-2-3 antibody (excluding signal sequence)
SEQ ID NO:50: Amino acid sequence of VH of 3B7-3-3 antibody (excluding signal sequence)
SEQ ID NO:51: Amino acid sequence of VL of 6D10-1-1 antibody (excluding signal sequence)
SEQ ID NO:52: Amino acid sequence of VL of 10D5-2-3 antibody (excluding signal sequence)
SEQ ID NO:53: Amino acid sequence of VL of 3B7-3-3 antibody (excluding signal sequence)
SEQ ID NO:54: Amino acid sequence of CDR1 of VH of 6D10-1-1 antibody
SEQ ID NO:55: Amino acid sequence of CDR2 of VH of 6D10-1-1 antibody
SEQ ID NO:56: Amino acid sequence of CDR3 of VH of 6D10-1-1 antibody
SEQ ID NO:57: Amino acid sequence of CDR1 of VL of 6D10-1-1 antibody
SEQ ID NO:58: Amino acid sequence of CDR2 of VL of 6D10-1-1 antibody
SEQ ID NO:59: Amino acid sequence of CDR3 of VL of 6D10-1-1 antibody
SEQ ID NO:60: Amino acid sequence of CDR1 of VH of 10D5-2-3 antibody
SEQ ID NO:61: Amino acid sequence of CDR2 of VH of 10D5-2-3 antibody
SEQ ID NO:62: Amino acid sequence of CDR3 of VH of 10D5-2-3 antibody
SEQ ID NO:63: Amino acid sequence of CDR1 of VL of 10D5-2-3 antibody
SEQ ID NO:64: Amino acid sequence of CDR2 of VL of 10D5-2-3 antibody
SEQ ID NO:65: Amino acid sequence of CDR3 of VL of 10D5-2-3 antibody
SEQ ID NO:66: Amino acid sequence of human BMP9 protein (including signal sequence)
SEQ ID NO:67: Amino acid sequence of human BMP9 mature region
SEQ ID NO:68: Base sequence encoding human BMP9 protein (including signal sequence)
SEQ ID NO:69: Base sequence encoding human BMP9 mature region
SEQ ID NO:70: Amino acid sequence of human BMPRII
SEQ ID NO:71: Amino acid sequence of human ALK1
SEQ ID NO:72: Base sequence of Fwd primer used in amplification of light chain of 6D10-1-1 antibody
SEQ ID NO:73: Base sequence of Rv primer used in amplification of light chain of 6D10-1-1 antibody
SEQ ID NO:74: Base sequence of Fwd primer used in amplification of heavy chain of 6D10-1-1 antibody
SEQ ID NO:75: Base sequence of Rv primer used in amplification of heavy chain of 6D10-1-1 antibody
SEQ ID NO:76: Base sequence of Fwd primer used in amplification of light chain of 10D5-2-3 antibody
SEQ ID NO:77: Base sequence of Rv primer used in amplification of light chain of 10D5-2-3 antibody SEQ ID NO:78: Base sequence of Fwd primer used in amplification of heavy chain of 10D5-2-3 antibody
SEQ ID NO:79: Base sequence of Rv primer used in amplification of heavy chain of 10D5-2-3 antibody
SEQ ID NO:80: Base sequence of mouse light chain (κ chain) constant region as a template
SEQ ID NO:81: Base sequence of mouse heavy chain (IgG1) constant region as a template
SEQ ID NO:82: Base sequence of Fwd primer used in amplification of mouse light chain (κ chain) constant region
SEQ ID NO:83: Base sequence of Rv primer used in amplification of mouse light chain (κ chain) constant region
SEQ ID NO:84: Base sequence of Fwd primer used in amplification of mouse heavy chain (IgG1) constant region
SEQ ID NO:85: Base sequence of Rv primer used in amplification of mouse heavy chain (IgG1) constant region
SEQ ID NO:86: Amino acid sequence of region C of human BMP9
SEQ ID NO:87: Amino acid sequence of region C of human BMP9/BMP10 chimeric protein 1
SEQ ID NO:88: Amino acid sequence of region C of human BMP9/BMP10 chimeric protein 2
SEQ ID NO:89: Amino acid sequence of region C of human BMP9/BMP10 chimeric protein 3
SEQ ID NO:90: Amino acid sequence of region C of human BMP9/BMP10 chimeric protein 4
SEQ ID NO:91: Amino acid sequence of region C of human BMP9/BMP10 chimeric protein 5
SEQ ID NO:92: Base sequence of primer 1 for chimeric protein preparation
SEQ ID NO:93: Base sequence of primer 2 for chimeric protein preparation
SEQ ID NO:94: Base sequence of primer 3 for chimeric protein preparation
SEQ ID NO:95: Base sequence of primer 4 for chimeric protein preparation
SEQ ID NO:96: Base sequence of primer 5 for chimeric protein preparation
SEQ ID NO:97: Base sequence of primer 6 for chimeric protein preparation
SEQ ID NO:98: Base sequence of primer 7 for chimeric protein preparation
SEQ ID NO:99: Base sequence of primer 8 for chimeric protein preparation
SEQ ID NO:100: Base sequence of primer 9 for chimeric protein preparation
SEQ ID NO:101: Base sequence of primer 10 for chimeric protein preparation
SEQ ID NO:102: Base sequence of Fwd-1 primer for human BMP10 cloning
SEQ ID NO:103: Base sequence of Rv-1 primer for human BMP10 cloning
SEQ ID NO:104: Base sequence of Fwd-2 primer for human BMP10 cloning
SEQ ID NO:105: Base sequence of Rv-2 primer for human BMP10 cloning
SEQ ID NO:106: Amino acid sequence of human BMP10 protein (including signal sequence)
SEQ ID NO:107: Amino acid sequence of human BMP10 mature region
SEQ ID NO:108: Base sequence encoding human BMP10 protein (including signal sequence)
SEQ ID NO:109: Base sequence encoding human BMP10 mature region
SEQ ID NO:110: Amino acid sequence of the protein expressed by pLN1V5_human BMP10 vector
SEQ ID NO:111: Base sequence encoding amino acids expressed by pLN1V5_human BMP10 vector
SEQ ID NO:112: Full-length cDNA of human ALK1
SEQ ID NO:113: Base sequence of hALK1 FPN
SEQ ID NO:114: hALK1 RP
SEQ ID NO:115: Base sequence of VH(HV0) of modified humanized antibody (excluding signal sequence)
SEQ ID NO:116: Amino acid sequence of VH(HV0) of modified humanized antibody (excluding signal sequence)
SEQ ID NO:117: Base sequence of VL(LV0) of modified humanized antibody (excluding signal sequence)
SEQ ID NO:118: Amino acid sequence of VL(LV0) of modified humanized antibody (excluding signal sequence)
SEQ ID NO:119: Base sequence of VH(HV3) of modified humanized antibody (excluding signal sequence)
SEQ ID NO:120: Amino acid sequence of VH(HV3) of modified humanized antibody (excluding signal sequence)
SEQ ID NO:121: Base sequence of VH(HV4a) of modified humanized antibody (excluding signal sequence)
SEQ ID NO:122: Amino acid sequence of VH(HV4a) of modified humanized antibody (excluding signal sequence)
SEQ ID NO:123: Base sequence of VH(HV4b) of modified humanized antibody (excluding signal sequence)
SEQ ID NO:124: Amino acid sequence of VH(HV4b) of modified humanized antibody (excluding signal sequence)
SEQ ID NO:125: Base sequence of VH(HV7a) of modified humanized antibody (excluding signal sequence)
SEQ ID NO:126: Amino acid sequence of VH(HV7a) of modified humanized antibody (excluding signal sequence)
SEQ ID NO:127: Base sequence of VH(HV7b) of modified humanized antibody (excluding signal sequence)
SEQ ID NO:128: Amino acid sequence of VH(HV7b) of modified humanized antibody (excluding signal sequence)
SEQ ID NO:129: Base sequence of VH(HV9) of modified humanized antibody (excluding signal sequence)
SEQ ID NO:130: Amino acid sequence of VH(HV9) of modified humanized antibody (excluding signal sequence)
SEQ ID NO:131: Base sequence of VL(LV2) of modified humanized antibody (excluding signal sequence)
SEQ ID NO:132: Amino acid sequence of VL(LV2) of modified humanized antibody (excluding signal sequence)
SEQ ID NO:133: Base sequence of VL(LV3) of modified humanized antibody (excluding signal sequence)
SEQ ID NO:134: Amino acid sequence of VL(LV3) of modified humanized antibody (excluding signal sequence)
SEQ ID NO:135: Base sequence of VL(LV4) of modified humanized antibody (excluding signal sequence)
SEQ ID NO:136: Amino acid sequence of VL(LV4) of modified humanized antibody (excluding signal sequence)
SEQ ID NO:137: Base sequence of VL(LV6) of modified humanized antibody (excluding signal sequence)
SEQ ID NO:138: Amino acid sequence of VL(LV6) of modified humanized antibody (excluding signal sequence)
SEQ ID NO:139: Amino acid sequence of human BMP10 region C

What is claimed is:

1. A monoclonal antibody which binds to human BMP9 or an antigen-binding fragment thereof selected from the following (a) to (c):

(a) a monoclonal antibody or an antigen-binding fragment thereof which comprises a heavy chain of an antibody which comprises complementarity determining regions (CDRs) 1 to 3 comprising the amino acid sequences represented by SEQ ID NOs:54 to 56, respectively, and comprises a light chain of an antibody which comprises CDRs 1 to 3 comprising the amino acid sequences represented by SEQ ID NOs:57 to 59, respectively, (b) a monoclonal antibody or an antigen-binding fragment thereof which comprises a heavy chain of an antibody which comprises CDRs 1 to 3 comprising the amino acid sequences represented by SEQ ID NOs:60 to 62, respectively, and comprises a light chain of an antibody which comprises CDRs 1 to 3 comprising the amino acid sequences represented by SEQ ID NOs:63 to 65, respectively, and (c) an antibody or an antigen-binding fragment thereof which comprises a heavy chain variable region of an antibody comprising the amino acid sequence represented by SEQ ID NO: 128, and comprises a light chain variable region of an antibody comprising the amino acid sequences represented by SEQ ID NO: 132.

2. A monoclonal antibody which binds to human BMP9 or an antigen-binding fragment thereof, wherein the monoclonal antibody or the antigen-binding fragment thereof binds to at least Lys at position 87, Asp at position 89, Met at position 90, and Pro at position 93 in the amino acid sequence of human BMP9 mature region of SEQ ID NO:67; and wherein the monoclonal antibody or the antigen-binding fragment thereof binds to human BMP9 with a dissociation constant equal to or less than $1\times10^{-10}$ mol/L.

3. The monoclonal antibody or the antigen-binding fragment thereof according to claim 2, wherein the monoclonal antibody or the antigen-binding fragment thereof is a recombinant antibody.

4. The monoclonal antibody or the antigen-binding fragment thereof according to claim 3, wherein the recombinant antibody is selected from a human chimeric antibody, a humanized antibody and a human antibody.

5. The antigen-binding fragment according to claim 1 or 2, wherein the antigen-binding fragment is selected from Fab, Fab', F(ab')2, a single chain antibody (scFv), a dimerized V region (diabody), a disulfide stabilized V region (dsFv) and a peptide comprising CDR.

6. A DNA encoding the monoclonal antibody or the antibody fragment thereof according to claim 1 or 2.

7. A recombinant vector comprising the DNA according to claim 6.

8. A transformant obtained by introducing the recombinant vector according to claim 7 into a host cell.

9. A method for preparing a monoclonal antibody or an antigen-binding fragment thereof, comprising culturing the transformant according to claim 8 in a medium to form and accumulate the monoclonal antibody or the antigen-binding fragment thereof in the culture broth, and collecting the antibody or the antigen-binding fragment thereof from the culture broth,
wherein said monoclonal antibody or an antigen-binding fragment thereof is selected from the following (a) to (e):
(a) an antibody which comprises a heavy chain of an antibody which comprises complementarity determining regions (CDR) 1 to 3 comprising the amino acid sequences represented by SEQ ID NOs:54 to 56, respectively, and comprises a light chain of an antibody which comprises CDRs 1 to 3 comprising the amino acid sequences represented by SEQ ID NOs:57 to 59, respectively,
(b) an antibody which comprises a heavy chain of an antibody which comprises CDRs 1 to 3 comprising the amino acid sequences represented by SEQ ID NOs:60 to 62, respectively, and comprises a light chain of an antibody which comprises CDRs 1 to 3 comprising the amino acid sequences represented by SEQ ID NOs:63 to 65, respectively,
(c) an antibody which comprises a heavy chain variable region of an antibody comprising the amino acid sequence represented by SEQ ID NO:48, and comprises a light chain variable region of an antibody comprising the amino acid sequences represented by SEQ ID NO:51,
(d) an antibody which comprises a heavy chain variable region of an antibody comprising the amino acid sequence represented by SEQ ID NO:49, and comprises a light chain variable region of an antibody comprising the amino acid sequences represented by SEQ ID NO:52, and
(e) an antibody which comprises a heavy chain variable region of an antibody comprising the amino acid sequence represented by SEQ ID NO:128, and comprises a light chain variable region of an antibody comprising the amino acid sequences represented by SEQ ID NO:132.

10. A method for preparing a monoclonal antibody or an antigen-binding fragment thereof, comprising culturing the transformant according to claim 8 in a medium to form and accumulate the monoclonal antibody or the antigen-binding fragment thereof in the culture broth, and collecting the antibody or the antigen-binding fragment thereof from the culture broth,
wherein said monoclonal antibody or antigen-binding fragment thereof is selected from following (a) to (c):
(a) a monoclonal antibody or an antigen-binding fragment thereof which comprises a heavy chain of an antibody which comprises CDRs 1 to 3 comprising the amino acid sequences represented by SEQ ID NOs:54 to 56, respectively, and comprises a light chain of an antibody which comprises CDRs 1 to 3 comprising the amino acid sequences represented by SEQ ID NOs:57 to 59, respectively,
(b) a monoclonal antibody or an antigen-binding fragment thereof which comprises a heavy chain of an antibody which comprises CDRs 1 to 3 comprising the amino acid sequences represented by SEQ ID NOs:60 to 62, respectively, and comprises a light chain of an antibody which comprises CDRs 1 to 3 comprising the amino acid sequences represented by SEQ ID NOs:63 to 65, respectively, and
(c) an antibody or an antigen-binding fragment thereof which comprises a heavy chain variable region of an antibody comprising the amino acid sequence represented by SEQ ID NO:128, and comprises a light chain variable region of an antibody comprising the amino acid sequences represented by SEQ ID NO:132.

11. A method for preparing a monoclonal antibody or an antigen-binding fragment thereof, comprising culturing the transformant according to claim 8 in a medium to form and accumulate the monoclonal antibody or the antigen-binding fragment thereof in the culture broth, and collecting the antibody or the antigen-binding fragment thereof from the culture broth,
wherein said monoclonal antibody or antigen-binding fragment thereof binds to at least Lys at position 87, Asp at position 89, Met at position 90, and Pro at position 93 in the amino acid sequence of human BMP9 mature region of SEQ ID NO:67 and wherein said monoclonal antibody or antigen-binding fragment thereof binds to human BMP9 with a dissociation constant equal to or less than $1\times10^{-10}$ mol/L.

12. A method for immunologically detecting or measuring human BMP9, comprising allowing the monoclonal antibody or the antigen-binding fragment thereof according to claim 1 or 2 to be in contact with a human BMP9-containing sample or a human BMP9-containing tissue; and detecting or measuring a resulting complex of the antibody or the fragment with the human BMP9.

13. A pharmaceutical composition, comprising the monoclonal antibody or the antigen-binding fragment thereof according to claim 1 or 2 and a pharmaceutically acceptable carrier.

14. A method for treating human BMP9-involved anemia, comprising administering the monoclonal antibody or the antigen-binding fragment thereof according to claim 1 or 2 into a subject in need thereof, wherein the human BMP9-involved anemia is an anemia with renal failure.

* * * * *

SEQUENCE LISTING

<160> NUMBER OF SEQ ID NOS: 139

<210> SEQ ID NO 1
<211> LENGTH: 28
<212> TYPE: DNA

```
<213> ORGANISM: Artificial
<220> FEATURE:
<223> OTHER INFORMATION: LinkA1

<400> SEQUENCE: 1
tcgagtcgcg acaccggcgg gcgcgccc                                    28

<210> SEQ ID NO 2
<211> LENGTH: 28
<212> TYPE: DNA
<213> ORGANISM: Artificial
<220> FEATURE:
<223> OTHER INFORMATION: LinkA2

<400> SEQUENCE: 2
tcgagggcgc gcccgccggt gtcgcgac                                    28

<210> SEQ ID NO 3
<211> LENGTH: 29
<212> TYPE: DNA
<213> ORGANISM: Artificial
<220> FEATURE:
<223> OTHER INFORMATION: LinkB1

<400> SEQUENCE: 3
ggccgcttaa ttaaggccgg ccgtcgacg                                   29

<210> SEQ ID NO 4
<211> LENGTH: 29
<212> TYPE: DNA
<213> ORGANISM: Artificial
<220> FEATURE:
<223> OTHER INFORMATION: LinkB2

<400> SEQUENCE: 4
aattcgtcga cggccggcct taattaagc                                   29

<210> SEQ ID NO 5
<211> LENGTH: 38
<212> TYPE: DNA
<213> ORGANISM: Artificial
<220> FEATURE:
<223> OTHER INFORMATION: Bmp9KOClaI-3'Fw

<400> SEQUENCE: 5
ccatcgattg gggatacagg acatggaaga ggttctgg                         38

<210> SEQ ID NO 6
<211> LENGTH: 40
<212> TYPE: DNA
<213> ORGANISM: Artificial
<220> FEATURE:
<223> OTHER INFORMATION: Bmp9KOAscI-3'Rv

<400> SEQUENCE: 6
ttggcgcgcc gtctgagcat gacagtggtg gacagacact                       40

<210> SEQ ID NO 7
<211> LENGTH: 40
<212> TYPE: DNA
<213> ORGANISM: Artificial
<220> FEATURE:
<223> OTHER INFORMATION: Bmp9KOPacI-5'Fw

<400> SEQUENCE: 7
ccttaattaa ctcccaattc ctgggccttc tgctcaggag                       40
```

<210> SEQ ID NO 8
<211> LENGTH: 40
<212> TYPE: DNA
<213> ORGANISM: Artificial
<220> FEATURE:
<223> OTHER INFORMATION: Bmp9KOFseI-5'Rv

<400> SEQUENCE: 8
taggccggcc cttgggccct gaaggggggcc tgaggggctg                    40

<210> SEQ ID NO 9
<211> LENGTH: 25
<212> TYPE: DNA
<213> ORGANISM: Artificial
<220> FEATURE:
<223> OTHER INFORMATION: Bmp9 KO5' probe FW2

<400> SEQUENCE: 9
cacagatact gtcctagagc ttcct                                    25

<210> SEQ ID NO 10
<211> LENGTH: 25
<212> TYPE: DNA
<213> ORGANISM: Artificial
<220> FEATURE:
<223> OTHER INFORMATION: Bmp9 KO5' probe RV2

<400> SEQUENCE: 10
catttcctgg aacactacct tagag                                    25

<210> SEQ ID NO 11
<211> LENGTH: 25
<212> TYPE: DNA
<213> ORGANISM: Artificial
<220> FEATURE:
<223> OTHER INFORMATION: Bmp9 KO3' probe FW2

<400> SEQUENCE: 11
tcatcttgaa agttgtgagg tactg                                    25

<210> SEQ ID NO 12
<211> LENGTH: 25
<212> TYPE: DNA
<213> ORGANISM: Artificial
<220> FEATURE:
<223> OTHER INFORMATION: Bmp9 KO3' probe RV2

<400> SEQUENCE: 12
gatatgcttt ctacacccac agttt                                    25

<210> SEQ ID NO 13
<211> LENGTH: 25
<212> TYPE: DNA
<213> ORGANISM: Artificial
<220> FEATURE:
<223> OTHER INFORMATION: mBMP9_FW5915

<400> SEQUENCE: 13
gtagaggagg ttagggttta tgagg                                    25

<210> SEQ ID NO 14
<211> LENGTH: 25
<212> TYPE: DNA
<213> ORGANISM: Artificial
<220> FEATURE:

<223> OTHER INFORMATION: mBMP9_RV17165

<400> SEQUENCE: 14
atcgccttct atcgccttct tgacg                                   25

<210> SEQ ID NO 15
<211> LENGTH: 20
<212> TYPE: DNA
<213> ORGANISM: Artificial
<220> FEATURE:
<223> OTHER INFORMATION: mBMP9_FW1

<400> SEQUENCE: 15
aacggacaaa tcgtctacgc                                         20

<210> SEQ ID NO 16
<211> LENGTH: 20
<212> TYPE: DNA
<213> ORGANISM: Artificial
<220> FEATURE:
<223> OTHER INFORMATION: mBMP9_RV1

<400> SEQUENCE: 16
tccctgtttc attgggagtc                                         20

<210> SEQ ID NO 17
<211> LENGTH: 30
<212> TYPE: DNA
<213> ORGANISM: Artificial
<220> FEATURE:
<223> OTHER INFORMATION: Mouse IgG1 primer RV1

<400> SEQUENCE: 17
ccagggtcac catggagtta gtttgggcag                              30

<210> SEQ ID NO 18
<211> LENGTH: 30
<212> TYPE: DNA
<213> ORGANISM: Artificial
<220> FEATURE:
<223> OTHER INFORMATION: Mouse IgG1 primer RV2

<400> SEQUENCE: 18
tcaccatgga gttagtttgg gcagcagatc                              30

<210> SEQ ID NO 19
<211> LENGTH: 23
<212> TYPE: DNA
<213> ORGANISM: Artificial
<220> FEATURE:
<223> OTHER INFORMATION: Mouse IgG2a primer RV1

<400> SEQUENCE: 19
cagtggatag accgatgggg ctg                                     23

<210> SEQ ID NO 20
<211> LENGTH: 24
<212> TYPE: DNA
<213> ORGANISM: Artificial
<220> FEATURE:
<223> OTHER INFORMATION: Mouse IgG2a primer RV2

<400> SEQUENCE: 20
ttgaccaggc atcctagagt cacc                                    24

<210> SEQ ID NO 21
<211> LENGTH: 30
<212> TYPE: DNA
<213> ORGANISM: Artificial
<220> FEATURE:
<223> OTHER INFORMATION: Mouse IgG2b primer RV1

<400> SEQUENCE: 21
ttgaccaggc atcccagagt cacggaggaa                              30

<210> SEQ ID NO 22
<211> LENGTH: 30
<212> TYPE: DNA
<213> ORGANISM: Artificial
<220> FEATURE:
<223> OTHER INFORMATION: Mouse IgG2b primer RV2

<400> SEQUENCE: 22
tcacggagga accagttgta tctccacacc                              30

<210> SEQ ID NO 23
<211> LENGTH: 25
<212> TYPE: DNA
<213> ORGANISM: Artificial
<220> FEATURE:
<223> OTHER INFORMATION: Mouse IgG2c primer RV

<400> SEQUENCE: 23
cagttgtacc tccacacaca ggggc                                   25

<210> SEQ ID NO 24
<211> LENGTH: 22
<212> TYPE: DNA
<213> ORGANISM: Artificial
<220> FEATURE:
<223> OTHER INFORMATION: Mouse IgG3 primer RV1

<400> SEQUENCE: 24
agatgagact gtgcgcacac cg                                      22

<210> SEQ ID NO 25
<211> LENGTH: 25
<212> TYPE: DNA
<213> ORGANISM: Artificial
<220> FEATURE:
<223> OTHER INFORMATION: Mouse IgG3 primer RV2

<400> SEQUENCE: 25
ctggacaggg ctccatagtt ccatt                                   25

<210> SEQ ID NO 26
<211> LENGTH: 32
<212> TYPE: DNA
<213> ORGANISM: Artificial
<220> FEATURE:
<223> OTHER INFORMATION: Mouse Ig(kappa) primer RV1

<400> SEQUENCE: 26
ctaacactca ttcctgttga agctcttgac aa                           32

<210> SEQ ID NO 27
<211> LENGTH: 30
<212> TYPE: DNA
<213> ORGANISM: Artificial
<220> FEATURE:
<223> OTHER INFORMATION: Mouse Ig(kappa) primer RV2

<400> SEQUENCE: 27
gaagcacacg actgaggcac ctccagatgt                                    30

<210> SEQ ID NO 28
<211> LENGTH: 31
<212> TYPE: DNA
<213> ORGANISM: Artificial
<220> FEATURE:
<223> OTHER INFORMATION: Mouse Ig(lambda) primer RV1

<400> SEQUENCE: 28
ttagagacat tctgcaggag acagactctt c                                  31

<210> SEQ ID NO 29
<211> LENGTH: 30
<212> TYPE: DNA
<213> ORGANISM: Artificial
<220> FEATURE:
<223> OTHER INFORMATION: Mouse Ig(lambda) primer RV2

<400> SEQUENCE: 29
ctgggtgata ggtgtaccat ttgccttcca                                    30

<210> SEQ ID NO 30
<211> LENGTH: 417
<212> TYPE: DNA
<213> ORGANISM: Artificial
<220> FEATURE:
<223> OTHER INFORMATION: 6D10-1-1 VH

<400> SEQUENCE: 30
atggaatgga gcagagtctt tatctttctc ctatcagtaa ctgcaggtgt tcactcccag    60
gtccagctgc agcagtctgg agctgagctg gtaaggcctg ggacttcagt gaaggtgtcc   120
tgcaaggctt ctggatacgc cttcactaat tacttgatgg agtggattaa gcagaggcct   180
ggacagggcc ttgagtggat tgagtgatt catcctggaa ttggtgttac taactacaat   240
gagaagttca aggcaaggc aacactgact gcagacatat cctccagtac tgcctacatg   300
cagctcagca gcctgacatc tgaggactct gcggtctatt tctgtgcaag aagggctaac   360
tgggacctgt actactttga ctactggggc caaggcacca ctctcacagt ctcctca     417

<210> SEQ ID NO 31
<211> LENGTH: 414
<212> TYPE: DNA
<213> ORGANISM: Artificial
<220> FEATURE:
<223> OTHER INFORMATION: 10D5-2-3 VH

<400> SEQUENCE: 31
atggacttga gactgagctg tgctttatt attgttcttt taaaggggt ccagagtgaa     60
gtgaagcttg aggagtctag aggaggcttg gtgcaacctg gaggatccat gaaactctcc   120
tgtgttgcct ctggattcac tttcagtaac tactggatga actgggtccg ccagtctcca   180
gagaaggggc ttgagtgggt tgctcacatt agattaaaat ctgataatta tgcaacacat   240
tatgcggagt ctgtgagagg gaggttcact atctcaagag atgattccaa agtagtgtc   300
ttcctgcaaa tgaacaactt aagggctgaa gacactggaa tttattactg cacaggagga   360
agtaactacg tgtttgcttt ctggggccaa gggactctgg tcactgtctc tgca         414

<210> SEQ ID NO 32
<211> LENGTH: 408

<212> TYPE: DNA
<213> ORGANISM: Artificial
<220> FEATURE:
<223> OTHER INFORMATION: 3B7-3-3 VH

<400> SEQUENCE: 32

```
atgggatgga actggatctt tattttaatc ctgtcagtaa ctacaggtgt ccactctgag    60
gtccagctgc agcagtctag acctgaattg gtgaagcctg gggcttcagt gaagatctcc   120
tgcaaggcct ctgattactc attcactgac tactacatga actgggtgaa gcaaagccct   180
gacaagagcc ttgagtggat tggagagatt agtcctagct ctggtggtac tacctacaac   240
cagaagttca aggccaaggc cacattgact gtagacaaat cctccagcac agcctacatg   300
cagctcaaga gcctgacatc tgaggactct gcagtctatt actgtgcaac taggggggcc   360
ttctactttg actactgggg ccaaggcacc gctctcacag tctcctca              408
```

<210> SEQ ID NO 33
<211> LENGTH: 139
<212> TYPE: PRT
<213> ORGANISM: Artificial
<220> FEATURE:
<223> OTHER INFORMATION: 6D10-1-1 VH amino acids-signal plus

<400> SEQUENCE: 33

```
Met Glu Trp Ser Arg Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Asn Tyr Leu Met Glu Trp Ile Lys Gln Arg Pro Gly Gln Gly Leu
    50                  55                  60

Glu Trp Ile Gly Val Ile His Pro Gly Ile Gly Val Thr Asn Tyr Asn
65                  70                  75                  80

Glu Lys Phe Lys Gly Lys Ala Thr Leu Thr Ala Asp Ile Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Arg Ala Asn Trp Asp Leu Tyr Tyr Phe Asp Tyr
        115                 120                 125

Trp Gly Gln Gly Thr Thr Leu Thr Val Ser Ser
    130                 135
```

<210> SEQ ID NO 34
<211> LENGTH: 138
<212> TYPE: PRT
<213> ORGANISM: Artificial
<220> FEATURE:
<223> OTHER INFORMATION: 10D5-2-3 VH amino acids-signal plus

<400> SEQUENCE: 34

```
Met Asp Leu Arg Leu Ser Cys Ala Phe Ile Ile Val Leu Leu Lys Gly
1               5                   10                  15

Val Gln Ser Glu Val Lys Leu Glu Glu Ser Arg Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60
```

```
Glu Trp Val Ala His Ile Arg Leu Lys Ser Asp Asn Tyr Ala Thr His
 65                  70                  75                  80

Tyr Ala Glu Ser Val Arg Gly Arg Phe Thr Ile Ser Arg Asp Asp Ser
                 85                  90                  95

Lys Ser Ser Val Phe Leu Gln Met Asn Asn Leu Arg Ala Glu Asp Thr
            100                 105                 110

Gly Ile Tyr Tyr Cys Thr Gly Gly Ser Asn Tyr Val Phe Ala Phe Trp
        115                 120                 125

Gly Gln Gly Thr Leu Val Thr Val Ser Ala
    130                 135
```

<210> SEQ ID NO 35
<211> LENGTH: 136
<212> TYPE: PRT
<213> ORGANISM: Artificial
<220> FEATURE:
<223> OTHER INFORMATION: 3B7-3-3 VH amino acids-signal plus

<400> SEQUENCE: 35

```
Met Gly Trp Asn Trp Ile Phe Ile Leu Ile Leu Ser Val Thr Thr Gly
1               5                   10                  15

Val His Ser Glu Val Gln Leu Gln Gln Ser Arg Pro Glu Leu Val Lys
            20                  25                  30

Pro Gly Ala Ser Val Lys Ile Ser Cys Lys Ala Ser Asp Tyr Ser Phe
        35                  40                  45

Thr Asp Tyr Tyr Met Asn Trp Val Lys Gln Ser Pro Asp Lys Ser Leu
    50                  55                  60

Glu Trp Ile Gly Glu Ile Ser Pro Ser Ser Gly Gly Thr Thr Tyr Asn
 65                  70                  75                  80

Gln Lys Phe Lys Ala Lys Ala Thr Leu Thr Val Asp Lys Ser Ser Ser
                 85                  90                  95

Thr Ala Tyr Met Gln Leu Lys Ser Leu Thr Ser Glu Asp Ser Ala Val
            100                 105                 110

Tyr Tyr Cys Ala Thr Arg Gly Ala Phe Tyr Phe Asp Tyr Trp Gly Gln
        115                 120                 125

Gly Thr Ala Leu Thr Val Ser Ser
    130                 135
```

<210> SEQ ID NO 36
<211> LENGTH: 384
<212> TYPE: DNA
<213> ORGANISM: Artificial
<220> FEATURE:
<223> OTHER INFORMATION: 6D10-1-1 VL

<400> SEQUENCE: 36

```
atgatgtcct ctgctcagtt ccttggtctc ctgttgctct gttttcaagg taccagatgt    60
gatatccaga tgacacagat tacatcctcc ctgtctgcct ctctgggaga cagagtcacc   120
atcagttgca gtgcaagtca ggacattagc aattatttaa actggtatca gcagaaacca   180
gatggaactg ttaaactcct gatctattac acatcaagtt acactcagaa gtcccatcg   240 aggttcagtg gcagtgggtc tgggacagat tattctctca ccatcagcaa cctggaacct   300
gaagatattg ccacttacta ttgtcagcag tatattaacc ttccgctcac gttcggtgct   360
gggaccaagc tggagctgaa acgg                                          384
```

<210> SEQ ID NO 37

<211> LENGTH: 396
<212> TYPE: DNA
<213> ORGANISM: Artificial
<220> FEATURE:
<223> OTHER INFORMATION: 10D5-2-3 VL

<400> SEQUENCE: 37

```
atggagaaag acacactcct gctatgggtc ctgcttctct gggttccagg ttccacaggt    60
gacattgtgc tgacccaatc tccagcttct ttggctgtgt ctctaggcca gagggccacc   120
atctcctgca gagccagcga aagtgttgat aattatggca ttagttttat gaactggttc   180
caacagaaac caggacagcc acccaaactc ctcatctatg ctgcatccaa ccaaggatcc   240
ggggtccctg ccaggtttag tggcagtggg tctgggacag acttcagcct caacatccat   300
cctatggagg aggatgatac tgcaatgtat ttctgtcaac aaagtaagga ggttccgtgg   360
acgttcggtg gaggcaccaa gctggaaatc aagcgg                             396
```

<210> SEQ ID NO 38
<211> LENGTH: 387
<212> TYPE: DNA
<213> ORGANISM: Artificial
<220> FEATURE:
<223> OTHER INFORMATION: 3B7-3-3 VL

<400> SEQUENCE: 38

```
atggattttc aagtgcagat tttcagcttc ctgctaatga gtgcctcagt cataatgtcc    60
aggggacaaa ttgttctcac ccagtctcca gcactcatgt ctgcatttcc aggggagaag   120
gtcaccatga cctgcagtgc cagctcaagt gtgagttaca tgtactggta ccagcagaag   180
ccaagatcct cccccaaacc ctggatttat ctcacatcca acctggcttc tggagtccct   240
actcgcttca gtggcagtgg gtctgggacc tcttactctc tcacaatcag cagcatggag   300
gctgaagatg ctgccactta tttctgccag cagtggagta gtaatccacg gacgttcggt   360
ggaggcacca agctggaaat caaacgg                                       387
```

<210> SEQ ID NO 39
<211> LENGTH: 128
<212> TYPE: PRT
<213> ORGANISM: Artificial
<220> FEATURE:
<223> OTHER INFORMATION: 6D10-1-1 VL amino acids-signal plus

<400> SEQUENCE: 39

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
                20                  25                  30

Ala Ser Leu Gly Asp Arg Val Thr Ile Ser Cys Ser Ala Ser Gln Asp
            35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Ser Leu His Ser Glu Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Ala Thr Tyr Tyr Cys Gln Gln Tyr Ile
                100                 105                 110

Asn Leu Pro Leu Thr Phe Gly Ala Gly Thr Lys Leu Glu Leu Lys Arg
            115                 120                 125
```

<210> SEQ ID NO 40
<211> LENGTH: 132
<212> TYPE: PRT
<213> ORGANISM: Artificial
<220> FEATURE:
<223> OTHER INFORMATION: 10D5-2-3 VL amino acids-signal plus

<400> SEQUENCE: 40

Met Glu Lys Asp Thr Leu Leu Trp Val Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
            35                  40                  45

Val Asp Asn Tyr Gly Ile Ser Phe Met Asn Trp Phe Gln Gln Lys Pro
        50                  55                  60

Gly Gln Pro Pro Lys Leu Leu Ile Tyr Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Val Pro Trp Thr Phe Gly Gly Gly Thr Lys Leu
        115                 120                 125

Glu Ile Lys Arg
    130

<210> SEQ ID NO 41
<211> LENGTH: 129
<212> TYPE: PRT
<213> ORGANISM: Artificial
<220> FEATURE:
<223> OTHER INFORMATION: 3B7-3-3 VL amino acids-signal plus

<400> SEQUENCE: 41

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
                20                  25                  30

Met Ser Ala Phe Pro Gly Glu Lys Val Thr Met Thr Cys Ser Ala Ser
            35                  40                  45

Ser Ser Val Ser Tyr Met Tyr Trp Tyr Gln Gln Lys Pro Arg Ser Ser
        50                  55                  60

Pro Lys Pro Trp Ile Tyr Leu Thr Ser Asn Leu Ala Ser Gly Val Pro
65                  70                  75                  80

Thr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Phe Cys Gln Gln Trp
            100                 105                 110

Ser Ser Asn Pro Arg Thr Phe Gly Gly Gly Thr Lys Leu Glu Ile Lys
        115                 120                 125

Arg

<210> SEQ ID NO 42
<211> LENGTH: 360
<212> TYPE: DNA
<213> ORGANISM: Artificial

-continued

```
<220> FEATURE:
<223> OTHER INFORMATION: 6D10-1-1 VH signal minus

<400> SEQUENCE: 42
caggtccagc tgcagcagtc tggagctgag ctggtaaggc ctgggacttc agtgaaggtg      60
tcctgcaagg cttctggata cgccttcact aattacttga tggagtggat taagcagagg     120
cctggacagg gccttgagtg gattggagtg attcatcctg aattggtgt tactaactac      180 aatgagaagt tcaagggcaa ggcaacactg actgcagaca tatcctccag tactgcctac     240
atgcagctca gcagcctgac atctgaggac tctgcggtct atttctgtgc aagaagggct     300
aactgggacc tgtactactt tgactactgg ggccaaggca ccactctcac agtctcctca     360

<210> SEQ ID NO 43
<211> LENGTH: 357
<212> TYPE: DNA
<213> ORGANISM: Artificial
<220> FEATURE:
<223> OTHER INFORMATION: 10D5-2-3 VH signal minus

<400> SEQUENCE: 43
gaagtgaagc ttgaggagtc tagaggaggc ttggtgcaac ctggaggatc catgaaactc      60
tcctgtgttg cctctggatt cactttcagt aactactgga tgaactgggt ccgccagtct     120
ccagagaagg ggcttgagtg ggttgctcac attagattaa atctgataa ttatgcaaca      180 cattatgcgg agtctgtgag agggaggttc actatctcaa gagatgattc aaaagtagt     240 gtcttcctgc aaatgaacaa cttaaggcct gaagacactg gaatttatta ctgcacagga     300
ggaagtaact acgtgtttgc tttctggggc caagggactc tggtcactgt ctctgca        357

<210> SEQ ID NO 44
<211> LENGTH: 351
<212> TYPE: DNA
<213> ORGANISM: Artificial
<220> FEATURE:
<223> OTHER INFORMATION: 3B7-3-3 VH signal minus

<400> SEQUENCE: 44
gaggtccagc tgcagcagtc tagacctgaa ttggtgaagc tggggcttc agtgaagatc       60 tcctgcaagg cctctgatta ctcattcact gactactaca tgaactgggt gaagcaaagc     120
cctgacaaga gccttgagtg gattggagag attagtccta gctctggtgg tactacctac     180
aaccagaagt tcaaggccaa ggccacattg actgtagaca atcctccag cacagcctac      240 atgcagctca agagcctgac atctgaggac tctgcagtct attactgtgc aactaggggg    300
gccttctact ttgactactg gggccaaggc accgctctca gtctcctc a                351

<210> SEQ ID NO 45
<211> LENGTH: 324
<212> TYPE: DNA
<213> ORGANISM: Artificial
<220> FEATURE:
<223> OTHER INFORMATION: 6D10-1-1 VL signal minus

<400> SEQUENCE: 45
gatatccaga tgacacagat tacatcctcc ctgtctgcct ctctgggaga cagagtcacc      60
atcagttgca gtgcaagtca ggacattagc aattatttaa actggtatca gcagaaacca    120
gatggaactg ttaaactcct gatctattac acatcaagtt tacactcaga agtcccatcg     180
aggttcagtg gcagtgggtc tgggacagat tattctctca ccatcagcaa cctggaacct     240
```

```
gaagatattg ccacttacta ttgtcagcag tatattaacc ttccgctcac gttcggtgct    300
gggaccaagc tggagctgaa acgg                                           324
```

<210> SEQ ID NO 46
<211> LENGTH: 336
<212> TYPE: DNA
<213> ORGANISM: Artificial
<220> FEATURE:
<223> OTHER INFORMATION: 10D5-2-3 VL signal minus

<400> SEQUENCE: 46

```
gacattgtgc tgacccaatc tccagcttct ttggctgtgt ctctagggca gagggccacc     60
atctcctgca gagccagcga aagtgttgat aattatggca ttagtttat gaactggttc    120 caacagaaac caggacagcc acccaaactc ctcatctatg ctgcatccaa ccaaggatcc    180
ggggtccctg ccaggtttag tggcagtggg tctgggacag acttcagcct caacatccat    240
cctatggagg aggatgatac tgcaatgtat ttctgtcaac aaagtaagga ggttccgtgg    300
acgttcggtg gaggcaccaa gctggaaatc aagcgg                              336
```

<210> SEQ ID NO 47
<211> LENGTH: 321
<212> TYPE: DNA
<213> ORGANISM: Artificial
<220> FEATURE:
<223> OTHER INFORMATION: 3B7-3-3 VL signal minus

<400> SEQUENCE: 47

```
caaattgttc tcacccagtc tccagcactc atgtctgcat tccagggga aaggtcacc      60 atgacctgca gtgccagctc aagtgtgagt tacatgtact ggtaccagca gaagccaaga   120
tcctccccca aaccctggat ttatctcaca tccaacctgg cttctggagt ccctactcgc   180
ttcagtggca gtgggtctgg gacctcttac tctctcacaa tcagcagcat ggaggctgaa   240
gatgctgcca cttatttctg ccagcagtgg agtagtaatc cacggacgtt cggtggaggc   300
accaagctgg aaatcaaacg g                                              321
```

<210> SEQ ID NO 48
<211> LENGTH: 120
<212> TYPE: PRT
<213> ORGANISM: Artificial
<220> FEATURE:
<223> OTHER INFORMATION: 6D10-1-1 VH amino acids-signal minus

<400> SEQUENCE: 48

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Met Glu Trp Ile Lys Gln Arg Pro Gly Gln Gly Leu Glu Trp Ile
        35                  40                  45

Gly Val Ile His Pro Gly Ile Gly Val Thr Asn Tyr Asn Glu Lys Phe
    50                  55                  60

Lys Gly Lys Ala Thr Leu Thr Ala Asp Ile Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Ala Asn Trp Asp Leu Tyr Tyr Phe Asp Tyr Trp Gly Gln
            100                 105                 110
```

```
Gly Thr Thr Leu Thr Val Ser Ser
        115             120

<210> SEQ ID NO 49
<211> LENGTH: 119
<212> TYPE: PRT
<213> ORGANISM: Artificial
<220> FEATURE:
<223> OTHER INFORMATION: 10D5-2-3 VH amino acids-signal minus

<400> SEQUENCE: 49

Glu Val Lys Leu Glu Glu Ser Arg Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Ser Ser
65                  70                  75                  80

Val Phe Leu Gln Met Asn Asn Leu Arg Ala Glu Asp Thr Gly Ile Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ala
        115

<210> SEQ ID NO 50
<211> LENGTH: 117
<212> TYPE: PRT
<213> ORGANISM: Artificial
<220> FEATURE:
<223> OTHER INFORMATION: 3B7-3-3 VH amino acids-signal minus

<400> SEQUENCE: 50

Glu Val Gln Leu Gln Gln Ser Arg Pro Glu Leu Val Lys Pro Gly Ala
1               5                   10                  15

Ser Val Lys Ile Ser Cys Lys Ala Ser Asp Tyr Ser Phe Thr Asp Tyr
            20                  25                  30

Tyr Met Asn Trp Val Lys Gln Ser Pro Asp Lys Ser Leu Glu Trp Ile
        35                  40                  45

Gly Glu Ile Ser Pro Ser Ser Gly Thr Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Thr Arg Gly Ala Phe Tyr Phe Asp Tyr Trp Gly Gln Gly Thr Ala
            100                 105                 110

Leu Thr Val Ser Ser
        115

<210> SEQ ID NO 51
<211> LENGTH: 108
<212> TYPE: PRT
<213> ORGANISM: Artificial
<220> FEATURE:
<223> OTHER INFORMATION: 6D10-1-1 VL amino acids-signal minus
```

<400> SEQUENCE: 51

Asp Ile Gln Met Thr Gln Ile Thr Ser Ser Leu Ser Ala Ser Leu Gly
1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Glu Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ile Asn Leu Pro Leu
                85                  90                  95

Thr Phe Gly Ala Gly Thr Lys Leu Glu Leu Lys Arg
            100                 105

<210> SEQ ID NO 52
<211> LENGTH: 112
<212> TYPE: PRT
<213> ORGANISM: Artificial
<220> FEATURE:
<223> OTHER INFORMATION: 10D5-2-3 VL amino acids-signal minus

<400> SEQUENCE: 52

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

<210> SEQ ID NO 53
<211> LENGTH: 107
<212> TYPE: PRT
<213> ORGANISM: Artificial
<220> FEATURE:
<223> OTHER INFORMATION: 3B7-3-3 VL amino acids-signal minus

<400> SEQUENCE: 53

Gln Ile Val Leu Thr Gln Ser Pro Ala Leu Met Ser Ala Phe Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Thr Arg Phe Ser Gly Ser
50                  55                  60

Gly Ser Gly Thr Ser Tyr Ser Leu Thr Ile Ser Ser Met Glu Ala Glu
65                  70                  75                  80

-continued

```
Asp Ala Ala Thr Tyr Phe Cys Gln Gln Trp Ser Ser Asn Pro Arg Thr
                85                  90                  95
Phe Gly Gly Gly Thr Lys Leu Glu Ile Lys Arg
            100                 105

<210> SEQ ID NO 54
<211> LENGTH: 5
<212> TYPE: PRT
<213> ORGANISM: Artificial
<220> FEATURE:
<223> OTHER INFORMATION: 6D10-1-1 VH CDR1

<400> SEQUENCE: 54

Asn Tyr Leu Met Glu
1               5

<210> SEQ ID NO 55
<211> LENGTH: 17
<212> TYPE: PRT
<213> ORGANISM: Artificial
<220> FEATURE:
<223> OTHER INFORMATION: 6D10-1-1 VH CDR2

<400> SEQUENCE: 55

Val Ile His Pro Gly Ile Gly Val Thr Asn Tyr Asn Glu Lys Phe Lys
1               5                   10                  15
Gly

<210> SEQ ID NO 56
<211> LENGTH: 11
<212> TYPE: PRT
<213> ORGANISM: Artificial
<220> FEATURE:
<223> OTHER INFORMATION: 6D10-1-1 VH CDR3

<400> SEQUENCE: 56

Arg Ala Asn Trp Asp Leu Tyr Tyr Phe Asp Tyr
1               5                   10

<210> SEQ ID NO 57
<211> LENGTH: 11
<212> TYPE: PRT
<213> ORGANISM: Artificial
<220> FEATURE:
<223> OTHER INFORMATION: 6D10-1-1 VL CDR1

<400> SEQUENCE: 57

Ser Ala Ser Gln Asp Ile Ser Asn Tyr Leu Asn
1               5                   10

<210> SEQ ID NO 58
<211> LENGTH: 7
<212> TYPE: PRT
<213> ORGANISM: Artificial
<220> FEATURE:
<223> OTHER INFORMATION: 6D10-1-1 VL CDR2

<400> SEQUENCE: 58

Tyr Thr Ser Ser Leu His Ser
1               5

<210> SEQ ID NO 59
<211> LENGTH: 9
<212> TYPE: PRT
<213> ORGANISM: Artificial
<220> FEATURE:
```

<223> OTHER INFORMATION: 6D10-1-1 VL CDR3

<400> SEQUENCE: 59

Gln Gln Tyr Ile Asn Leu Pro Leu Thr
1               5

<210> SEQ ID NO 60
<211> LENGTH: 5
<212> TYPE: PRT
<213> ORGANISM: Artificial
<220> FEATURE:
<223> OTHER INFORMATION: 10D5-2-3 VH CDR1

<400> SEQUENCE: 60

Asn Tyr Trp Met Asn
1               5

<210> SEQ ID NO 61
<211> LENGTH: 19
<212> TYPE: PRT
<213> ORGANISM: Artificial
<220> FEATURE:
<223> OTHER INFORMATION: 10D5-2-3 VH CDR2

<400> SEQUENCE: 61

His Ile Arg Leu Lys Ser Asp Asn Tyr Ala Thr His Tyr Ala Glu Ser
1               5                   10                  15

Val Arg Gly

<210> SEQ ID NO 62
<211> LENGTH: 8
<212> TYPE: PRT
<213> ORGANISM: Artificial
<220> FEATURE:
<223> OTHER INFORMATION: 10D5-2-3 VH CDR3

<400> SEQUENCE: 62

Gly Ser Asn Tyr Val Phe Ala Phe
1               5

<210> SEQ ID NO 63
<211> LENGTH: 15
<212> TYPE: PRT
<213> ORGANISM: Artificial
<220> FEATURE:
<223> OTHER INFORMATION: 10D5-2-3 VL CDR1

<400> SEQUENCE: 63

Arg Ala Ser Glu Ser Val Asp Asn Tyr Gly Ile Ser Phe Met Asn
1               5                   10                  15

<210> SEQ ID NO 64
<211> LENGTH: 7
<212> TYPE: PRT
<213> ORGANISM: Artificial
<220> FEATURE:
<223> OTHER INFORMATION: 10D5-2-3 VL CDR2

<400> SEQUENCE: 64

Ala Ala Ser Asn Gln Gly Ser
1               5

<210> SEQ ID NO 65
<211> LENGTH: 9
<212> TYPE: PRT
<213> ORGANISM: Artificial

<220> FEATURE:
<223> OTHER INFORMATION: 10D5-2-3 VL CDR3

<400> SEQUENCE: 65

Gln Gln Ser Lys Glu Val Pro Trp Thr
1               5

<210> SEQ ID NO 66
<211> LENGTH: 429
<212> TYPE: PRT
<213> ORGANISM: Homo sapiens

<400> SEQUENCE: 66

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

```
Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 67
<211> LENGTH: 110
<212> TYPE: PRT
<213> ORGANISM: Artificial
<220> FEATURE:
<223> OTHER INFORMATION: hBMP9 mature region amino acids

<400> SEQUENCE: 67

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110

<210> SEQ ID NO 68
<211> LENGTH: 1290
<212> TYPE: DNA
<213> ORGANISM: Homo sapiens

<400> SEQUENCE: 68
atgtgtcctg gggcactgtg ggtggccctg cccctgctgt ccctgctggc tggctcccta    60
caggggaagc cactgcagag ctggggacga gggtctgctg ggggaaacgc ccacagccca   120 ctggggtgc ctggaggtgg gctgcctgag cacaccttca acctgaagat gtttctggag   180
aacgtgaagg tggatttcct cgcagccctt aacctgagtg ggtcccttc gcaggacaaa   240 accagggtgg agccgccgca gtacatgatt gacctgtaca acaggtacac gtccgataag   300
tcgactacgc cagcgtccaa cattgtgcgg agcttcagca tggaagatgc catctccata   360
actgccacag aggacttccc cttccagaag cacatcttgc tcttcaacat ctccattcct   420
aggcatgagc agatcaccag agctgagctc cgactctatg tctcctgtca aaatcacgtg   480
gacccctctc atgacctgaa aggaagcgtg gtcatttatg atgttctgga tggaacagat   540
gcctgggata gtgctacaga gaccaagacc ttcctggtgt cccaggacat tcaggatgag   600
ggctgggaga ccttggaagt gtccagcgcc gtgaagcgct gggtccggtc cgactccacc   660
```

```
aagagcaaaa ataagctgga agtgactgtg gagagccaca ggaagggctg cgacacgctg    720
gacatcagtg tccccccagg ttccagaaac ctgcccttct tgttgtctt ctccaatgac     780 cacagcagtg ggaccaagga gaccaggctg gagctgaggg agatgatcag ccatgaacaa    840
gagagcgtgc tcaagaagct gtccaaggac ggctccacag aggcaggtga gagcagtcac    900
gaggaggaca cggatggcca cgtggctgcg gggtcgactt tagccaggcg gaaaaggagc    960
gccggggctg cagccactg tcaaaagacc tccctgcggg taaacttcga ggacatcggc    1020
tgggacagct ggatcattgc acccaaggag tatgaagcct acgagtgtaa gggcggctgc   1080
ttcttcccct tggctgacga tgtgacgccg acgaaacacg ctatcgtgca gaccctggtg   1140
catctcaagt tccccacaaa ggtgggcaag gcctgctgtg tgcccaccaa actgagcccc   1200
atctccgtcc tctacaagga tgacatgggg gtgcccaccc tcaagtacca ttacgagggc   1260
atgagcgtgg cagagtgtgg gtgcaggtag                                    1290

<210> SEQ ID NO 69
<211> LENGTH: 333
<212> TYPE: DNA
<213> ORGANISM: Artificial
<220> FEATURE:
<223> OTHER INFORMATION: hBMP9 mature region

<400> SEQUENCE: 69
agcgccgggg ctggcagcca ctgtcaaaag acctccctgc gggtaaactt cgaggacatc     60
ggctgggaca gctggatcat tgcacccaag gagtatgaag cctacgagtg taagggcggc    120
tgcttcttcc ccttggctga cgatgtgacg ccgacgaaac acgctatcgt gcagaccctg    180
gtgcatctca gttccccac aaaggtgggc aaggcctgct gtgtgcccac caaactgagc     240 ccatctccg tcctctacaa ggatgacatg ggggtgccca ccctcaagta ccattacgag     300
ggcatgagcg tggcagagtg tgggtgcagg tag                                 333

<210> SEQ ID NO 70
<211> LENGTH: 1038
<212> TYPE: PRT
<213> ORGANISM: Homo sapiens

<400> SEQUENCE: 70

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140
```

```
Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
```

-continued

```
            565                 570                 575
Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
            595                 600                 605

Ser Thr Asn Thr Thr Thr Thr Asn Thr Thr Gly Leu Thr Pro Ser Thr
            610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
            675                 680                 685

Ser Leu Lys Gln Phe Ser Gly Pro Asp Pro Leu Ser Ser Thr Ser Ser
            690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
            755                 760                 765

Pro Arg Leu Lys Phe Gly Ser Lys His Lys Ser Asn Leu Lys Gln Val
            770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
            835                 840                 845

Asn Gln Phe Ile Gly Glu Asp Thr Arg Leu Asn Ile Asn Ser Ser Pro
            850                 855                 860

Asp Glu His Glu Pro Leu Leu Arg Arg Glu Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
            915                 920                 925

Pro Ser Lys Pro Arg Arg Ala Gln Arg Pro Asn Ser Leu Asp Leu Ser
            930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990
```

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly
    1010                1015                1020

Thr Ala Thr Thr Met Val Ser Lys Asp Ile Gly Met Asn Cys Leu
    1025                1030                1035

<210> SEQ ID NO 71
<211> LENGTH: 503
<212> TYPE: PRT
<213> ORGANISM: Homo sapiens

<400> SEQUENCE: 71

Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Lys Gly Pro Thr Cys Arg Gly
        35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
        115                 120                 125

Leu Leu Ala Leu Val Ala Leu Gly Val Leu Gly Leu Trp His Val Arg
    130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205

Gly Lys Gly Arg Tyr Gly Glu Val Trp Arg Gly Leu Trp His Gly Glu
    210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
    290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val

```
                    325                 330                 335

Leu Val Lys Ser Asn Leu Gln Cys Cys Ile Ala Asp Leu Gly Leu Ala
                340                 345                 350

Val Met His Ser Gln Gly Ser Asp Tyr Leu Asp Ile Gly Asn Asn Pro
            355                 360                 365

Arg Val Gly Thr Lys Arg Tyr Met Ala Pro Glu Val Leu Asp Glu Gln
        370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500

<210> SEQ ID NO 72
<211> LENGTH: 41
<212> TYPE: DNA
<213> ORGANISM: Artificial Sequence
<220> FEATURE:
<223> OTHER INFORMATION: 6D10-1-1 LC primer Fwd

<400> SEQUENCE: 72
acgccatcac agatctcacc atgatgtcct ctgctcagtt c                    41

<210> SEQ ID NO 73
<211> LENGTH: 35
<212> TYPE: DNA
<213> ORGANISM: Artificial Sequence
<220> FEATURE:
<223> OTHER INFORMATION: 6D10-1-1 LC primer Rv

<400> SEQUENCE: 73
cagcatcagc cgtacgtttc agctccagct tggtc                           35

<210> SEQ ID NO 74
<211> LENGTH: 40
<212> TYPE: DNA
<213> ORGANISM: Artificial Sequence
<220> FEATURE:
<223> OTHER INFORMATION: 6D10-1-1 HC primer Fwd

<400> SEQUENCE: 74
acacagaccc gtcgaccacc atggaatgga gcagagtctt                      40

<210> SEQ ID NO 75
<211> LENGTH: 38
<212> TYPE: DNA
<213> ORGANISM: Artificial Sequence
<220> FEATURE:
<223> OTHER INFORMATION: 6D10-1-1 HC primer Rv
```

<400> SEQUENCE: 75
tcgttttggc gctagctgag gagactgtga gagtggtg                                    38

<210> SEQ ID NO 76
<211> LENGTH: 41
<212> TYPE: DNA
<213> ORGANISM: Artificial Sequence
<220> FEATURE:
<223> OTHER INFORMATION: 10D5-2-3 LC primer Fwd

<400> SEQUENCE: 76
acgccatcac agatctcacc atggagaaag acacactcct g                                41

<210> SEQ ID NO 77
<211> LENGTH: 39
<212> TYPE: DNA
<213> ORGANISM: Artificial Sequence
<220> FEATURE:
<223> OTHER INFORMATION: 10D5-2-3 LC primer Rv

<400> SEQUENCE: 77
cagcatcagc cgtacgcttg atttccagct tggtgcctc                                   39

<210> SEQ ID NO 78
<211> LENGTH: 40
<212> TYPE: DNA
<213> ORGANISM: Artificial Sequence
<220> FEATURE:
<223> OTHER INFORMATION: 10D5-2-3 HC primer Fwd

<400> SEQUENCE: 78
acacagaccc gtcgaccacc atggacttga gactgagctg                                  40

<210> SEQ ID NO 79
<211> LENGTH: 36
<212> TYPE: DNA
<213> ORGANISM: Artificial Sequence
<220> FEATURE:
<223> OTHER INFORMATION: 10D5-2-3 HC primer Fwd

<400> SEQUENCE: 79
tcgttttggc gctagctgca gagacagtga ccagag                                      36

<210> SEQ ID NO 80
<211> LENGTH: 324
<212> TYPE: DNA
<213> ORGANISM: Mus musculus

<400> SEQUENCE: 80
cgggctgatg ctgcaccaac tgtatccatc ttcccaccat ccagtgagca gttaacatct            60
ggaggtgcct cagtcgtgtg cttcttgaac aacttctacc ccaaagacat caatgtcaag           120
tggaagattg atggcagtga acgacaaaat ggcgtcctga acagttggac tgatcaggac           180
agcaaagaca gcacctacag catgagcagc accctcacgt tgaccaagga cgagtatgaa           240
cgacataaca gctatacctg tgaggccact cacaagacat caacttcacc cattgtcaag           300
agcttcaaca ggaatgagtg ttga                                                  324

<210> SEQ ID NO 81
<211> LENGTH: 975
<212> TYPE: DNA
<213> ORGANISM: Mus musculus

<400> SEQUENCE: 81

```
gccaaaacga caccccatc tgtctatcca ctggccctg gatctgctgc ccaaactaac      60
tccatggtga ccctgggatg cctggtcaag ggctatttcc ctgagccagt gacagtgacc    120
tggaactctg gctccctgtc cagcggtgtg cacaccttcc cagctgtcct ggagtctgac    180
ctctacactc tgagcagctc agtgactgtc ccctccagcc ctcggcccag cgagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc taaggtcac gtgtgttgtg     420 gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatgaacac gaatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aatga                                                    975

<210> SEQ ID NO 82
<211> LENGTH: 24
<212> TYPE: DNA
<213> ORGANISM: Artificial Sequence
<220> FEATURE:
<223> OTHER INFORMATION: Mouse kappa CR primer Fwd

<400> SEQUENCE: 82
gtacggctga tgctgcacca actg                                           24

<210> SEQ ID NO 83
<211> LENGTH: 36
<212> TYPE: DNA
<213> ORGANISM: Artificial Sequence
<220> FEATURE:
<223> OTHER INFORMATION: Mouse kappa CR primer Rv

<400> SEQUENCE: 83
taacggatct gaattcaaca ctcattcctg ttgaag                              36

<210> SEQ ID NO 84
<211> LENGTH: 29
<212> TYPE: DNA
<213> ORGANISM: Artificial Sequence
<220> FEATURE:
<223> OTHER INFORMATION: Mouse IgG1 CR primer Fwd

<400> SEQUENCE: 84
ctagcgccaa aacgacaccc ccatctgtc                                      29

<210> SEQ ID NO 85
<211> LENGTH: 38
<212> TYPE: DNA
<213> ORGANISM: Artificial Sequence
<220> FEATURE:
<223> OTHER INFORMATION: Mouse IgG1 CR primer Rv
```

```
<400> SEQUENCE: 85
aaccgttaac ggatcctcat ttaccaggag agtgggag                              38

<210> SEQ ID NO 86
<211> LENGTH: 36
<212> TYPE: PRT
<213> ORGANISM: Artificial Sequence
<220> FEATURE:
<223> OTHER INFORMATION: Human BMP9 region C

<400> SEQUENCE: 86
```

Val Pro Thr Lys Leu Ser Pro Ile Ser Val Leu Tyr Lys Asp Asp Met
1               5                   10                  15

Gly Val Pro Thr Leu Lys Tyr His Tyr Glu Gly Met Ser Val Ala Glu
            20                  25                  30

Cys Gly Cys Arg
        35

```
<210> SEQ ID NO 87
<211> LENGTH: 35
<212> TYPE: PRT
<213> ORGANISM: Artificial Sequence
<220> FEATURE:
<223> OTHER INFORMATION: Human BMP9/BMP10 chimera-1 region C

<400> SEQUENCE: 87
```

Val Pro Thr Lys Leu Ser Pro Ile Ser Val Leu Tyr Leu Asp Lys Gly
1               5                   10                  15

Val Val Thr Leu Lys Tyr His Tyr Glu Gly Met Ser Val Ala Glu Cys
            20                  25                  30

Gly Cys Arg
        35

```
<210> SEQ ID NO 88
<211> LENGTH: 36
<212> TYPE: PRT
<213> ORGANISM: Artificial Sequence
<220> FEATURE:
<223> OTHER INFORMATION: Human BMP9/BMP10 chimera-2 region C

<400> SEQUENCE: 88
```

Val Pro Thr Lys Leu Ser Pro Ile Ser Ile Leu Tyr Lys Asp Asp Met
1               5                   10                  15

Gly Val Pro Thr Tyr Lys Phe Lys Tyr Glu Gly Met Ser Val Ala Glu
            20                  25                  30

Cys Gly Cys Arg
        35

```
<210> SEQ ID NO 89
<211> LENGTH: 36
<212> TYPE: PRT
<213> ORGANISM: Artificial Sequence
<220> FEATURE:
<223> OTHER INFORMATION: Human BMP9/BMP10 chimera-3 region C

<400> SEQUENCE: 89
```

Val Pro Thr Lys Leu Glu Pro Ile Ser Val Leu Tyr Lys Asp Asp Met
1               5                   10                  15

Gly Val Pro Thr Leu Lys Tyr His Tyr Glu Gly Met Ala Val Ser Glu
            20                  25                  30

Cys Gly Cys Arg
        35

<210> SEQ ID NO 90
<211> LENGTH: 35
<212> TYPE: PRT
<213> ORGANISM: Artificial Sequence
<220> FEATURE:
<223> OTHER INFORMATION: Human BMP9/BMP10 chimera-4 region C

<400> SEQUENCE: 90

Val Pro Thr Lys Leu Ser Pro Ile Ser Ile Leu Tyr Leu Asp Lys Gly
1               5                   10                  15

Val Val Thr Tyr Lys Phe Lys Tyr Glu Gly Met Ser Val Ala Glu Cys
            20                  25                  30

Gly Cys Arg
        35

<210> SEQ ID NO 91
<211> LENGTH: 36
<212> TYPE: PRT
<213> ORGANISM: Artificial Sequence
<220> FEATURE:
<223> OTHER INFORMATION: Human BMP9/BMP10 chimera-5 region C

<400> SEQUENCE: 91

Val Pro Thr Lys Leu Glu Pro Ile Ser Ile Leu Tyr Lys Asp Asp Met
1               5                   10                  15

Gly Val Pro Thr Tyr Lys Phe Lys Tyr Glu Gly Met Ala Val Ser Glu
            20                  25                  30

Cys Gly Cys Arg
        35

<210> SEQ ID NO 92
<211> LENGTH: 86
<212> TYPE: DNA
<213> ORGANISM: Artificial Sequence
<220> FEATURE:
<223> OTHER INFORMATION: Chimera primer 1

<400> SEQUENCE: 92
caaaggtggg caaggcctgc tgtgtgccca ccaaactgag ccccatctcc gtcctctact    60
tagataaagg ggtggtcacc ctcaag                                         86

<210> SEQ ID NO 93
<211> LENGTH: 86
<212> TYPE: DNA
<213> ORGANISM: Artificial Sequence
<220> FEATURE:
<223> OTHER INFORMATION: Chimera primer 2

<400> SEQUENCE: 93
caaaggtggg caaggcctgc tgtgtgccca ccaaactgag ccccatctcc atcctctaca    60
aggatgacat gggggtgccc acctac                                         86

<210> SEQ ID NO 94
<211> LENGTH: 86
<212> TYPE: DNA
<213> ORGANISM: Artificial Sequence
<220> FEATURE:
<223> OTHER INFORMATION: Chimera primer 3

<400> SEQUENCE: 94
caaaggtggg caaggcctgc tgtgtgccca ccaaactgga gcccatctcc gtcctctaca    60
aggatgacat gggggtgccc accctc 86

<210> SEQ ID NO 95
<211> LENGTH: 86
<212> TYPE: DNA
<213> ORGANISM: Artificial Sequence
<220> FEATURE:
<223> OTHER INFORMATION: Chimera primer 4

<400> SEQUENCE: 95
caaaggtggg caaggcctgc tgtgtgccca ccaaactgag ccccatctcc atcctctact 60
tagataaagg ggtggtcacc tacaag 86

<210> SEQ ID NO 96
<211> LENGTH: 86
<212> TYPE: DNA
<213> ORGANISM: Artificial Sequence
<220> FEATURE:
<223> OTHER INFORMATION: Chimera primer 5

<400> SEQUENCE: 96
caaaggtggg caaggcctgc tgtgtgccca ccaaactgga gcccatctcc atcctctaca 60
aggatgacat gggggtgccc acctac 86

<210> SEQ ID NO 97
<211> LENGTH: 79
<212> TYPE: DNA
<213> ORGANISM: Artificial Sequence
<220> FEATURE:
<223> OTHER INFORMATION: Chimera primer 6

<400> SEQUENCE: 97
tcatgtctcg ctcgagctac ctgcacccac actctgccac gctcatgccc tcgtaatggt 60
acttgagggt gaccaccccc 79

<210> SEQ ID NO 98
<211> LENGTH: 79
<212> TYPE: DNA
<213> ORGANISM: Artificial Sequence
<220> FEATURE:
<223> OTHER INFORMATION: Chimera primer 7

<400> SEQUENCE: 98
tcatgtctcg ctcgagctac ctgcacccac actctgccac gctcatgccc tcgtatttaa 60
acttgtaggt gggcacccc 79

<210> SEQ ID NO 99
<211> LENGTH: 79
<212> TYPE: DNA
<213> ORGANISM: Artificial Sequence
<220> FEATURE:
<223> OTHER INFORMATION: Chimera primer 8

<400> SEQUENCE: 99
tcatgtctcg ctcgagctac ctgcacccac actcggacac ggccatgccc tcgtaatggt 60
acttgagggt gggcacccc 79

<210> SEQ ID NO 100
<211> LENGTH: 79
<212> TYPE: DNA
<213> ORGANISM: Artificial Sequence
<220> FEATURE:
<223> OTHER INFORMATION: Chimera primer 9

<400> SEQUENCE: 100
tcatgtctcg ctcgagctac ctgcacccac actctgccac gctcatgccc tcgtatttaa    60
acttgtaggt gaccacccc                                                 79

<210> SEQ ID NO 101
<211> LENGTH: 79
<212> TYPE: DNA
<213> ORGANISM: Artificial Sequence
<220> FEATURE:
<223> OTHER INFORMATION: Chimera primer 10

<400> SEQUENCE: 101
tcatgtctcg ctcgagctac ctgcacccac actcggacac ggccatgccc tcgtatttaa    60
acttgtaggt gggcacccc                                                 79

<210> SEQ ID NO 102
<211> LENGTH: 44
<212> TYPE: DNA
<213> ORGANISM: Artificial Sequence
<220> FEATURE:
<223> OTHER INFORMATION: Human BMP10 Primer Fwd-1

<400> SEQUENCE: 102
cccgggatcc gctagccggc caccatgggc tctctggtcc tgac                     44

<210> SEQ ID NO 103
<211> LENGTH: 44
<212> TYPE: DNA
<213> ORGANISM: Artificial Sequence
<220> FEATURE:
<223> OTHER INFORMATION: Human BMP10 Primer Rv-1

<400> SEQUENCE: 103
gatggggcta tggtgatggt gatgatggcc agaaaccaag taag                     44

<210> SEQ ID NO 104
<211> LENGTH: 32
<212> TYPE: DNA
<213> ORGANISM: Artificial Sequence
<220> FEATURE:
<223> OTHER INFORMATION: Human BMP10 Primer Fwd-2

<400> SEQUENCE: 104
caccatagcc ccatcatgaa cctagagcag tc                                  32

<210> SEQ ID NO 105
<211> LENGTH: 40
<212> TYPE: DNA
<213> ORGANISM: Artificial Sequence
<220> FEATURE:
<223> OTHER INFORMATION: Human BMP10 Primer Rv-2

<400> SEQUENCE: 105
tcatgtctcg ctcgagctat ctacagccac attcggagac                          40

<210> SEQ ID NO 106
<211> LENGTH: 424
<212> TYPE: PRT
<213> ORGANISM: Homo sapiens

<400> SEQUENCE: 106

Met Gly Ser Leu Val Leu Thr Leu Cys Ala Leu Phe Cys Leu Ala Ala
1               5                   10                  15

```
Tyr Leu Val Ser Gly Ser Pro Ile Met Asn Leu Glu Gln Ser Pro Leu
             20                  25                  30

Glu Glu Asp Met Ser Leu Phe Gly Asp Val Phe Ser Glu Gln Asp Gly
         35                  40                  45

Val Asp Phe Asn Thr Leu Leu Gln Ser Met Lys Asp Glu Phe Leu Lys
 50                  55                  60

Thr Leu Asn Leu Ser Asp Ile Pro Thr Gln Asp Ser Ala Lys Val Asp
 65                  70                  75                  80

Pro Pro Glu Tyr Met Leu Glu Leu Tyr Asn Lys Phe Ala Thr Asp Arg
             85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
            115                 120                 125

Leu Phe Asn Val Ser Ile Pro His His Glu Glu Val Ile Met Ala Glu
130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
            195                 200                 205

Arg Trp Gln Lys Ser Gly Ser Ser Thr His Gln Leu Glu Val His Ile
            210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
            275                 280                 285

Ser Phe Ser Ser Gly Pro Gly Glu Glu Ala Leu Leu Gln Met Arg Ser
            290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
            355                 360                 365

His Ala Ile Ile Gln Ala Leu Val His Leu Lys Asn Ser Gln Lys Ala
            370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420
```

<210> SEQ ID NO 107
<211> LENGTH: 108
<212> TYPE: PRT
<213> ORGANISM: Artificial Sequence
<220> FEATURE:
<223> OTHER INFORMATION: hBMP10 mature region amino acids

<400> SEQUENCE: 107

```
Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
        35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105
```

<210> SEQ ID NO 108
<211> LENGTH: 1275
<212> TYPE: DNA
<213> ORGANISM: Homo sapiens

<400> SEQUENCE: 108

| | | | | |
|---|---|---|---|---|
| atgggctctc | tggtcctgac | actgtgcgct | cttttctgcc | tggcagctta cttggttttct | 60 |
| ggcagcccca | tcatgaacct | agagcagtct | cctctggaag | aagatatgtc cctcttttggt | 120 |
| gatgttttct | cagagcaaga | cggtgtcgac | tttaacacac | tgctccagag catgaaggat | 180 |
| gagtttctta | agacactaaa | cctctctgac | atccccacgc | aggattcagc caaggtggac | 240 |
| ccaccagagt | acatgttgga | actctacaac | aaatttgcaa | cagatcggac ctccatgccc | 300 |
| tctgccaaca | tcattaggag | tttcaagaat | gaagatctgt | tttcccagcc ggtcagtttt | 360 |
| aatgggctcc | gaaataccc | cctcctcttc | aatgtgtcca | ttcctcacca tgaagaggtc | 420 |
| atcatggctg | aacttaggct | atacacactg | gtgcaagggg | atcgtatgat atacgatgga | 480 |
| gtagaccgga | aaattaccat | ttttgaagtg | ctggagagca | aggggataa tgagggagaa | 540 |
| agaaacatgc | tggtcttggt | gtctggggag | atatatggaa | ccaacagtga gtgggagact | 600 |
| tttgatgtca | cagatgccat | cagacgttgg | caaaagtcag | gctcatccac ccaccagctg | 660 |
| gaggtccaca | ttgagagcaa | acacgatgaa | gctgaggatg | ccagcagtgg acggctagaa | 720 |
| atagatacca | gtgcccagaa | taagcataac | ccttttgctca | tcgtgttttc tgatgaccaa | 780 |
| agcagtgaca | aggagaggaa | ggaggaactg | aatgaaatga | tttcccatga gcaacttcca | 840 |
| gagctggaca | acttgggcct | ggatagcttt | tccagtggac | ctgggaaga ggctttgttg | 900 |
| cagatgagat | caaacatcat | ctatgactcc | actgcccgaa | tcagaaggaa cgccaaagga | 960 |
| aactactgta | agaggacccc | gctctacatc | gacttcaagg | agattgggtg ggactcctgg | 1020 |
| atcatcgctc | cgcctggata | cgaagcctat | gaatgccgtg | tgtttgtaa ctaccccctg | 1080 |
| gcagagcatc | tcacacccac | aaagcatgca | attatccagg | ccttggtcca cctcaagaat | 1140 |
| tcccagaaag | cttccaaagc | ctgctgtgtg | cccacaaagc | tagagcccat ctccatcctc | 1200 |

```
tatttagaca aaggcgtcgt cacctacaag tttaaatacg aaggcatggc cgtctccgaa    1260
tgtggctgta gatag                                                    1275
```

<210> SEQ ID NO 109
<211> LENGTH: 327
<212> TYPE: DNA
<213> ORGANISM: Artificial Sequence
<220> FEATURE:
<223> OTHER INFORMATION: hBMP10 mature region

<400> SEQUENCE: 109

```
aacgccaaag gaaactactg taagaggacc ccgctctaca tcgacttcaa ggagattggg      60
tgggactcct ggatcatcgc tccgcctgga tacgaagcct atgaatgccg tggtgtttgt    120
aactaccccc tggcagagca tctcacaccc acaaagcatg caattatcca ggccttggtc    180
cacctcaaga attcccagaa agcttccaaa gcctgctgtg tgcccacaaa gctagagccc    240
atctccatcc tctatttaga caaggcgtc gtcacctaca gtttaaata cgaaggcatg     300 gccgtctccg aatgtggctg tagatag                                       327
```

<210> SEQ ID NO 110
<211> LENGTH: 430
<212> TYPE: PRT
<213> ORGANISM: Artificial Sequence
<220> FEATURE:
<223> OTHER INFORMATION: pLN1V5_hBMP10 amino acids

<400> SEQUENCE: 110

```
Met Gly Ser Leu Val Leu Thr Leu Cys Ala Leu Phe Cys Leu Ala Ala
1               5                   10                  15

Tyr Leu Val Ser Gly His His His His His His Ser Pro Ile Met Asn
            20                  25                  30

Leu Glu Gln Ser Pro Leu Glu Glu Asp Met Ser Leu Phe Gly Asp Val
        35                  40                  45

Phe Ser Glu Gln Asp Gly Val Asp Phe Asn Thr Leu Leu Gln Ser Met
    50                  55                  60

Lys Asp Glu Phe Leu Lys Thr Leu Asn Leu Ser Asp Ile Pro Thr Gln
65                  70                  75                  80

Asp Ser Ala Lys Val Asp Pro Pro Glu Tyr Met Leu Glu Leu Tyr Asn
                85                  90                  95

Lys Phe Ala Thr Asp Arg Thr Ser Met Pro Ser Ala Asn Ile Ile Arg
            100                 105                 110

Ser Phe Lys Asn Glu Asp Leu Phe Ser Gln Pro Val Ser Phe Asn Gly
        115                 120                 125

Leu Arg Lys Tyr Pro Leu Leu Phe Asn Val Ser Ile Pro His His Glu
    130                 135                 140

Glu Val Ile Met Ala Glu Leu Arg Leu Tyr Thr Leu Val Gln Arg Asp
145                 150                 155                 160

Arg Met Ile Tyr Asp Gly Val Asp Arg Lys Ile Thr Ile Phe Glu Val
                165                 170                 175

Leu Glu Ser Lys Gly Asp Asn Glu Gly Glu Arg Asn Met Leu Val Leu
            180                 185                 190

Val Ser Gly Glu Ile Tyr Gly Thr Asn Ser Glu Trp Glu Thr Phe Asp
        195                 200                 205

Val Thr Asp Ala Ile Arg Arg Trp Gln Lys Ser Gly Ser Ser Thr His
    210                 215                 220

Gln Leu Glu Val His Ile Glu Ser Lys His Asp Glu Ala Glu Asp Ala
```

```
                    225                 230                 235                 240
            Ser Ser Gly Arg Leu Glu Ile Asp Thr Ser Ala Gln Asn Lys His Asn
                            245                 250                 255

Pro Leu Leu Ile Val Phe Ser Asp Asp Gln Ser Ser Asp Lys Glu Arg
                        260                 265                 270

Lys Glu Glu Leu Asn Glu Met Ile Ser His Glu Gln Leu Pro Glu Leu
                        275                 280                 285

Asp Asn Leu Gly Leu Asp Ser Phe Ser Ser Gly Pro Gly Glu Glu Ala
                    290                 295                 300

Leu Leu Gln Met Arg Ser Asn Ile Ile Tyr Asp Ser Thr Ala Arg Ile
            305                 310                 315                 320

Arg Arg Asn Ala Lys Gly Asn Tyr Cys Lys Arg Thr Pro Leu Tyr Ile
                            325                 330                 335

Asp Phe Lys Glu Ile Gly Trp Asp Ser Trp Ile Ile Ala Pro Pro Gly
                        340                 345                 350

Tyr Glu Ala Tyr Glu Cys Arg Gly Val Cys Asn Tyr Pro Leu Ala Glu
                        355                 360                 365

His Leu Thr Pro Thr Lys His Ala Ile Ile Gln Ala Leu Val His Leu
                    370                 375                 380

Lys Asn Ser Gln Lys Ala Ser Lys Ala Cys Cys Val Pro Thr Lys Leu
            385                 390                 395                 400

Glu Pro Ile Ser Ile Leu Tyr Leu Asp Lys Gly Val Val Thr Tyr Lys
                            405                 410                 415

Phe Lys Tyr Glu Gly Met Ala Val Ser Glu Cys Gly Cys Arg
                        420                 425                 430

<210> SEQ ID NO 111
<211> LENGTH: 1293
<212> TYPE: DNA
<213> ORGANISM: Artificial Sequence
<220> FEATURE:
<223> OTHER INFORMATION: pLN1V5_hBMP10

<400> SEQUENCE: 111
atgggctctc tggtcctgac actgtgcgct cttttctgcc tggcagctta cttggtttct      60
ggccatcatc accatcacca tagccccatc atgaacctag agcagtctcc tctggaagaa     120
gatatgtccc tctttggtga tgttttctca gagcaagacg tgtcgactt  taacacactg     180 ctccagagca tgaaggatga gtttcttaag acactaaacc tctctgacat ccccacgcag     240
gattcagcca aggtggaccc accagagtac atgttggaac tctacaacaa atttgcaaca     300
gatcggacct ccatgccctc tgccaacatc attaggagtt caagaatga  agatctgttt     360 tcccagccgg tcagtttaa  tgggctccga aaataccccc tcctcttcaa tgtgtccatt     420
cctcaccatg aagaggtcat catggctgaa cttaggctat acacactggt gcaaagggat     480
cgtatgatat acgatggagt agaccggaaa attaccattt ttgaagtgct ggagagcaaa     540
ggggataatg agggagaaag aaacatgctg gtcttggtgt ctggggagat atatggaacc     600
aacagtgagt gggagacttt tgatgtcaca gatgccatca  acgttggca aaagtcaggc     660 tcatccaccc accagctgga ggtccacatt gagagcaaac acgatgaagc tgaggatgcc     720
agcagtggac ggctagaaat agataccagt gcccagaata gcataaccc  tttgctcatc     780 gtgttttctg atgaccaaag cagtgacaag gagaggaagg aggaactgaa tgaaatgatt     840
tcccatgagc aacttccaga gctggacaac ttggcctgg  atagcttttc cagtggacct     900
ggggaagagg ctttgttgca gatgagatca  acatcatct  atgactccac tgcccgaatc     960
```

-continued

```
agaaggaacg ccaaaggaaa ctactgtaag aggaccccgc tctacatcga cttcaaggag      1020
attgggtggg actcctggat catcgctccg cctggatacg aagcctatga atgccgtggt      1080
gtttgtaact accccctggc agagcatctc acacccacaa agcatgcaat tatccaggcc      1140
ttggtccacc tcaagaattc ccagaaagct tccaaagcct gctgtgtgcc cacaaagcta      1200
gagcccatct ccatcctcta tttagacaaa ggcgtcgtca cctacaagtt taaatacgaa      1260
ggcatggccg tctccgaatg tggctgtaga tag                                   1293
```

<210> SEQ ID NO 112
<211> LENGTH: 1512
<212> TYPE: DNA
<213> ORGANISM: Homo sapiens

<400> SEQUENCE: 112

```
atgaccttgg gctcccccag gaaaggcctt ctgatgctgc tgatggcctt ggtgacccag        60
ggagaccctg tgaagccgtc tcggggcccg ctggtgacct gcacgtgtga gagcccacat       120 tgcaagggc ctacctgccg ggggcctgg tgcacagtag tgctggtgcg ggaggagggg         180 aggcacccc aggaacatcg gggctgcggg aacttgcaca gggagctctg caggggcgc         240 cccaccgagt tcgtcaacca ctactgctgc gacagccacc tctgcaacca caacgtgtcc       300
ctggtgctgg aggccaccca acctccttcg gagcagccgg aacagatgg ccagctggcc        360 ctgatcctgg gccccgtgct ggccttgctg gccctggtgg ccctgggtgt cctgggcctg       420
tggcatgtcc gacggaggca ggagaagcag cgtggcctgc acagcgagct gggagagtcc       480
agtctcatcc tgaaagcatc tgagcagggc gacagcatgt tgggggacct cctggacagt       540
gactgcacca cagggagtgg ctcagggctc cccttcctgg tgcagaggac agtggcacgg       600
caggttgcct tggtggagtg tgtgggaaaa ggccgctatg gcgaagtgtg gcggggcttg       660
tggcacggtg agagtgtggc cgtcaagatc ttctcctcga gggatgaaca gtcctggttc       720
cgggagactg agatctataa cacagtgttg ctcagacacg acaacatcct aggcttcatc       780
gcctcagaca tgacctcccg caactcgagc acgcagctgt ggctcatcac gcactaccac       840
gagcacggct ccctctacga ctttctgcag agacagacgc tggagcccca tctggctctg       900
aggctagctg tgtccgcggc atgcggcctg cgcacctgc acgtggagat cttcggtaca       960
cagggcaaac cagccattgc ccaccgcgac ttcaagagcc gcaatgtgct ggtcaagagc      1020
aacctgcagt gttgcatcgc cgacctgggc ctggctgtga tgcactcaca gggcagcgat      1080
tacctggaca tcggcaacaa cccgagagtg ggaccaagc ggtacatggc acccgaggtg      1140
ctggacgagc agatccgcac ggactgcttt gagtcctaca gtggactga catctgggcc      1200 tttggcctgg tgctgtggga gattgcccgc cggaccatcg tgaatggcat cgtggaggac      1260
tatagaccac ccttctatga tgtggtgccc aatgacccca gctttgagga catgaagaag      1320
gtggtgtgtg tggatcagca gacccccacc atccctaacc ggctggctgc agacccggtc      1380
ctctcaggcc tagctcagat gatgcgggag tgctggtacc caaacccctc tgcccgactc      1440
accgcgctgc ggatcaagaa gacactacaa aaaattagca acagtccaga gaagcctaaa      1500
gtgattcaat ag                                                        1512
```

<210> SEQ ID NO 113
<211> LENGTH: 32
<212> TYPE: DNA
<213> ORGANISM: Artificial Sequence
<220> FEATURE:

<223> OTHER INFORMATION: shALK1 FPN

<400> SEQUENCE: 113
agaattccca ccatgacctt gggctccccc ag                                      32

<210> SEQ ID NO 114
<211> LENGTH: 27
<212> TYPE: DNA
<213> ORGANISM: Artificial Sequence
<220> FEATURE:
<223> OTHER INFORMATION: hALK1 RP

<400> SEQUENCE: 114
gcggccgcct attgaatcac tttaggc                                            27

<210> SEQ ID NO 115
<211> LENGTH: 357
<212> TYPE: DNA
<213> ORGANISM: Artificial Sequence
<220> FEATURE:
<223> OTHER INFORMATION: HV0

<400> SEQUENCE: 115
gaagtgcagc ttgtggagtc tggcggaggc ttggtgcaac ctggaggatc cctgcggctc        60
tcctgtgccg cctctggatt cactttcagt aactactgga tgaactgggt ccgccaggcc      120
ccaggcaagg ggcttgagtg ggttggccac attagattaa aatctgataa ttatgcaaca      180
cattatgcgg agtctgtgag agggaggttc actatctcaa gagatgattc aaaaacagt      240 ctgtacctgc aaatgaactc cttaaagacc gaagacactg ccgtgtatta ctgcgcccgg      300
ggaagtaact acgtgtttgc tttctggggc caagggactc tggtcactgt ctcttcc         357

<210> SEQ ID NO 116
<211> LENGTH: 119
<212> TYPE: PRT
<213> ORGANISM: Artificial Sequence
<220> FEATURE:
<223> OTHER INFORMATION: HV0 amino acids

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Ser Asn Tyr Val Phe Ala Phe Trp Gly Gln Gly
            100                 105                 110

Thr Leu Val Thr Val Ser Ser
        115

<210> SEQ ID NO 117
<211> LENGTH: 333
<212> TYPE: DNA
<213> ORGANISM: Artificial Sequence

<220> FEATURE:
<223> OTHER INFORMATION: LV0

<400> SEQUENCE: 117

```
gacattgtga tgacccaatc tccagactct ttggctgtgt ctctagggga gagggccacc    60
atcaactgca gagccagcga aagtgttgat aattatggca ttagttttat gaactggtac   120
caacagaaac caggacagcc acccaaactc ctcatctatg ctgcatccaa ccaaggatcc   180
ggggtccctg acaggtttag tggcagtggg tctgggacag acttcaccct caccatctcc   240
tccctgcagg ccgaggatgt ggcagtgtat tactgtcaac aaagtaagga ggttccgtgg   300
acgttcggtc agggcaccaa gctggaaatc aag                                333
```

<210> SEQ ID NO 118
<211> LENGTH: 111
<212> TYPE: PRT
<213> ORGANISM: Artificial Sequence
<220> FEATURE:
<223> OTHER INFORMATION: LV0 amino acids

<400> SEQUENCE: 118

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110

<210> SEQ ID NO 119
<211> LENGTH: 357
<212> TYPE: DNA
<213> ORGANISM: Artificial Sequence
<220> FEATURE:
<223> OTHER INFORMATION: HV3

<400> SEQUENCE: 119

```
gaagtgcagc ttgtggagtc tgcgggaggc ttggtgcaac ctggaggatc cctgcggctc    60
tcctgtgccg cctctggatt cactttcagt aactactgga tgaactgggt ccgccaggcc   120
ccaggcaagg ggcttgagtg ggttgctcac attagattaa aatctgataa ttatgcaaca   180
cattatgcgg agtctgtgag agggaggttc actatctcaa gagatgattc caaaaacagt   240
ctgtacctgc aaatgaactc cttaaagacc gaagacactg ccgtgtatta ctgcacagga   300
ggaagtaact acgtgtttgc tttctggggc caagggactc tggtcactgt ctcttcc     357
```

<210> SEQ ID NO 120
<211> LENGTH: 119
<212> TYPE: PRT
<213> ORGANISM: Artificial Sequence
<220> FEATURE:
<223> OTHER INFORMATION: HV3 amino acids

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ser
        115

<210> SEQ ID NO 121
<211> LENGTH: 357
<212> TYPE: DNA
<213> ORGANISM: Artificial Sequence
<220> FEATURE:
<223> OTHER INFORMATION: HV4a

<400> SEQUENCE: 121
gaagtgcagc ttgtggagtc tagaggaggc ttggtgcaac ctggaggatc catgcggctc      60
tcctgtgccg cctctggatt cactttcagt aactactgga tgaactgggt ccgccaggcc     120
ccaggcaagg ggcttgagtg ggttggccac attagattaa aatctgataa ttatgcaaca     180
cattatgcgg agtctgtgag agggaggttc actatctcaa gagatgattc caaaagtagt     240
ctgtacctgc aaatgaactc cttaaagacc gaagacactg ccgtgtatta ctgcgccgga     300
ggaagtaact acgtgtttgc tttctggggc caagggactc tggtcactgt ctcttcc        357

<210> SEQ ID NO 122
<211> LENGTH: 119
<212> TYPE: PRT
<213> ORGANISM: Artificial Sequence
<220> FEATURE:
<223> OTHER INFORMATION: HV4a amino acids

<400> SEQUENCE: 122

Glu Val Gln Leu Val Glu Ser Arg Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Val Tyr
                85                  90                  95

Tyr Cys Ala Gly Gly Ser Asn Tyr Val Phe Ala Phe Trp Gly Gln Gly
            100                 105                 110

Thr Leu Val Thr Val Ser Ser

```
<210> SEQ ID NO 123
<211> LENGTH: 357
<212> TYPE: DNA
<213> ORGANISM: Artificial Sequence
<220> FEATURE:
<223> OTHER INFORMATION: HV4b

<400> SEQUENCE: 123
gaagtgcagc ttgtggagtc tggcggaggc ttggtgcaac ctggaggatc cctgcggctc      60
tcctgtgccg cctctggatt cactttcagt aactactgga tgaactgggt ccgccaggcc     120
ccaggcaagg ggcttgagtg ggttgctcac attagattaa aatctgataa ttatgcaaca     180
cattatgcgg agtctgtgag agggaggttc actatctcaa gagatgattc caaaaacagt     240
ctgtacctgc aaatgaactc cttaaagacc gaagacactg ccatttatta ctgcacagga     300
ggaagtaact acgtgtttgc tttctggggc caagggactc tggtcactgt ctcttcc       357

<210> SEQ ID NO 124
<211> LENGTH: 119
<212> TYPE: PRT
<213> ORGANISM: Artificial Sequence
<220> FEATURE:
<223> OTHER INFORMATION: HV4b amino acids

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Ile Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ser
        115

<210> SEQ ID NO 125
<211> LENGTH: 357
<212> TYPE: DNA
<213> ORGANISM: Artificial Sequence
<220> FEATURE:
<223> OTHER INFORMATION: HV7a

<400> SEQUENCE: 125
gaagtgcagc ttgtggagtc tagaggaggc ttggtgcaac ctggaggatc catgcggctc      60
tcctgtgccg cctctggatt cactttcagt aactactgga tgaactgggt ccgccaggcc     120
ccaggcaagg ggcttgagtg ggttgctcac attagattaa aatctgataa ttatgcaaca     180
cattatgcgg agtctgtgag agggaggttc actatctcaa gagatgattc caaaagtagt     240
ctgtacctgc aaatgaactc cttaaagacc gaagacactg gagtgtatta ctgcacagga     300
ggaagtaact acgtgtttgc tttctggggc caagggactc tggtcactgt ctcttcc       357
```

<210> SEQ ID NO 126
<211> LENGTH: 119
<212> TYPE: PRT
<213> ORGANISM: Artificial Sequence
<220> FEATURE:
<223> OTHER INFORMATION: HV7a amino acids

<400> SEQUENCE: 126

Glu Val Gln Leu Val Glu Ser Arg Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Ser Ser
65                  70                  75                  80

Leu Tyr Leu Gln Met Asn Ser Leu Lys Thr Glu Asp Thr Gly Val Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ser
        115

<210> SEQ ID NO 127
<211> LENGTH: 357
<212> TYPE: DNA
<213> ORGANISM: Artificial Sequence
<220> FEATURE:
<223> OTHER INFORMATION: HV7b

<400> SEQUENCE: 127
gaagtgcagc ttgtggagtc tagaggaggc ttggtgcaac ctggaggatc catgcggctc      60
tcctgtgccg cctctggatt cactttcagt aactactgga tgaactgggt ccgccaggcc     120
ccaggcaagg ggcttgagtg ggttgctcac attagattaa aatctgataa ttatgcaaca     180
cattatgcgg agtctgtgag agggaggttc actatctcaa gagatgattc caaaaacagt     240
gtctacctgc aaatgaactc cttaaagacc gaagacactg gagtctatta ctgcacagga     300
ggaagtaact acgtgtttgc tttctggggc caagggactc tggtcactgt ctcttcc       357

<210> SEQ ID NO 128
<211> LENGTH: 119
<212> TYPE: PRT
<213> ORGANISM: Artificial Sequence
<220> FEATURE:
<223> OTHER INFORMATION: HV7b amino acids

<400> SEQUENCE: 128

Glu Val Gln Leu Val Glu Ser Arg Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala His Ile Arg Leu Lys Ser Asp Asn Tyr Ala Thr His Tyr Ala Glu
    50                  55                  60

Ser Val Arg Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ser
        115

<210> SEQ ID NO 129
<211> LENGTH: 357
<212> TYPE: DNA
<213> ORGANISM: Artificial Sequence
<220> FEATURE:
<223> OTHER INFORMATION: HV9

<400> SEQUENCE: 129
gaagtgcagc ttgtggagtc tagaggaggc ttggtgcaac ctggaggatc catgcggctc      60
tcctgtgccg cctctggatt cacttttcagt aactactgga tgaactgggt ccgccaggcc    120
ccaggcaagg ggcttgagtg ggttgctcac attagattaa aatctgataa ttatgcaaca    180
cattatgcgg agtctgtgag agggaggttc actatctcaa gagatgattc caaaagtagt    240
gtctacctgc aaatgaactc cttaaagacc gaagacactg gaatttatta ctgcacagga    300
ggaagtaact acgtgtttgc tttctggggc caagggactc tggtcactgt ctcttcc        357

<210> SEQ ID NO 130
<211> LENGTH: 119
<212> TYPE: PRT
<213> ORGANISM: Artificial Sequence
<220> FEATURE:
<223> OTHER INFORMATION: HV9 amino acids

<400> SEQUENCE: 130

Glu Val Gln Leu Val Glu Ser Arg Gly Gly Leu Val Gln Pro Gly Gly
1               5                   10                  15

Ser Met Arg Leu Ser Cys Ala Ala Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Ala His Ile Arg Leu Lys Ser Asp Asn Tyr Ala Thr His Tyr Ala Glu
        50                  55                  60

Ser Val Arg Gly Arg Phe Thr Ile Ser Arg Asp Asp Ser Lys Ser Ser
65                  70                  75                  80

Val Tyr Leu Gln Met Asn Ser Leu Lys Thr Glu Asp Thr Gly Ile Tyr
                85                  90                  95

Tyr Cys Thr Gly Gly Ser Asn Tyr Val Phe Ala Phe Trp Gly Gln Gly
            100                 105                 110

Thr Leu Val Thr Val Ser Ser
        115

<210> SEQ ID NO 131
<211> LENGTH: 333
<212> TYPE: DNA
<213> ORGANISM: Artificial Sequence
<220> FEATURE:
<223> OTHER INFORMATION: LV2

<400> SEQUENCE: 131
gacattgtga tgacccaatc tccagactct ttggctgtgt ctctagggga gagggccacc     60

```
atcaactgca gagccagcga aagtgttgat aattatggca ttagttttat gaactggttc     120
caacagaaac caggacagcc acccaaactc ctcatctatg ctgcatccaa ccaaggatcc     180
ggggtccctg acaggtttag tggcagtggg tctgggacag acttcaccct caccatctcc     240
tccctgcagg ccgaggatgt ggcagtgtat ttctgtcaac aaagtaagga ggttccgtgg     300
acgttcggtc agggcaccaa gctggaaatc aag                                  333
```

<210> SEQ ID NO 132
<211> LENGTH: 111
<212> TYPE: PRT
<213> ORGANISM: Artificial Sequence
<220> FEATURE:
<223> OTHER INFORMATION: LV2 amino acids

<400> SEQUENCE: 132

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Lys
                85                  90                  95

Glu Val Pro Trp Thr Phe Gly Gln Gly Thr Lys Leu Glu Ile Lys
            100                 105                 110
```

<210> SEQ ID NO 133
<211> LENGTH: 333
<212> TYPE: DNA
<213> ORGANISM: Artificial Sequence
<220> FEATURE:
<223> OTHER INFORMATION: LV3

<400> SEQUENCE: 133

```
gacattgtga tgacccaatc tccagactct ttggctgtgt ctctagggga gagggccacc      60
atcaactgca gagccagcga aagtgttgat aattatggca ttagttttat gaactggttc     120
caacagaaac caggacagcc acccaaactc ctcatctatg ctgcatccaa ccaaggatcc     180
ggggtccctg acaggtttag tggcagtggg tctgggacag acttcaccct caccatctcc     240
cctctgcagg ccgaggatgt ggcagtgtat ttctgtcaac aaagtaagga ggttccgtgg     300
acgttcggtc agggcaccaa gctggaaatc aag                                  333
```

<210> SEQ ID NO 134
<211> LENGTH: 111
<212> TYPE: PRT
<213> ORGANISM: Artificial Sequence
<220> FEATURE:
<223> OTHER INFORMATION: LV3 amino acids

<400> SEQUENCE: 134

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30
```

```
Gly Ile Ser Phe Met Asn Trp Phe Gln Gln Lys Pro Gly Gln Pro
            35                  40                  45

Lys Leu Leu Ile Tyr Ala Ala Ser Asn Gln Gly Ser Gly Val Pro Asp
 50                  55                  60

Arg Phe Ser Gly Ser Gly Ser Gly Thr Asp Phe Thr Leu Thr Ile Ser
 65                  70                  75                  80

Pro Leu Gln Ala Glu Asp Val Ala Val Tyr Phe Cys Gln Gln Ser Lys
                 85                  90                  95

Glu Val Pro Trp Thr Phe Gly Gln Gly Thr Lys Leu Glu Ile Lys
            100                 105                 110

<210> SEQ ID NO 135
<211> LENGTH: 333
<212> TYPE: DNA
<213> ORGANISM: Artificial Sequence
<220> FEATURE:
<223> OTHER INFORMATION: LV4

<400> SEQUENCE: 135
gacattgtgc tgacccaatc tccagactct ttggctgtgt ctctagggga gagggccacc      60
atcaactgca gagccagcga aagtgttgat aattatggca ttagttttat gaactggtac     120
caacagaaac caggacagcc acccaaactc ctcatctatg ctgcatccaa ccaaggatcc     180
ggggtccctg acaggtttag tggcagtggg tctgggacag acttcaccct caccatctcc     240
cctatgcagg ccgaggatgt ggcaatgtat tactgtcaac aaagtaagga ggttccgtgg     300
acgttcggtc agggcaccaa gctggaaatc aag                                  333

<210> SEQ ID NO 136
<211> LENGTH: 111
<212> TYPE: PRT
<213> ORGANISM: Artificial Sequence
<220> FEATURE:
<223> OTHER INFORMATION: LV4 amino acids

<400> SEQUENCE: 136

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Glu Ser Val Asp Asn Tyr
             20                  25                  30

Gly Ile Ser Phe Met Asn Trp Tyr Gln Gln Lys Pro Gly Gln Pro Pro
            35                  40                  45

Lys Leu Leu Ile Tyr Ala Ala Ser Asn Gln Gly Ser Gly Val Pro Asp
 50                  55                  60

Arg Phe Ser Gly Ser Gly Ser Gly Thr Asp Phe Thr Leu Thr Ile Ser
 65                  70                  75                  80

Pro Met Gln Ala Glu Asp Val Ala Met Tyr Tyr Cys Gln Gln Ser Lys
                 85                  90                  95

Glu Val Pro Trp Thr Phe Gly Gln Gly Thr Lys Leu Glu Ile Lys
            100                 105                 110

<210> SEQ ID NO 137
<211> LENGTH: 333
<212> TYPE: DNA
<213> ORGANISM: Artificial Sequence
<220> FEATURE:
<223> OTHER INFORMATION: LV6

<400> SEQUENCE: 137
```

```
gacattgtgc tgacccaatc tccagactct ttggctgtgt ctctagggga gagggccacc    60
atcaactgca gagccagcga aagtgttgat aattatggca ttagttttat gaactggttc   120
caacagaaac caggacagcc acccaaactc ctcatctatg ctgcatccaa ccaaggatcc   180
ggggtccctg acaggtttag tggcagtggg tctgggacag acttcaccct caccatctcc   240
cctatgcagg ccgaggatgt ggcaatgtat ttctgtcaac aaagtaagga ggttccgtgg   300
acgttcggtc agggcaccaa gctggaaatc aag                                333
```

<210> SEQ ID NO 138
<211> LENGTH: 111
<212> TYPE: PRT
<213> ORGANISM: Artificial Sequence
<220> FEATURE:
<223> OTHER INFORMATION: LV6 amino acids

<400> SEQUENCE: 138

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Asp
        50                  55                  60

Arg Phe Ser Gly Ser Gly Ser Gly Thr Asp Phe Thr Leu Thr Ile Ser
65                  70                  75                  80

Pro Met Gln Ala Glu Asp Val Ala Met Tyr Phe Cys Gln Gln Ser Lys
                85                  90                  95

Glu Val Pro Trp Thr Phe Gly Gln Gly Thr Lys Leu Glu Ile Lys
            100                 105                 110
```

<210> SEQ ID NO 139
<211> LENGTH: 35
<212> TYPE: PRT
<213> ORGANISM: Artificial Sequence
<220> FEATURE:
<223> OTHER INFORMATION: Human BMP10 region C

<400> SEQUENCE: 139

```
Val Pro Thr Lys Leu Glu Pro Ile Ser Ile Leu Tyr Leu Asp Lys Gly
1               5                   10                  15

Val Val Thr Tyr Lys Phe Lys Tyr Glu Gly Met Ala Val Ser Glu Cys
                20                  25                  30

Gly Cys Arg
            35
```